US006855706B2

(12) United States Patent
Tanaka et al.

(10) Patent No.: US 6,855,706 B2
(45) Date of Patent: Feb. 15, 2005

(54) PHENYLALANINE DERIVATIVES

(75) Inventors: Yasuhiro Tanaka, Kawasaki (JP); Toshihiko Yoshimura, Kawasaki (JP); Hiroyuki Izawa, Kawasaki (JP); Chieko Ejima, Kawasaki (JP); Mitsuhiko Kojima, Kawasaki (JP); Yuko Satake, Kawasaki (JP); Eiji Nakanishi, Kawasaki (JP); Nobuyasu Suzuki, Kawasaki (JP); Shingo Makino, Kawasaki (JP); Manabu Suzuki, Kawasaki (JP); Masahiro Murata, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/150,067

(22) Filed: May 20, 2002

(65) Prior Publication Data

US 2003/0149083 A1 Aug. 7, 2003

Related U.S. Application Data

(63) Continuation of application No. PCT/JP00/08152, filed on Nov. 20, 2000.

(30) Foreign Application Priority Data

Nov. 18, 1999 (JP) ........................................ 11-328468
Jun. 29, 2000 (JP) ........................................ 2000-197139

(51) Int. Cl.[7] .................... C07C 233/47; C07C 233/63; C07C 233/81; A61K 31/198; A61K 31/40

(52) U.S. Cl. ........................... 514/210.17; 514/217.11; 514/224.2; 514/230.5; 514/231.2; 514/249; 514/255.01; 514/327; 514/330; 514/423; 514/563; 540/607; 544/41; 544/105; 544/168; 544/169; 544/349; 544/391; 546/221; 546/225; 548/539; 548/540; 548/953; 562/433; 562/445; 562/447; 562/448

(58) Field of Search ............................... 548/540, 539, 548/953; 562/433, 445, 447, 448; 514/423, 563, 210.17, 217.11, 224.2, 230.5, 231.2, 249, 255.01, 330; 544/47, 105, 168, 169, 349, 391; 546/221, 225; 540/607

(56) References Cited

U.S. PATENT DOCUMENTS

| | | | | |
|---|---|---|---|---|
| 6,610,710 B2 | * | 8/2003 | Tanaka et al. | 514/330 |
| 2003/0130320 A1 | * | 7/2003 | Suzuki et al. | 514/346 |

FOREIGN PATENT DOCUMENTS

| | | | |
|---|---|---|---|
| EP | 358398 | * | 3/1990 |
| WO | WO 91/13054 | * | 9/1991 |
| WO | WO 99/10313 | | 3/1999 |
| WO | WO 01/12183 | | 2/2001 |

OTHER PUBLICATIONS

Lobb et al., PubMed Abstract (Ann N Y Acad Sci. 796:113–23), October 1996.*

Foster, PubMed Abstract (J Allergy Clin Immunol. 98(6 Pt 2):S270–7, December 1996.*

Griffioen et a., Tumor Angiogenesis Is Accompanied by a Decreased Inflammatory Response of Tumor–Associated Endothelium, Blood, vol. 88, No. 2, pp. 667–673, 1996.*

Mann et al., Cell Cycle Inhibition Preserves Endothelial Function in Genetically Engineered Rabbit Vein Grafts, J. Clin. Invest. vol. 99, No. 6, pp. 1295–1301, March 1997.*

Spragg et al., Immunotargeting of Iiposomes to activated vascular endothelial cells: A strategy for site–selective delivery in the cardiovascular system, Proc. Natl. Acad. Sci. USA, vol. 94, pp. 8795–8800, August 1997.*

Humphries et al., PubMed Abstract (Ciba Found Symp. 189:177–91; discussion 191–9), 1995.*

* cited by examiner

*Primary Examiner*—Deepak Rao
(74) *Attorney, Agent, or Firm*—Oblon, Spivak, McClelland, Maier & Neustadt., P.C.

(57) ABSTRACT

Specified phenylalanine derivatives and analogues thereof have an antagonistic activity to α 4 integrin. They are used as therapeutic agents for various diseases concerning α 4 integrin.

20 Claims, No Drawings

PHENYLALANINE DERIVATIVES

This application is a continuation of PCT/JP00/08152 filed Nov. 20, 2000.

BACKGROUND OF THE INVENTION

The present invention relates to new phenylalanine derivatives and the use of the phenylalanine derivatives as medicines. It was reported that α 4 integrins participate in diseases in which α 4 integrin-depending adhesion process participates in the pathology, such as inflammatory diseases, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection. The compounds of the present invention having an antagonistic effect on the α 4 integrins are usable as therapeutic agents or preventive agents for the above-described diseases.

In the inflammatory reactions, it is generally understood that when a microorganism invades a tissue or when the tissue is injured, leukocytes play an important role for the exclusion of the microorganism or for the reparation of the injured tissue. It is also widely understood that in such cases, leukocytes usually circulating in the blood must pass through the vascular wall and be newly supplied to the injured tissue. It has been elucidated that the infiltration of the leukocytes from the blood vessel into the tissue is carried out by integrin molecules which are a group of heterodimeric proteins expressing on the leukocytes. The integrin molecules are classified into at least 8 subfamilies (β 1 through β 8 subfamilies) depending on the β chains thereof. Known typical subfamilies are β 1 and β 3 subfamilies involved in the adhesion of cell ingredients to the extracellular matrixes such as collagen and fibronectin; β 2 subfamily involved in cell-to-cell adhesion in the immune system; and β 7 subfamily which mainly participates in the infiltration of leukocytes into mucosal tissues (Shimizu et al., Adv. Immunol. 72: 325–380, 1999). As for the above-described α 4 integrins, two kinds of molecules thereof are known. They are VLA-4 (very late antigen-4) molecule belonging to the β 1 subfamily and comprising α 4 β 1 chain and LPAM-1 (lymphocyte Peyer's patch HEV adhesion molecule-1) molecule belonging to the β 7 subfamily and comprising α 4 β 7 chain. Usually most of leukocytes circulating in the blood have only a low adhesion affinity for the vascular-endothelium cells and they cannot move out of the blood vessel. On the other hand, lymphocytes mainly comprising T cells and B cells are capable of moving out of the blood vessel by a so-called lymphocyte homing phenomenon wherein they move from the blood into the lymphoid tissue through the blood vessel wall and then they return into the blood through the lymph vessel under the physiological conditions. It is known that LPAM-1 molecules participate in the lymphocyte homing into the lymphoid tissue of an bowel tract such as Peyer's patch (Butcher et al., Adv. Immunol. 72: 209–253, 1999). On the other hand, when an inflammation occurs, the vascular-endothelium cells are activated by cytokine and chemokine released from the inflamed tissue, the expression of a group of cell surface antigens (adhesion molecules) participating in the adhesion of leukocytes to the vascular-endothelium cells is caused, and a lot of leukocytes infiltrate out of the blood vessel toward the inflamed tissue through the adhesion molecules.

As the cell surface antigens on the vascular-endothelium cells participating in the adhesion of the leukocytes, there have been known E-selectin (adhesion molecule mainly participating in the adhesion of neutrophilic leukocytes), ICAM-1 and VCAM-1 mainly participating in the adhesion of lymphocytes, and MAdCAM-1 mainly participating in the adhesion of lymphocytes in the lymphoid tissue of an bowel tract such as Peyer's patch (Shimizu et al., Adv. Immunol. 72: 325–380, 1999). It was reported that in those adhesion molecules, VCAM-1 acts as a ligand of both VLA-4 and LPAM-1 and that MAdCAM-1 acts as the ligand of LPAM-1. As a ligand of both VLA-4 and LPAM-1, fibronectin which is a kind of extracellular matrixes is also known (Shimizu et al., Adv. Immunol. 72: 325–380, 1999). The β-1 integrin subfamily to which VLA-4 belongs comprises at least 6 integrins (VLA-1 to VLA-6) using extracellular matrixes such as fibronectin, collagen and laminin as the ligands. Many of integrins using extracellular matrixes as the ligands, such as VLA-5, β-3 subfamily and β-5 subfamily, recognize arginine—glycine—aspartic acid (RGD) sequence in fibronectin, vitronectin, tenascin and osteopontin. On the other hand, in the interaction of VLA-4 and fibronectin, the RGD sequence does not participate but a CS-1 peptide segment comprising leucine—aspartic acid—valine (LDV) as the core sequence participates (Pulido et al., J. Biol. Chem. 266: 10241–10245, 1991). Clements et al. found a sequence similar to LDV in amino acid sequences of VCAM-1 and MAdCAM-1. It has been elucidated that a variant obtained by partially modifying the CS-1-like sequence of VCAM-1 and MAdCAM-1 molecules cannot bound to VLA-4 or LPAM-1 (Clements et al., J. Cell Sci. 107: 2127–2135, 1994, Vonderheide et al., J. Cell. Biol. 125: 215–222, 1994, Renz et al., J. Cell. Biol. 125: 1395–1406, 1994, and Kilger et al., Int. Immunol. 9: 219–226, 1997). Thus, it was found that the CS-1-like sequence is important for the binding of VLA-4/LPAM-1 and VCAM-1/MAdCAM-1.

It was reported that the same cyclic peptide having the CS-1-like structure is antagonistic both to the binding of VLA-4 or LPAM-1 with VCAM-1, MAdCAM-1 or CS-1 peptide (Vanderslice et al., J. Immunol. 158: 1710–1718, 1997). The above-described facts indicate that all the interactions of α 4 integrin and VCAM-1, MAdCAM-1 or fibronectin can be blocked by using a suitable α 4 integrin antagonist (the term "α 4 integrin antagonist" herein indicates a substance antagonistic to α 4 β 1 and/or α 4 β 7 integrin).

It is also known that the expression of VCAM-1 in vascular-endothelium cells is caused by inflammatory factors such as LPS, TNF-α or IL-1 and that when the inflammation occurs, the infiltration of the leukocytes from the blood vessel into the tissue is carried out by the VLA-4/VCAM-1 adhesion mechanism (Elices, Cell 60: 577–584, 1990, Osborn et al., Cell 59: 1203–1211, 1989 and Issekutz et al., J. Eex. Med. 183: 2175–2184, 1996). Because VLA-4 is expressed on the surfaces of activated lymphocytes, monocytes, eosinophil, mast cells and neutrophil, the adhesion mechanism of VLA-4/VCAM-1 plays an important role for the infiltration of those cells into the inflamed tissue. It was reported that VLA-4 is expressed on various sarcoma cells such as melanoma cells, and it was also elucidated that the adhesion mechanism of VLA-4/VCAM-1 participates in the metastasis of these tumors. By investigating the expression of VCAM-1 in various pathological tissues, it was made apparent that the adhesion mechanism of this VLA-4/VCAM-1 participates in various pathological stages. Namely, it was reported that in addition to the activated vascular-endothelium cells, the expression of VCAM-1 is increased in the inflamed tissues in the patients with autoimmune diseases such as rheumatoid synovial membrane (van Dinther-Janssen, J. Immunol. 147: 4207–4210, 1991 and Morales-Ducret et al., J. Immunol. 149: 1424–1431, 1992), lungs and respiratory tract epithelium in asthma (ten Hacken et al., Clin. Exp. Allergy 12: 1518–1525, 1998) and allergic diseases (Randolph et al., J. Clin. Invest. 104: 1021–1029, 1999), systemic erythematodes (Takeuchi et al., J. Clin. Invest. 92: 3008–3016, 1993), Sjogren's syndrome (Edwards et al., Ann. Rheum. Dis. 52: 806–811, 1993), multiple sclerosis (Steffen et al., Am. J. Pathol. 145: 189–201, 1994) and psoriasis (Groves et al., J. Am. Acad. Dermatol. 29: 67–72, 1993); atherosclerotic plagues (O'Brien et al., J. Clin. Invest. 92: 945–951, 1993), bowel tissues of the patients with inflammatory bowel diseases such as Crohn's disease and ulcerative colitis (Koizumi et al., Gastroenterol. 103: 840–847, 1992 and Nakamura et al., Lab. Invest. 69: 77–85, 1993), inflamed tissue of Langerhans island of patients with diabetes (Martin et al., J. Autoimmun. 9: 637–643, 1996) and implants during the rejection of transplantation of heart or kidney (Herskowitz et al. Am. J. Pathol. 145: 1082–1094, 1994 and Hill et al., Kidney Int. 47: 1383–1391, 1995). The adhesion mechanism of VLA-4/VCAM-1 participates in these various diseases.

There are many reports showing that in vivo administration of VLA-4 or VCAM-1 antibody was effective in improving the diseases of animal models with those inflammatory diseases. Concretely, Yednock et al. and Baron et al. reported that the in vivo administration of an antibody against α 4 integrins was effective in controlling the incidence rate or in controlling encephalomyelitis in the experimental autoimmune encephalomyelitis models, i.e. multiple sclerosis models (Yednock et al., Nature 356: 63–66, 1992 and Baron et al., J. Exp. Med. 177: 57–68, 1993). Zeider et al. reported that in vivo administration of an antibody against α 4-integrin was effective in controlling the incidence rate of mouse collagen arthritis (rheumatism models) (Zeidler et al., Autoimmunity 21: 245–252, 1995). The therapeutic effect of an antibody against a 4-integrin in asthma models was reported by Abraham et al. and Sagara et al. (Abraham et al., J. Clin. Invest. 93: 776–787, 1994 and Sagara et al., Int. Arch. Allergy Immunol. 112: 287–294, 1997). The effect of an antibody against a 4-integrin in inflammatory bowel disease models was reported by Podolsky et al. (Podolsky et al., J. Clin. Invest. 92: 372–380, 1993). The effect of an antibody against a 4-integrin and that against VCAM antibody in insulin-dependent diabetes models were reported by Baron et al. (Baron et al., J. Clin. Invest. 93: 1700–1708, 1994). It was made apparent with baboon models that the restenosis of a blood vessel after an angioplasty carried out because of arteriosclerosis can be inhibited by the administration of a 4 integrin antibody (Lumsden et al., J. Vasc. Surg. 26: 87–93, 1997). It was also reported that a 4 integrin or VCAM antibody is effective in inhibiting the rejection of an implant or inhibiting metastasis of a cancer (Isobe et al., J. Immunol. 153: 5810–5818, 1994 and Okahara et al., Cancer Res. 54: 3233–3236, 1994).

As described above, unlike VCAM-1, MAdCAM-1 which is a ligand of LPAM-1 is constantly expressed on high endothelial venules (HEV) in the bowel mucous membrane, mesenteric lymph nodes, Peyer's patch and spleen and it participates in the homing of mucosal lymphocytes. It is also known that LPAM-1/MAdCAM-1 adhesion mechanism not only has physiological roles in the homing of the lymphocytes but also participates in some pathological processes. Briskin et al reported an increase in the expression of MAdCAM-1 in inflamed regions in bowel tracts of patients with inflammatory bowel diseases such as Crohn's disease and ulcerative colitis (Briskin et al., Am. J. Pathol. 151: 97–110, 1997). Hanninen et al. reported that induction of the expression is observed in an inflamed tissue of Langerhans island which is a model of an insulin-dependent diabetes (Hanninen et al., J. Immunol. 160: 6018–6025, 1998). The fact that LPAM-1/MAdCAM-1 adhesion mechanism participates in the progress of diseases is apparent from the fact that conditions of mouse models with inflammatory bowel disease (Picarella et al., J. Immunol. 158: 2099–2106, 1997) and the above-described NOD mouse models are improved by the in vivo administration of antibody to MAdCAM or antibody to β-7 integrin (Hanninen et al., J. Immunol. 160: 6018–6025, 1998 and Yang et al., Diabetes 46: 1542–1547, 1997).

The above-described facts indicate the possibility of employing the blocking of VLA-4/VCAM-1, LPAM-1/VCAM-1 or LPAM-1/MAdCAM-1 adhesion mechanism by a suitable antagonist is effective in treating the chronic inflammatory diseases described above. The use of the antibody against VLA-4 as the VLA-4 antagonist is described in WO 93/13798, WO 93/15764, WO 94/16094 and WO 95/19790. Peptide compounds as VLA-4 antagonists are described in WO 94/15958, WO 95/15973, WO 96/00581 and WO 96/06108. Amino acid derivatives usable as VLA-4 antagonists are described in WO 99/10313 and WO 99/36393. However, none of them is practically used for the therapeutic treatment at present because of the lack of oral bioavailability and immunogenic properties during the use of them for a long period of time.

DISCLOSURE OF THE INVENTION

An object of the present invention is to provide new compounds having α 4 integrin antagonistic effect.

Another object of the present invention is to provide a pharmaceutical composition containing such new compounds.

Still another object of the present invention is to provide α 4 integrin antagonists.

A further object of the present invention is to provide therapeutic agents or preventive agents for diseases in which α 4 integrin-depending adhesion process participates in the pathology, such as inflammatory diseases, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection.

For the purpose of solving the above-described problems, the inventors have synthesized various phenylalanine derivatives and examining α 4 integrin antagonistic activities thereof, and the inventors have found that specified, new phenylalanine derivatives, particularly compounds of the following general formula (1) wherein Z represents a group of the formula: —C(═O)— or the like have an excellent α 4 integrin antagonistic activity. The present invention has been completed on the basis of this finding.

Namely, the present invention provides phenylalanine derivatives of the following general formula (1) and pharmaceutically acceptable salts thereof:

(1)

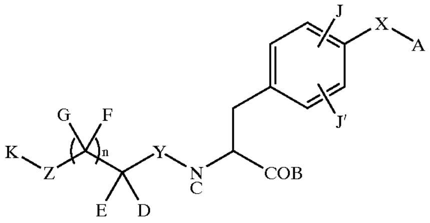

wherein X represents an interatomic bond, —O—, —O—$SO_2$—, —$NR^1$—, —$NR^1$—(=O)—, —$NR^1$—$SO_2$—, —$NR^1$—C(=O)—NH—, —$NR^1$—C(=S)—NH— or —C(=O)— wherein $R^1$ represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), Y represents —C(=O)—, —S(=O)— or —$SO_2$—, Z represents —C(=O)—, —S(=O)— or —$SO_2$—, A represents a group of the following general formula (2), a group of any of the following general formulae (2-1) to (2-5), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with a group of general formula (2), a lower alkyl group substituted with an aryl group(s), a lower alkyl group substituted with a heteroaryl group(s), a lower alkenyl group substituted with a cycloalkyl group (s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s) or a lower alkynyl group substituted with a heteroaryl group(s):

(2)

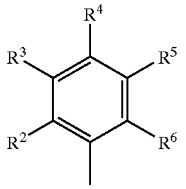

wherein $R^2$, $R^3$, $R^4$, $R^5$ and $R^6$ may be the same or different from one another, and each represent a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group:

(2-1)

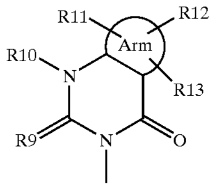

(2-2)

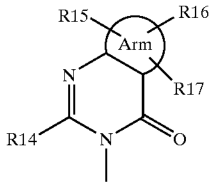

(2-3)

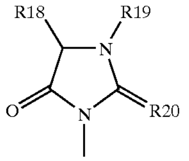

(2-4)

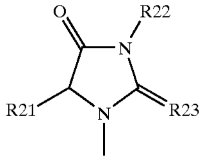

(2-5)

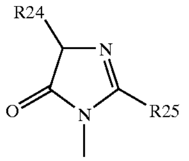

wherein Arm represents benzene ring or an aromatic ring containing 1, 2, 3 or 4 hetero atoms selected from among oxygen, sulfur and nitrogen atoms, $R^9$ represents oxygen atom, a substituted or unsubstituted imino group or sulfur atom, $R^{10}$, $R^{11}$, $R^{12}$ and $R^{13}$ may be the same or different from one another and each represent a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom (s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, $R^{14}$, $R^{15}$, $R^{16}$ and $R^{17}$ may be the same or different from one another and each represent a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, $R^{20}$ represents oxygen atom, a substituted or unsubstituted imino group or sulfur atom, $R^{18}$ and $R^{19}$ may be the same or different from each other and each represent a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group, a halogeno-lower alkenyl group, a hydroxy-lower alkyl group, a hydroxy-lower alkenyl group or a substituted or unsubstituted amino-lower alkyl group, or $R^{18}$ and $R^{19}$ may be bonded together to form a ring which may contain one or two oxygen, nitrogen or sulfur atoms, and the substituents of the ring include a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, $R^{23}$ represents oxygen atom, a substituted or unsubstituted imino group or sulfur atom, $R^{21}$ and $R^{22}$ may be the same or different from each other and each represent a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom (s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, $R^{24}$ and $R^{25}$ may be the same or different from each other and each represent a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom (s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, B represents hydroxyl group, a lower alkoxyl group or hydroxyamino group, C represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group (s), D and E may be the same or different from each other and each represent a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group, a lower alkoxy-lower alkyl group, a hydroxy-lower alkyl group, a lower alkylthio-lower alkyl group, a mercapto-lower alkyl group or a substituted or unsubstituted amino-lower alkyl group, or D and E may be bonded together to form a ring which may contain one or two oxygen, nitrogen or sulfur atoms, F and G may be the same or different from each other and each represent hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group or a hydroxy-lower alkyl group, or F and G may be bonded together to form a ring which may contain one or two oxygen, nitrogen or sulfur atoms, n represents an integer of 0 to 2, K represents $OR^7$, $NR^7R^8$, $NHNR^7R^8$, $NR^7NHR^8$, $SR^7$ or $R^7$ wherein $R^7$ and $R^8$ may be the same or different from each other and each represent a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group, a halogeno-lower alkenyl group, a hydroxy-lower alkyl group, a hydroxy-lower alkenyl group or a substituted or unsubstituted amino-lower alkyl group, or $R^7$ and $R^8$ may be bonded together to form a ring which may contain one or two oxygen, nitrogen or sulfur atoms; and the substituents of the ring include a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and J and J' may be the same or different from each other and each represent a hydrogen atom, a halogen atom, a lower alkyl group, a lower alkyloxy group or nitro group.

The present invention provides a pharmaceutical composition and an α 4 integrin antagonist containing the above-described phenylalanine derivative or a pharmaceutically acceptable salt thereof as the active ingredient.

The present invention also provides a therapeutic agent or preventive agent, containing the phenylalanine derivative or a pharmaceutically acceptable salt thereof as the active ingredient, for diseases in which α 4 integrin-depending adhesion process participates in the pathology, such as inflammatory diseases, rheumatoid arthritis, inflammatory bowel diseases, systemic lupus erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection.

BEST MODE FOR CARRYING OUT THE INVENTION

The term "lower" in, for example, a lower alkyl group indicates that the group has 1 to 6 carbon atoms. Alkyl groups per se and also alkyl groups in alkenyl groups, alkynyl groups, alkoxyl groups, alkylthio groups, alkanoyl groups and alkylamino groups, alkenyl groups and alkynyl groups may be either linear or branched. Examples of these alkyl groups are methyl group, ethyl group, propyl group, isopropyl group, butyl group, secondary butyl group, tertiary butyl group, pentyl group and hexyl group. The alkenyl groups are, for example, vinyl group, propenyl group, butenyl group and pentenyl group. The alkynyl groups include ethynyl group, propynyl group and butynyl group. The cycloalkyl groups indicate substituted or unsubstituted cycloalkyl groups such as cyclopropyl group, cyclobutyl group, cyclopentyl group, cyclohexyl group, norbornyl group, adamantyl group and cyclohexenyl group. The alkoxyl groups include methoxyl group, ethoxyl group, propyloxy group, isopropyloxy group, etc. The hetero atoms include nitrogen, oxygen, sulfur, etc. The halogen atoms are fluorine, chlorine, bromine and iodine. The halogenoalkyl groups include chloromethyl group, trichloromethyl group, trifluoromethyl group, trifluoroethyl group, pentafluoroethyl group, etc. The halogenoalkoxyl groups include trichloromethoxyl group, trifluoromethoxyl group, etc. The hydroxyalkyl groups include hydroxymethyl group, hydroxyethyl group, etc. The cycloalkyl groups which may contain a hetero atom(s) in the ring thereof may be either substituted or unsubstituted. Examples of them include piperidyl group, piperazinyl group, morpholinyl group, pyrrolidinyl group, tetrahydrofuranyl group and groups of above general formula (2-1), (2-2), (2-3), (2-4) or (2-5).

In the present specification, the aryl groups are both substituted and unsubstituted aryl groups such as phenyl group, 1-naphthyl group and 2-naphthyl group. They are preferably phenyl group and substituted phenyl group, and the substituents are particularly preferably halogen atoms, alkoxyl groups, alkyl groups, hydroxyl group, halogenoalkyl groups, halogenoalkoxyl groups, nitro group and phenyl group. The heteroaryl groups are both substituted and unsubstituted heteroaryl groups such as pyridyl group, pyrimidinyl group, furyl group, thienyl group, indolyl group, quinolyl group and isoquinolyl group. Preferred heteroaryl groups are pyridyl group, pyrimidinyl group, furyl group, thienyl group and substituted pyridyl, pyrimidinyl, furyl and thienyl groups. Particularly preferred substituents are halogen atoms, alkoxyl groups, alkyl groups, hydroxyl group, halogenoalkyl groups, halogenoalkoxyl groups, lower alkylthio groups, lower alkylsulfinyl groups, lower alkylsulfonyl groups and substituted or unsubstituted amino groups. The lower alkyl groups substituted with an aryl group(s) include, for example, benzyl group and substituted benzyl groups. Particularly preferred substituents are halogen atoms, alkoxyl groups, alkyl groups, hydroxyl group, halogenoalkyl groups, halogenoalkoxyl groups, substituted or unsubstituted amino groups and alkylthio groups. The lower alkyl groups substituted with a heteroaryl group(s) include, for example, pyridylmethyl group, and particularly preferred substituents thereof are halogen atoms, alkoxyl groups, alkyl groups, hydroxyl group, halogenoalkyl groups and halogenoalkoxyl groups. The alkanoyl groups include, for example, formyl groups, acetyl groups, propanoyl group, butanoyl group and pivaloyl group. The aroyl groups include, for example, substituted or unsubstituted benzoyl group and pyridylcarbonyl group, and the substituents thereof are particularly preferably halogen atoms, alkoxyl groups, alkyl groups, hydroxyl group, halogenoalkyl groups and halogenoalkoxyl groups. The halogenoalkanoyl groups include, for example, trichloroacetyl group and trifluoroacetyl group. The alkylsulfonyl groups include, for example, methanesulfonyl group, ethanesulfonyl group, etc. The arylsulfonyl groups include, for example, benzenesulfonyl group and p-toluenesulfonyl group. The heteroarylsulfonyl groups include, for example, pyridylsulfonyl group. The halogenoalkylsulfonyl groups include, for example, trifluoromethanesulfonyl group. The alkyloxycarbonyl groups include, for example, methoxycarbonyl group, ethoxycarbonyl group and tert-butoxycarbonyl group. The aryl-substituted alkoxycarbonyl groups include, for example, benzyloxycarbonyl group and 9-fluorenylmethoxycarbonyl group. The substituted carbamoyl groups include, for example, methylcarbamoyl group, phenylcarbamoyl group and substituted phenylcarbamoyl group, and the substituents thereof are particularly preferably halogen atoms, alkoxyl groups, alkyl groups, hydroxyl group, halogenoalkyl groups and halogenoalkoxyl groups. The substituted thiocarbamoyl groups include, for example, methylthiocarbamoyl group, phenylthiocarbamoyl group and substituted phenylthiocarbamoyl groups, and the substituents thereof are particularly preferably halogens, alkoxyl groups, alkyl groups, hydroxyl group, halogenoalkyl groups and halogenoalkoxyl groups. The substituents of the substituted amino groups herein include lower alkyl groups, lower alkyl groups substituted with an aryl group, lower alkyl groups substituted with a heteroaryl group, lower alkanoyl groups, aroyl groups, halogeno-lower alkanoyl groups, lower alkylsulfonyl groups, arylsulfonyl groups, heteroarylsulfonyl groups, halogenoalkylsulfonyl groups, lower alkyloxycarbonyl groups, aryl-substituted lower alkyloxycarbonyl groups, substituted or unsubstituted carbamoyl groups and substituted or unsubstituted thiocarbamoyl groups.

The group represented by X in the above general formula (1) is preferably an interatomic bond, —O—, —O—$SO_2$—, —$NR^1$—, —$NR^1$—C(=O)—, —$NR^1$—$SO_2$—, or —C(=O)—. The group represented by X is particularly preferably an interatomic bond, —O— or —$NR^1$—C(=O)—.

The group represented by Y is preferably —C(=O)—.

The group represented by Z is preferably —C(=O)— or —$SO_2$—. It is particularly preferably —C(=O).

In the groups represented by A, the cycloalkyl groups which may contain a hetero atom(s) in the ring thereof, aryl groups and heteroaryl groups are either substituted or unsubstituted. The substituents thereof are those described above with reference to $R^2$ to $R^6$. The groups represented by A are preferably groups of general formula (2), lower alkyl groups, lower alkenyl groups, lower alkynyl groups, cycloalkyl groups which may contain a hetero atom(s) in the ring thereof, aryl groups, heteroaryl groups, lower alkyl groups substituted with a cycloalkyl group(s) which may contain a hetero atom(s) in the ring thereof, lower alkyl groups substituted with a group of general formula (2), lower alkyl groups substituted with an aryl group(s) and lower alkyl groups substituted with a heteroaryl group(s). The groups represented by A are particularly preferably lower alkyl groups substituted with a group of general formula (2), groups represented by general formulae (2-1), (2-2), (2-3), (2-4) or (2-5) and substituted heteroaryl groups. Among them, the lower alkyl groups substituted with a group of general formula (2), heteroaryl groups and groups represented by general formula (2-1) are preferred.

The group represented by B is preferably a hydroxyl group.

The group represented by C is preferably a hydrogen atom.

In the groups represented by D, E, F or G, the cycloalkyl groups which may contain a hetero atom(s) in the ring thereof, aryl groups and heteroaryl groups are either unsubstituted or substituted, and the substituents are those described above with reference to $R^2$ to $R^6$. The groups represented by D or E are preferably lower alkyl groups, particularly ethyl group. It is also preferred that D and E are bonded to each other to form a ring which may contain 1 or 2 oxygen atoms, nitrogen atoms or sulfur atoms. The groups represented by F or G is preferably hydrogen atom or lower alkyl groups.

n is preferably an integer of 0.

In the groups represented by $R^7$ or $R^8$ among those represented by K, the cycloalkyl groups which may contain a hetero atom(s) in the ring thereof, aryl groups and heteroaryl groups are either substituted or unsubstituted, and the substituents are those described above with reference to $R^2$ to $R^6$.

As the groups represented by K, those represented by $NR^7R^8$ or $NHNR^7R^8$ are preferred. $R^7$ and $R^8$, which may be the same or different from each other, are each preferably hydrogen atom, a lower alkyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), or a lower alkyl group substituted with a heteroaryl group(s). It is also preferred that $R^7$ and $R^8$ are bonded to each other to form a ring which may contain 1 or 2 oxygen atoms nitrogen atoms or sulfur atoms. The substituents of the ring are preferably hydrogen atoms, halogen atoms, hydroxyl groups, lower alkyl groups, aryl groups, heteroaryl groups, lower alkyl groups substituted with an aryl group, lower alkanoyl groups, aroyl groups, lower alkyloxy groups, nitro groups, cyano groups, substituted or unsubstituted amino groups, carboxyl groups, lower alkoxycarbonyl groups, lower alkoxycarbonyl groups substituted with an aryl group(s), substituted or unsubstituted carbamoyl groups, substituted or unsubstituted thiocarbamoyl groups, lower alkylthio groups, lower alkylsulfonyl groups and substituted or unsubstituted sulfamoyl groups.

As the groups represented by K, those represented by $NR^7R^8$ are particularly preferred. In the group represented by $NR^7R^8$, it is preferred that $R^7$ and $R^8$ are bonded to each other to form a ring. Examples of the groups K of formula $NR^7R^8$ wherein $R^7$ and $R^8$ together form a ring are piperidine-1-yl group, piperazine-1-yl group, morpholine-4-yl group and pyrrolidine-1-yl group.

Groups represented by J or J' is preferably a hydrogen atom.

The substituents of $R^2$ to $R^6$ are more preferably hydrogen atoms, halogen atoms, hydroxyl groups, lower alkyl groups, lower alkoxyl groups, halogeno-lower alkyl groups and halogeno-lower alkoxyl groups.

When the group K is represented by $NR^7R^8$, the groups $R^7$ and $R^8$ are each more preferably a lower alkyl group, an aryl group or a substituted aryl group, and the substituents of the aryl group are preferably hydrogen atoms, halogen atoms, hydroxyl groups, lower alkyl groups, lower alkoxyl groups, halogeno-lower alkyl groups and halogeno-lower alkoxyl groups. When $R^7$ and $R^8$ in N $R^7R^8$ are bonded to each other to form a ring, the ring is preferably an azetidine ring, pyrrolidine ring, piperidine ring or piperazine ring. The substituents of the ring are preferably lower alkyl groups, halogen atoms, aryl groups, substituted aryl groups, hydroxyl groups and substituted or unsubstituted amino groups. The substituents of the aryl groups are preferably hydrogen atoms, halogen atoms, hydroxyl groups, lower alkyl groups, lower alkoxyl groups, halogeno-lower alkyl groups and halogeno-lower alkoxyl groups. The substituents of the amino group are preferably lower alkyl groups and lower alkanoyl groups.

It is preferred that in general formula (1) in the present invention, X represents an interatomic bond or a group of the formula: —O—, —O—$SO_2$—, —$NR^1$—, —$NR^1$—C(═O)—, —$NR^1$—$SO_2$— or —C(═O)—, Y represents a group of the formula: —C(═O)—, Z represents a group of —C(═O)— or —O—$SO_2$—, A represents a group of general formula (2), a group of any of general formulae (2-1) to (2-5), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with a group of general formula (2), a lower alkyl group substituted with an aryl group(s) or a lower alkyl group substituted with a heteroaryl group(s), B represents hydroxyl group or a lower alkoxyl group, C represents hydrogen atom or a lower alkyl group, D and E may be the same or different and each represent a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group (s), a lower alkyl group substituted with a heteroaryl group (s), a lower alkenyl group substituted with an aryl group(s), a lower alkenyl group substituted with a heteroaryl group(s), a halogeno-lower alkyl group, a lower alkoxy-lower alkyl group, a hydroxy-lower alkyl group, a lower alkylthio-lower alkyl group, a mercapto-lower alkyl group or a substituted or unsubstituted amino-lower alkyl group, or D and E may be bonded together to form a ring which may contain one or two oxygen, nitrogen or sulfur atoms, and n represents an integer of 0.

It is preferred that in general formula (1) in the present invention, X represents an interatomic bond or a group of the formula: —O—, —O—$SO_2$—, —$NR^1$—, —$NR^1$—C(═O)—, —$NR^1$—$SO_2$—, —$NR^1$—C(═O)—NH— or —$NR^1$—C(═S)—NH—, wherein $R^1$ represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), Y represents any of —C(═O)—, —S(═O)— or —O—$SO_2$—, Z represents any of group of —C(═O)—, —S(═O)— or —$SO_2$—, A represents a group of general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with a group of general formula (2), a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s) or a lower alkynyl group substituted with a heteroaryl group(s).

$R^2$, $R^3$, $R^4$, $R^5$ and $R^6$ in general formula (2) may be the same or different from one another, and each represents a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom (s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group:

B represents hydroxyl group, a lower alkoxyl group or hydroxyamino group,

C represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group (s), D and E may be the same or different from each other and each represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group or a hydroxy-lower alkyl group, or D and E may be bonded together to form a ring which may contain one or two oxygen, nitrogen or sulfur atoms, F and G may be the same or different from each other and each represents a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group or a hydroxy-lower alkyl group, or F and G may be bonded together to form a ring which may contain one or two oxygen, nitrogen or sulfur atoms, n represents an integer of 0 to 2, K represents $OR^7$, $NR^7R^8$, $NHNR^7R^8$, $NR^7NHR^8$, $SR^7$ or $R^7$ wherein $R^7$ and $R^8$ may be the same or different from each other and each represents a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group, a halogeno-lower alkenyl group, a hydroxy-lower alkyl group, a hydroxy-lower alkenyl group or a substituted or unsubstituted amino-lower alkyl group, or $R^7$ and $R^8$ may be bonded together to form a ring which may contain one or two oxygen, nitrogen or sulfur atoms; and the substituents of the ring include a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and J and J' may be the same or different from each other and each represents a hydrogen atom, a halogen atom, a lower alkyl group, a lower alkyloxy group or nitro group.

It is preferred that in general formula (1), X represents a group of the formula: —O—, Y represents a group of the formula: —C(=O)—, Z represents a group of the formula: —C(=O)—, A represents a lower alkyl group substituted with a group of general formula (2), $R^2$, $R^3$, $R^4$, $R^5$ and $R^6$ may be the same or different from one another, and each represent a hydrogen atom or a halogen atom, B represents a hydroxyl group, C represents a hydrogen atom, D and E may be the same or different from each other and each represents a lower alkyl group, or D and E may be bonded together to form a ring which may contain one or two oxygen, nitrogen or sulfur atoms, n represents an integer of 0, K represents $NR^7R^8$ or $NHNR^7R^8$, $R^7$ and $R^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s) or $R^7$ and $R^8$ may be bonded together to form a ring which may contain one or two oxygen, nitrogen or sulfur atoms; and the substituents of the ring include a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and J and J' each represents hydrogen atom.

It is preferred that in general formula (1),

X represents a group of the formula: $—NR^1—C(=O)—$,

Y represents a group of the formula: —C(=O)—,

Z represents a group of the formula: —C(=O)—,

A represents a group of general formula (2) wherein $R^2$, $R^3$, $R^1$, $R^5$ and $R^6$ may be the same or different from one another, and each represent a hydrogen atom or a halogen atom, a cycloalkyl group which may contain a hetero atom(s) in the ring thereof or a heteroaryl group, B represents a hydroxyl group, C represents a hydrogen atom, D and E may be the same or different from each other and each represents a lower alkyl group, or D and E may be bonded together to form a ring which may contain one or two oxygen, nitrogen or sulfur atoms, n represents an integer of 0, K represents $NR^7R^8$ or $NHNR^7R^8$, $R^7$ and $R^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s) or $R^7$ and $R^8$ may be bonded together to form a ring which may contain one or two oxygen, nitrogen or sulfur atoms; and the substituents of the ring include a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and J and J' each represent a hydrogen atom.

It is preferred that in general formula (1),

X represents an interatomic bond,

Y represents a group of the formula: —C(=O)—,

Z represents a group of the formula: —C(=O)—,

A represents a cycloalkyl group which may contain a hetero atom(s) in the ring thereof or a heteroaryl group, B represents a hydroxyl group, C represents a hydrogen atom, D and E may be the same or different from each other and each represents a lower alkyl group, or D and E may be bonded together to form a ring which may contain one or two oxygen, nitrogen or sulfur atoms, n represents an integer of 0, K represents $NR^7R^8$, $R^7$ and $R^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s) or $R^7$ and $R^8$ may be bonded together to form a ring which may contain one or two oxygen, nitrogen or sulfur atoms; and the substituents of the ring include a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and J and J' and each represent a hydrogen atom.

A is preferably a cycloalkyl group containing a hetero atom(s) in the ring thereof, which is represented by any of formulae (2-1) to (2-5).

The following compounds and pharmaceutically acceptable salts thereof are preferred:

N-[2-(N,N-dimethylaminocarbonyl)-2-methyl-propanoyl]-O-(2,6-dichlorobenzyl)-L-tyrosine;

N-[2-(N,N-diethylaminocarbonyl)-2-methyl-propanoyl]-O-(2,6-dichlorobenzyl)-L-tyrosine;

N-[2-(N,N-dimethylaminocarbonyl)-2-ethyl-butanoyl]-O-(2,6-dichlorobenzyl)-L-tyrosine;

N-[2-(N,N-diethylaminocarbonyl)-2-methyl-butanoyl]-O-(2,6-dichlorobenzyl)-L-tyrosine;

N-[1-(N,N-dimethylaminocarbonyl)cyclopropane-1-ylcarbonyl]-O-(2,6-dichlorobenzyl)-L-tyrosine;

N-[1-(N,N-diethylaminocarbonyl)cyclopropane-1-ylcarbonyl]-O-(2,6-dichlorobenzyl)-L-tyrosine;

N-[2-(piperidine-1-ylcarbonyl)-2-methyl-propanoyl]-O-(2,6-dichlorobenzyl)-L-tyrosine;

N-[2-(piperidine-1-ylcarbonyl)-2-ethyl-butanoyl]-O-(2,6-dichlorobenzyl)-L-tyrosine;

N-[1-(piperidine-1-ylcarbonyl)cyclopropane-1-ylcarbonyl]-O-(2,6-dichlorobenzyl)-L-tyrosine;

N-[2-(N-methyl-N-phenylaminocarbonyl)-2-methyl-propanoyl]-O-(2,6-dichlorobenzyl)-L-tyrosine;

N-[2-(N-methyl-N-phenylaminocarbonyl)-2-ethyl-butanoyl]-O-(2,6-dichlorobenzyl)-L-tyrosine;

N-[1-(N-methyl-N-phenylaminocarbonyl)cyclopropane-1-ylcarbonyl]-O-(2,6-dichlorobenzyl)-L-tyrosine;

N-[2-(4-hydroxyphenylaminocarbonyl)-2-methyl-propanoyl]-O-(2,6-dichlorobenzyl)-L-tyrosine;

N-[2-(4-hydroxyphenylaminocarbonyl)-2-ethyl-butanoyl]-O-(2,6-dichlorobenzyl)-L-tyrosine;

N-[1-(4-hydroxyphenylaminocarbonyl)cyclopropane-1-ylcarbonyl]-O-(2,6-dichlorobenzyl)-L-tyrosine;

N-{2-[4-(4-hydroxyphenyl)piperazine-1-ylcarbonyl]-2-methyl-propanoyl}-O-(2,6-di-chlorobenzyl)-L-tyrosine;

N-{2-[4-(4-hydroxyphenyl)piperazine-1-ylcarbonyl]-2-ethyl-butanoyl}-O-(2,6-dichlorobenzyl)-L-tyrosine; and N-{1-[4-(4-hydroxyphenyl)piperazine-1-ylcarbonyl]-2-ethyl-butanoyl}-O-(2,6-dichlorobenzyl)-L-tyrosine;

The following compounds and pharmaceutically acceptable salts of them are preferred

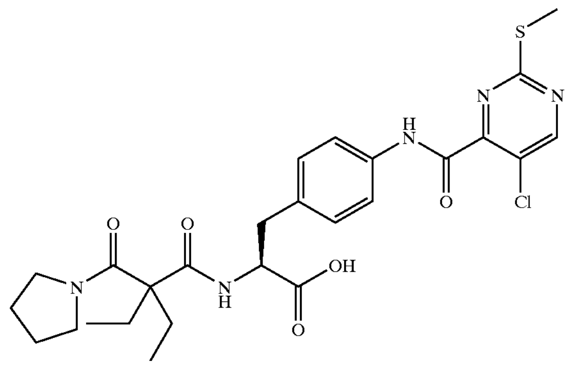

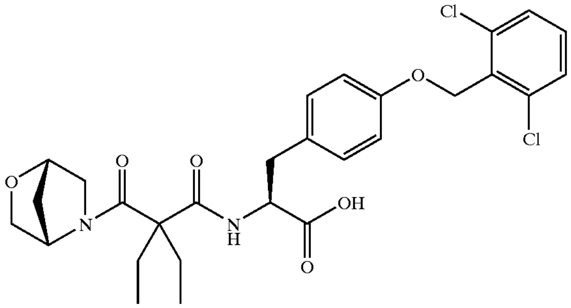

-continued

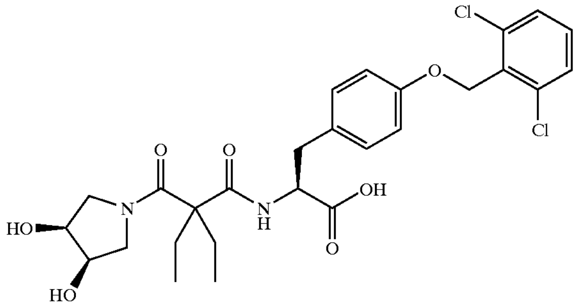

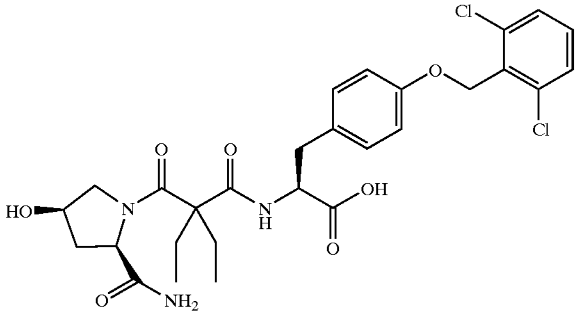

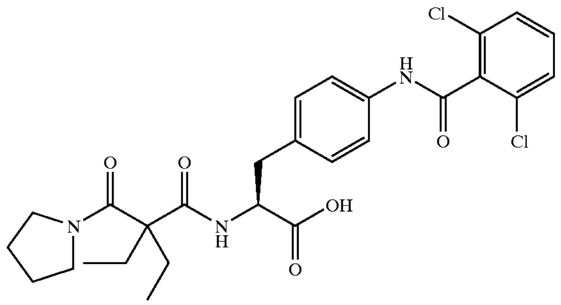

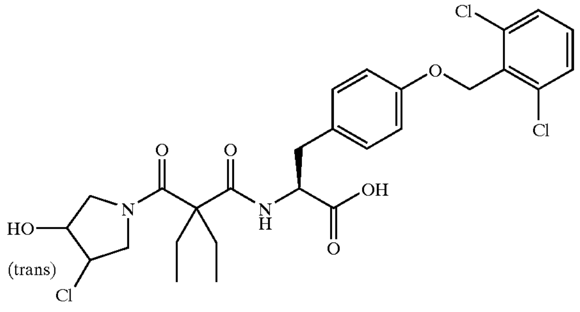

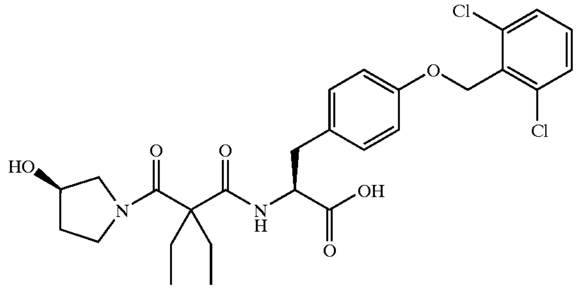

-continued
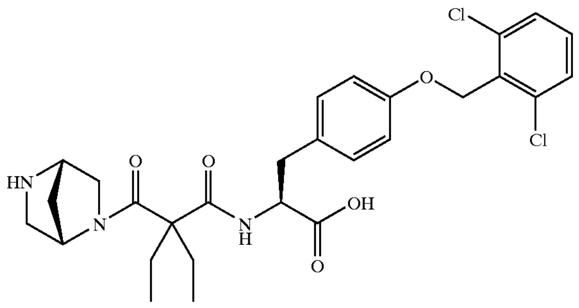
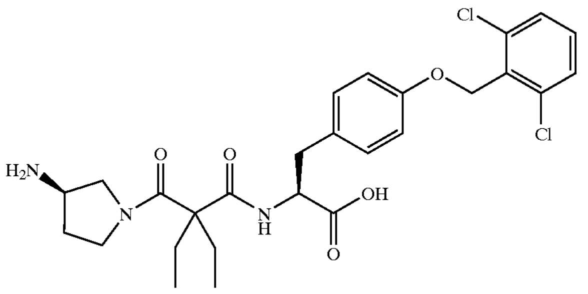
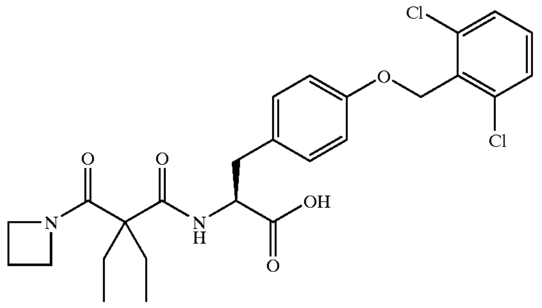
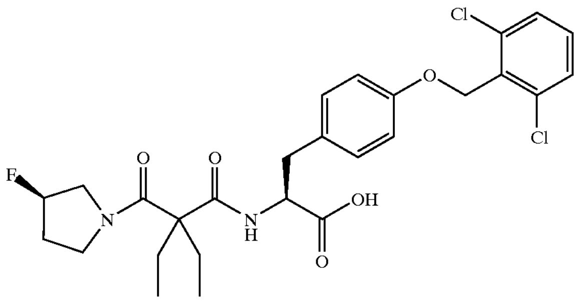
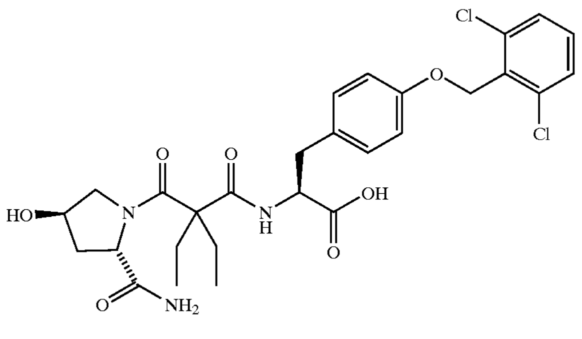
-continued
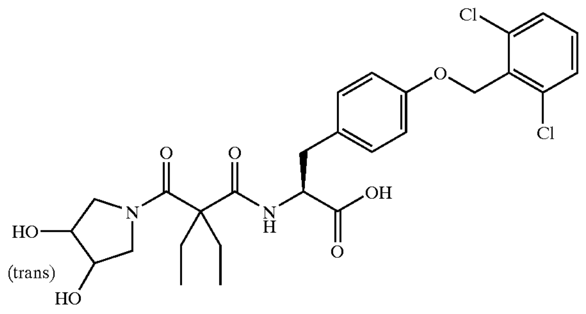
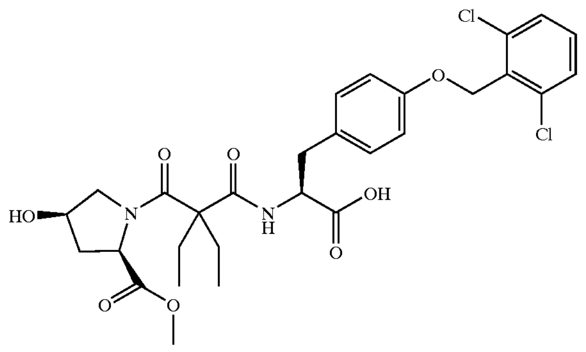
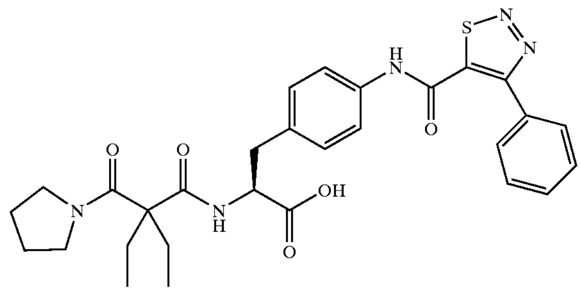
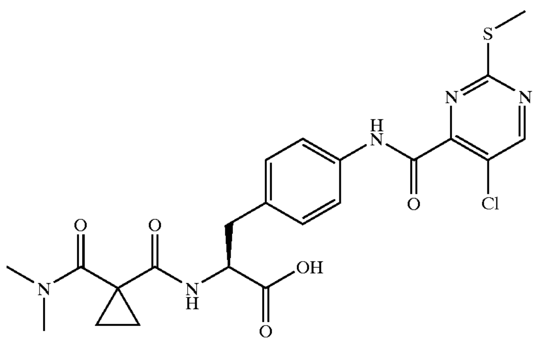
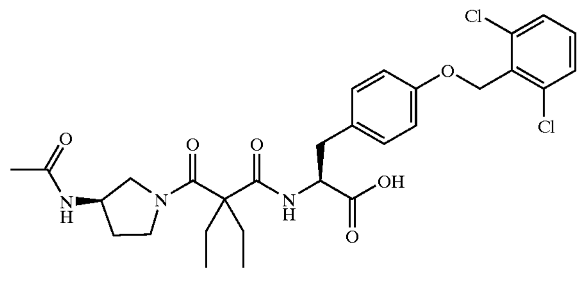

-continued

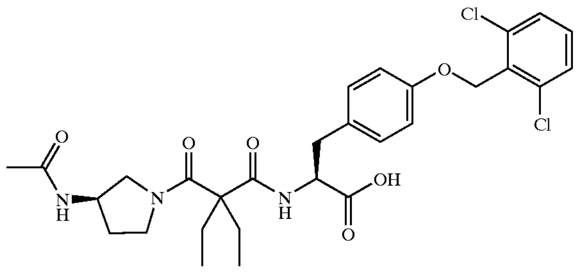

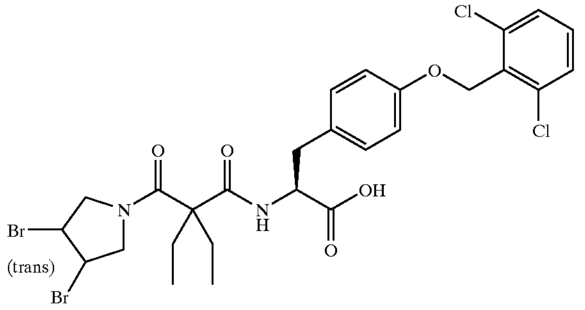

The following compounds and pharmaceutically acceptable salts of them are also preferred in the present invention.

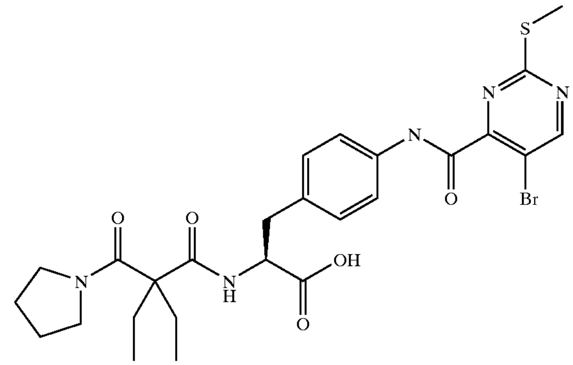

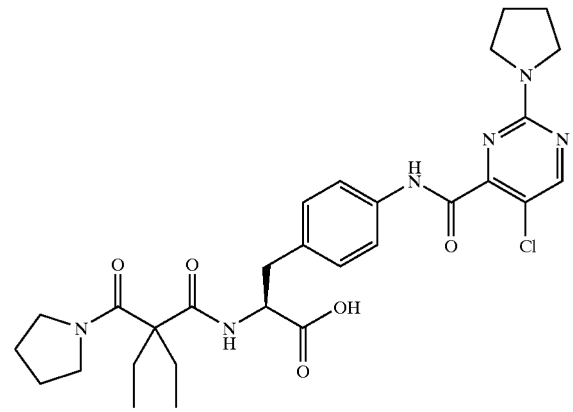

-continued

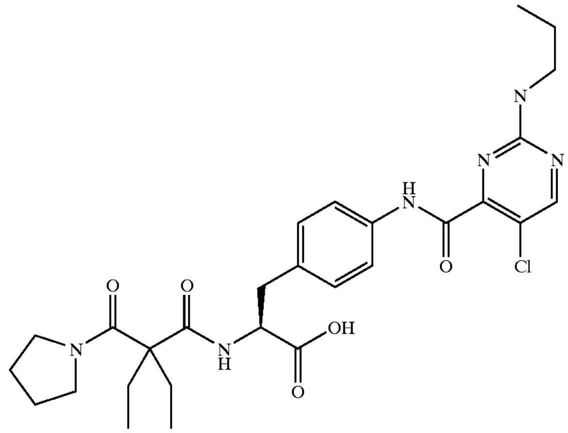

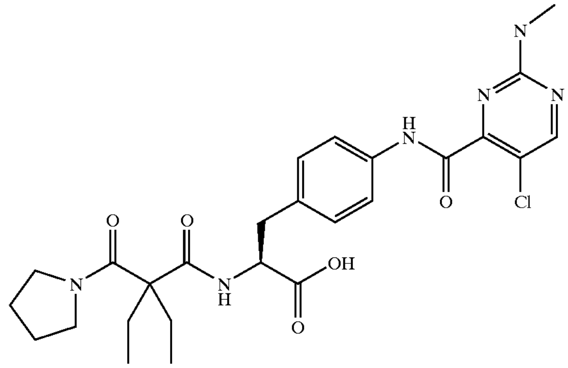

The phenylalanine derivatives (1) of the present invention can be synthesized by methods described below. For example, a phenylalanine derivative (9) of general formula (1) wherein —X—A represents a group defined by Q described below, Y represents a group of the formula: —C(═O)—, Z represents a group of the formula: —C(═O)—, B represents hydroxyl group and C represents hydrogen atom is synthesized as follows:

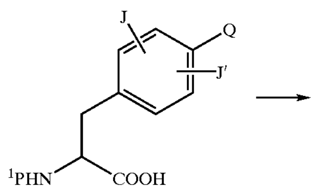

(3)

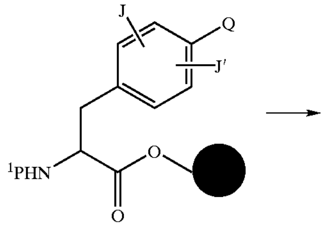

(4)

-continued

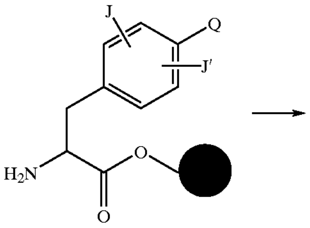

(5)

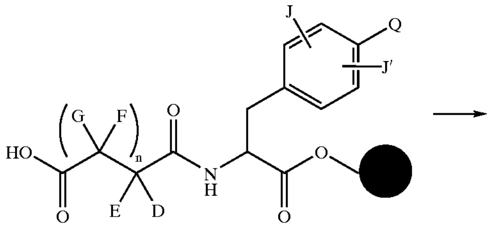

(6)

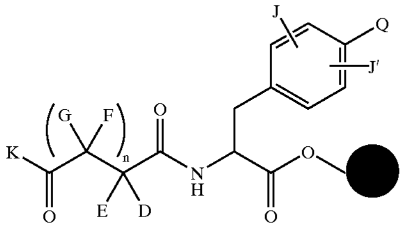

(7)

A suitably protected carboxylic acid (3) is introduced into a resin by a usual method. The substituent Q of the carboxylic acid (3) has a structure of —X—A as described above with reference to the general formula (1), it is a substituent which can be converted into —X—A in any stage of the synthesis or it is suitably protected form of these substituents. As for the introduction reaction conditions, the reaction can be conducted by using, if necessary, a suitable additive such as HOAt (1-hydroxy-7-azabenzotriazole) or HOBt (1-hydroxybenzotriazole) and a condensing agent such as DIC (diisopropylcarbodiimide), DCC (dicyclohexylcarbodiimide) or EDC (1-ethyl-3-(3-dimethylaminopropyl)carbodiimide) in an organic solvent such as dichloromethane, DMF (N,N-dimethylformamide) or NMP (N-methyl-2-pyrrolidone). For example, when Wang resin is used, the reaction is carried out in the presence of pyridine and 2,6-dichlorobenzoyl chloride in DMF to obtain an ester (4). The protective group P1 is removed from the ester (4) under suitable conditions to obtain an amine (5). For example, when Fmoc group (9-fluorenylmethoxycarbonyl group) is used as $P^1$, the protective group can be removed with a base such as piperidine in a solvent such as DMF. The amine (5) can be converted into a carboxylic acid (6) by condensing it with a suitable dicarboxylic acid by using a condensing agent such as DIC and, if necessary, a suitable additive such as HOAt or HOBt in an organic solvent such as DMF, NMP or dichloromethane. The carboxylic acid (6) can be converted into a carbonyl derivative (7) by reacting it with an amine, an alcohol, a hydrazine or a thiol under the same conditions as those in the above-described condensation reaction.

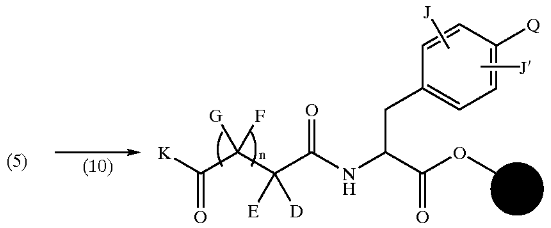

(8)

The amine (5) can be converted into a carbonyl derivative (8) by reacting it with a carboxylic acid (10), synthesized by a method described hereafter, under the above-described condensation reaction conditions.

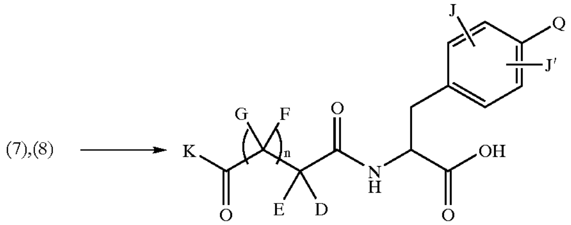

(9)

The carbonyl derivative (7) or the carbonyl derivative (8) obtained as described above is cleaved from the resin under suitable conditions to obtain a carboxylic acid (9). For example, when Wang resin is used as the resin, the product is treated with an acidic reaction solution containing, for example, TFA (trifluoroacetic acid) to obtain a carboxylic acid (9) solution and then the solvent is evaporated to obtain a carboxylic acid (9). The carboxylic acid (9) thus obtained is purified by the column chromatography, HPLC, recrystallization or the like to obtain a pure carboxylic acid (9).

The compounds of the general formula (1) can be synthesized also by the following method:

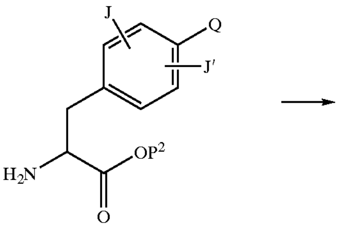

(11)

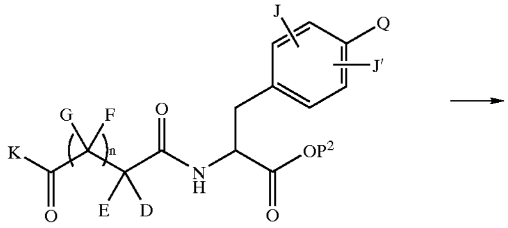

(12)

-continued

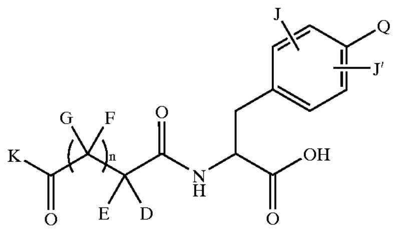

(9)

A suitably protected amine (11) is reacted with a carboxylic acid (10), synthesized by a method described hereafter, by using, if necessary, a suitable additive such as HOAt or HOBt and a condensing agent such as DIC, DCC or EDC in an organic solvent such as dichloromethane, DMF or NMP to obtain a carbonyl derivative (12). The substituent Q of the amine (11) has a structure of —X—A as described above with reference to the general formula (1), or it is a substituent which can be converted into —X—A in any stage of the synthesis or the substituent which is suitably protected. The protective group is removed from thus obtained carbonyl derivative (12) under suitable conditions to obtain the carboxylic acid (9). For example, the protective group can be removed by the alkali hydrolysis when $P^2$ is methyl or ethyl group, or by the treatment with an acidic solution when $P^2$ is t-butyl group or by the hydrolysis followed by the reaction with hydrogen in the presence of a metal catalyst when $P^2$ is benzyl group or the like.

The carboxylic acid (10) can be synthesized by the following method:

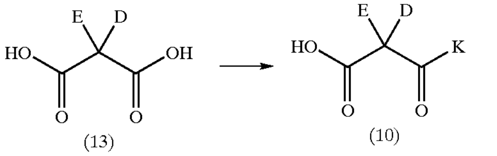

(13) (10)

Namely, a disubstituted malonic acid (13) is reacted with a suitable amount of an amine, an alcohol, a hydrazine or a thiol by using a suitable condensing agent such as DIC, DCC or EDC in the presence of a suitable additive in a suitable organic solvent such as dichloromethane or DMF and then the product is purified by a suitable method such as recrystallization to obtain the carboxylic acid (10).

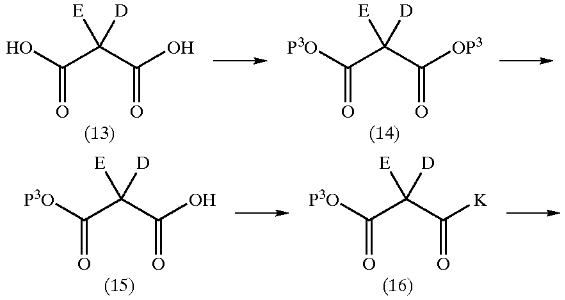

(13) (14) (15) (16)

-continued

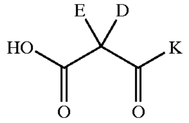

(10)

A monocarboxylic acid (15) can be obtained by esterifying the malonic acid (13) by an ordinary method to form a diester (14) and then reacting the diester (14) with a suitable amount of a base such as sodium hydroxide, potassium hydroxide or lithium hydroxide in an organic solvent such as methanol, ethanol or THF or in a mixed solvent of the organic solvent with water. The monocarboxylic acid (15) is reacted with suitable amount of an amine, an alcohol, a hydrazine or a thiol by using a suitable condensing agent such as DIC, DCC or EDC in the presence of a suitable additive in a suitable solvent such as dichloromethane or DMF to obtain a carbonyl derivative (16) and then this product is hydrolyzed under the same reaction conditions as those described above to obtain the carboxylic acid (10).

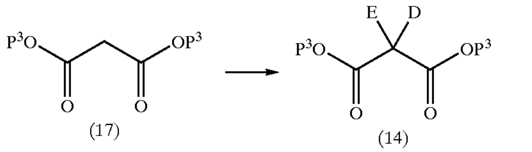

(17) (14)

The diester (14) can be obtained also by reacting a malonic diester (17) with an alkylating agent such as an alkyl halide or an alkyl sulfonate in the presence of a base such as a metal alkoxide or LDA in a solvent such as an alcohol, THF or an ether. It is also possible to obtain the diester (14) of the above formula wherein D is different from E by controlling the amount of the reagents and conducting the reaction in two steps:

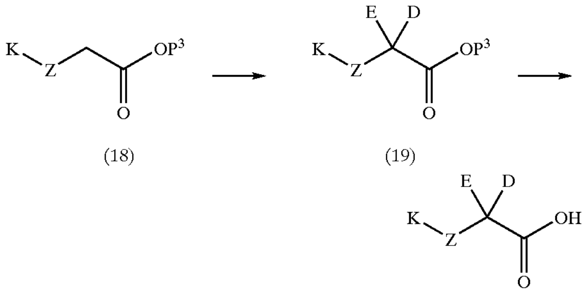

(18) (19) (10a)

When the group represented by K—Z is an acyl group and the group represented by Z is —S—, —S(=O)— or —$SO_2$—, an ester (19) can be obtained from a corresponding ester (18) under the same reaction conditions as those in the production of the diester (14) from the malonic diester (17). When the group represented by Z in the ester (19) is —S—, this group can be converted to —S(=O)— or —$SO_2$— by oxidization. The ester (19) can be converted to a carboxylic acid (10a) under the above-described hydrolysis conditions. It is also possible to synthesize a compound of the general formula (1) wherein Z represents —S—, —S(=O)— or —$SO_2$— by using a carboxylic acid (10a) by the same reaction as that for obtaining the carbonyl derivative (8) from the amine (5).

Various partial structures of —X—A in the general formula (1) can be synthesized from corresponding precursors by reactions described below. By the reactions described below, Q in the precursor structure can be converted into —X—A in a suitable stage in an ordinary method for synthesizing the compounds of the general formula (1).

When Q is hydroxyl group or a suitably protected hydroxyl group, the protective group is removed, if necessary, to form hydroxyl group and then the subsequent conversion reaction can be conducted as described below.

Hydroxyl group Q can be reacted with an alkylating agent such as an alkyl halide or an alkyl sulfonate in the presence of a suitable base in an organic solvent to form various ether-type structures. The ether-type compounds can be formed also by subjecting the obtained compound to Mitsunobu reaction with an alcohol in the presence of a dialkylazodicarboxylic acid. The compounds having structures of various aryl ether types or heteroaryl ether types can be formed by reacting the obtained compound with an aryl halide, a heteroaryl halide, an arylboronic acid or a heteroarylboronic acid in the presence of a suitable base or catalyst in an organic solvent.

Hydroxyl group Q can be reacted with a sulfonic acid halide or sulfonic acid anhydride in the presence of an organic base such as triethylamine, diisopropylethylamine, pyridine or N,N-dimethylaminopyridine or an inorganic base such as potassium carbonate or sodium carbonate in an organic solvent such as DMF or dichloromethane to form a corresponding product having a sulfonic acid ester structure.

A trifluoromethanesulfonic acid ester (hereinafter referred to as "triflate" can be obtained under the above-described sulfonation reaction conditions. The triflate can be converted into an aryl-substituted compound or a heteroaryl-substituted compound by Suzuki coupling reaction wherein it is reacted with a various boric acid in the presence of a palladium catalyst such as tetrakistriphenylphosphine palladium or palladium acetate or another metal catalyst in a solvent such as DMF DME (1,2-dimethoxylethane), toluene or dioxane at room temperature or an elevated temperature. The conversion reaction into the aryl-substituted compounds can be carried out by using not only the triflate but also a compound of the above formula wherein Q is substituted with a halogen atom.

When Q is a properly protected amino group, the protective group can be removed to form the amino group by a method suitably selected depending on the protective group. When Q is nitro group, it can be converted into the amino group by the hydrogenation reaction in the presence of a metal catalyst or by the reduction reaction with a reducing agent selected from among various reducing agents. The amino group thus obtained can be further converted into groups of various structures by various reactions described below.

The amino group can be further converted into an alkylamino group by reacting it with an alkylating agent such as an alkyl halide or an alkyl sulfonate in the presence of a suitable base in an organic solvent. Various arylamine structures can be formed by reacting the amino group with an aryl halide in the presence of a suitable base in an organic solvent.

The amino group can be converted into an alkylamino group by reacting it with an aldehyde or a ketone in the presence of a reducing agent such as sodium borohydride or sodium cyanoborohydride in a solvent such as DMF, dichloromethane, a trialkylorthoformic acid or a trialkylorthoacetic acid. The amino group or alkylamino group can be converted into groups of various structures by reactions described below.

The amino group or alkylamino group can be converted into a corresponding structure of amide type or sulfonamide type by reacting it with a carboxylic acid halide, a carboxylic acid anhydride, a sulfonic acid halide or a sulfonic acid anhydride in the presence of an organic base such as triethylamine, diisopropylethylamine, pyridine or N,N-dimethylaminopyridine or an inorganic base such as potassium carbonate or sodium carbonate in an organic solvent such as DMF or dichloromethane. The amino group or alkylamino group can be converted into a corresponding structure of amide type also by reacting it with a carboxylic acid in the presence of a suitable additive and condensing agent in an organic solvent such as DMF or dichloromethane.

The amino group or alkylamino group can be converted into a corresponding structure of urea type or thiourea type by reacting it with an isocyanate or an isothiocyanate in the presence of, if necessary, an organic base such as triethylamine, diisopropylethylamine, pyridine or N,N-dimethylaminopyridine in an organic solvent such as DMF, toluene or dichloromethane.

The amino group can be converted into a corresponding structure of amide type by reacting it with a properly protected aminocarboxylic acid in the presence of suitable additive and condensing agent in a suitable organic solvent such as DMF or dichloromethane or by reacting it with a properly protected aminocarboxylic acid halide in the presence of a suitable base. After removing the protective group, the obtained compound can be reacted with 1,1-carbonyldiimidazole or trimethyl o-formate to obtain the ring-closed compound. The ring-closed compound can be converted into an N-alkylated ring-closed compound by alkylating it under suitable conditions.

The product having the sulfonamide structure formed as described above can be alkylated by the above-described Mitsunobu reaction with an alcohol. The alkylation reaction can be carried out also by reacting the compound with an alkylating agent such as an alkyl halide or an alkyl sulfonate in the presence of a suitable base in an organic solvent. When an isocyanate or isothiocyanate having a leaving group at a proper position is used in the formation of the product having the urea-type or thiourea-type structure, a ring-closed compound can be obtained by treating the formed urea-type or thiourea-type compound with a base or the like. The compound can be further N-alkylated under suitable conditions.

Optical isomers of the phenylalanine derivatives represented by the general formula (1) in the present invention are possible because they have an asymmetric carbon atom. The compounds of the present invention also include those optical isomers. When the compounds have diastereomers, the diastereomers and a diastereomer mixture are also included in the present invention. Various tautomers of the phenylalanine derivatives of the general formula (1) are possible in the present invention because they contain exchangeable hydrogen atoms. The compounds of the present invention also include those tautomers. The carboxyl group in the compounds of the present invention may be substituted with a substituent which can be converted to form the carboxyl group in vivo.

When the compounds of general formula (1) can form salts thereof, the salts are pharmaceutically acceptable ones. When the compound has an acidic group such as carboxyl group, the salts can be ammonium salts, or salts thereof with alkali metals, e.g. sodium and potassium, salts thereof with alkaline earth metals, e.g. calcium and magnesium, salts thereof with aluminum and zinc, salts thereof with organic amines, e.g. triethylamine, ethanolamine, morpholine, piperidine and dicyclohexylamine, and salts thereof with basic amino acids, e.g. arginine and lysine. When the compound has a basic group, the salts can be those with inorganic acids, e.g. hydrochloric acid, sulfuric acid and phosphoric acid; those with organic acids, e.g. acetic acid, citric acid, benzoic acid, maleic acid, fumaric acid, tartaric acid and succinic acid; and those with organosulfonic acids, e.g. methanesulfonic acid and p-toluenesulfonic acid. The salts can be formed by mixing a compound of the general formula (1) with a necessitated acid or base in a proper ratio in a solvent or dispersing agent or by the cation exchange or anion exchange reaction with another salt.

The compounds of the general formula (1) of the present invention include also solvates thereof such as hydrates and alcohol adducts thereof.

The compounds of general formula (1) and salts thereof are administered as they are or in the form of various medicinal compositions to patients. The dosage forms of the medicinal compositions are, for example, tablets, powders, pills, granules, capsules, suppositories, solutions, sugar-coated tablets, depots and syrups. They can be prepared with ordinary preparation assistants by an ordinary method.

For example, the tablets are prepared by mixing the phenylalanine derivative, the active ingredient of the present invention, with any of known adjuvants such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; corrigents, e.g. peppermint, Akmono (Gaultheria aderothrix) Oil and cherry; lubricants, e.g. magnesium stearate, talc and carboxymethyl cellulose; excipients for soft gelatin capsules and suppositories, e.g. fats, waxes, semi-solid or liquid polyols, natural oils and hardened oils; and excipients for solutions, e.g. water, alcohols, glycerols, polyols, sucrose, invert sugars, glucose and vegetable oils.

The antagonist containing one of the compounds of above general formula (1) or one of salts thereof as active ingredient is usable as a therapeutic agent or preventing agent for diseases in which α 4 integrin-depending adhesion process participates in the pathology, such as inflammatory diseases, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis, transplantation rejection, etc.

The dose of the compound of general formula (1) or salt thereof used for the above-described purpose varies depending on the intended therapeutic effect, administration method, period of the treatment, and age and body weight of the patient. The dose is usually 1 μg to 5 g a day for adults in the oral administration, and 0.01 μg to 1 g a day for adults in the parenteral administration.

The following Examples will further illustrate the present invention, which are only preferred embodiments of the invention and which by no means limit the invention.

EXAMPLE 1

Preparation of Resin 3.0 g of Wang resin (0.87 mmol/g) was suspended in DMF, and the obtained suspension was left to stand at room temperature for 3 hours. The superfluous solvent was removed, and the rest was added to a solution of 4.4 g of Fmoc-Tyr-(2,6-dichlorobenzyl)-OH, 1.2 ml of 2,6-dichlorobenzoyl chloride and 1.2 ml of pyridine in 30 ml of DMF, and the resultant mixture was shaken at room temperature for 20 hours. The superfluous solvent was removed, and the resin was washed with 30 ml of DMF twice. The obtained resin was treated with 20% solution of piperidine in DMF at room temperature for 3 hours. The solvent was removed, and the residue was washed with 30 ml of each of DMF and dichloromethane 3 times. The obtained resin was used for the subsequent reaction.

EXAMPLE 2

Synthesis of N-[2-(dimethylaminocarbonyl)-2-methyl-propanoyl]-O-(2,6-dichlorobenzyl)-L-tyrosine 30 mg of the resin obtained in Example 1 was added to a solution of 160 mg of dimethylmalonic acid, 140 mg of HOAt, 150 μl of DIC and 1.5 ml of DMF to conduct the reaction at room temperature for 20 hours. The solution was removed and the remaining resin was washed with DMF twice and added to a mixture of 0.5 ml of 2M dimethylamine solution in THF, 140 mg of HOAt and 150 μl of DIC in 1.0 ml of DMF and reacted for 20 hours. The reaction solution was removed, and the resin was washed with DMF, dichloromethane and ether 3 times each. The resin was treated with 95% aqueous trifluoroacetic acid solution for 1 hour. The resin was removed by the filtration and then washed with acetonitrile. The wash solutions were combined together, concentrated and purified by the reversed-phase HPLC [Inertsil ODS column, developer: water/acetonitrile (TFA 0.05%)] to obtain 4.3 mg of the intended compound.

MS (ESI positive): 481, 483, 485

[$C_{23}H_{26}N_2O_5Cl_2$: 480, 482, 484]

EXAMPLES 3 TO 9, 32–78, 80, 84, 450–457 AND 459 TO 475

The same procedure as that of Example 2 was repeated except that the resin prepared in Example 1 and a dicarboxylic acid and an amine were used to obtain the compounds shown in Table 1.

EXAMPLES 10 TO 31

The same procedure as that of Example 2 was repeated except that the resin prepared in Example 1 and a dicarboxylic acid and an amine were used and that HPLC purification was omitted to obtain the compounds shown in Table 2.

D, E and K in Tables 1 and 2 are substituents in general formula (1-1) given below.

EXAMPLE 79

Synthesis of N-(2-{[(trans-3,4-dibromopyrrolidine)-1-yl]carbonyl}-2-ethyl-butanoyl)-O-(2,6-dichlorobenzyl)-L-tyrosine 20 mg of a resin obtained in step 1 in Example 83 which will be described below was reacted with 600 mg of tetrabutylammonium tribromide and 2 ml of DCM for 4 days, and the reaction product was washed with DMF and DCM 3 times each and then dried under reduced pressure. After treating the resin with 1.5 ml of 95% aqueous trifluoroacetic acid solution for 1 hour, the filtrate was concentrated under reduced pressure and then purified by the reversed-phase HPLC [Inertsil ODS column, developer: water/acetonitrile (TFA 0.05%)] to obtain 10 mg of the intended compound.

MS (ESI positive): 691, 693, 695

$C_{27}H_{30}Br_2Cl_2N_2O_5$: 690, 692, 694

EXAMPLE 81

Synthesis of N-(2-{[(cis-3,4-dihydroxypyrrolidine)-1-yl]carbonyl}-2-ethyl-butanoyl)-O-(2,6-dichlorobenzyl)-L-tyrosine 20 mg of the resin obtained in step 1 in Example 83 was reacted with 40 mg of $OsO_4$ and 2 ml of dioxane for 16 hours, and then washed with each of DMF, DCM and DMF repeatedly 3 times. The resin was treated with a solution of 0.2 g of $NaHSO_3$ in a mixed solvent of water (1 ml) and methanol (1 ml), then washed with each of $H_2O$, MeOH, DMF and DCM repeatedly 3 times and then dried under reduced pressure. After treating the product with 1.5 ml of trifluoroacetic acid containing 5% of water for 1 hour, the filtrate was concentrated under reduced pressure and then purified by the reversed-phase HPLC [Inertsil ODS column, developer: water/acetonitrile (TFA 0.05%)] to obtain 0.9 mg of the intended compound.

MS (ESI positive): 567

$C_{27}H_{32}Cl_2N_2O_7$: 566

EXAMPLE 82

Synthesis of N-(2-{[(trans-3-hydroxy-4-chloropyrrolidine)-1-yl]carbonyl})-2-ethyl-butanoyl]-O-(2,6-dichlorobenzyl)-L-tyrosine:

1 M solution (1.5 ml) of HCl in dioxane was added to 10 mg of the resin obtained in step 2 in Example 83, and they were reacted for 1 hour. The filtrate was concentrated under reduced pressure and then purified by the reversed-phase HPLC [Inertsil ODS column, developer: water/acetonitrile (TFA 0.05%)] to obtain 0.9 mg of the intended compound.

MS (ESI positive): 585

$C_{27}H_{31}Cl_3N_2O_6$: 584

EXAMPLE 83

Synthesis of N-(2-{[(trans-3,4-dihydroxypyrrolidine)-1-yl]carbonyl}-2-ethyl-butanoyl)-O-(2,6-dichlorobenzyl)-L-tyrosine Step 1 Preparation of Resin 1.5 g of the resin (H-Tyr(2,6-dichlorobenzyl)-O-Wang) obtained by the method of Example 1 was added to a solution of 2.9 g of diethylmalonic acid, 7.45 g of HOAt, 8.4 ml of DIC and 24 ml of NMP to conduct the reaction at room temperature for 16 hours. The reaction solution was removed, and the resin was washed with DMF 5 times. After carrying out the reaction in a solution of 766 μl of pyrroline, 1.37 g of HOAt and 1.5 ml of DIC in 15 ml of NMP for 16 hours, the reaction solution was removed, and the resin was washed with each of DMF and DCM repeatedly 3 times and then dried under reduced pressure.

Step 2 Oxidation of Double Bond 20 mg of the resin obtained in step 1 was washed with DCM 3 times and then reacted with 698 mg of mCPBA for 4 days. The reaction solution was removed, and the resin was washed with DCM 5 times and then dried under reduced pressure.

Step 3 Removal of Resin

The resin obtained in step 2 was treated with 1.5 ml of 95% aqueous trifluoroacetic acid solution for 1 hour. The filtrate was concentrated under reduced pressure and then purified by the reversed-phase HPLC [Inertsil ODS column, developer: water/acetonitrile (TFA 0.05%)] to obtain 7.0 mg of the intended compound.

MS (ESI positive): 567

$C_{27}H_{13}Cl_{12}N_2O_7$: 566

TABLE 1

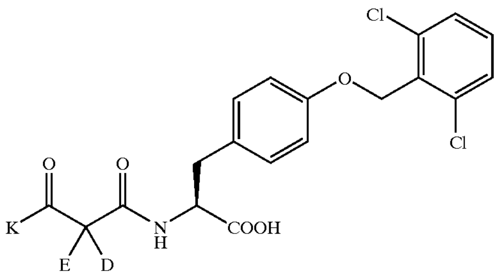

| Example | D | E | K | MS Found (MH+) |
|---|---|---|---|---|
| 3 | Et | Et | Me2N | 509, 511, 513 |
| 4 | Et | Et | PhNH | 557, 559, 561 |
| 5 | Et | Et | (4-HOPh)NH | 573, 575, 577 |
| 6 | Et | Et | (4-HOPh)CH2CH2NH | 601, 603, 605 |
| 7 | Et | Et | (4-HOPh)piperazino | 642, 644, 646 |
| 8 | | —(CH2)4— | Me2N | 507, 509, 511 |
| 9 | | —(CH2)4— | (4-HOPh)piperazino | 640, 642, 644 |
| 32 | Et | Et | Pyrrolidino | 535, 537, 539 |
| 33 | Me | Me | Pyrrolidino | 507, 509, 511 |
| 34 | Et | Et | Morpholino | 551, 553, 555 |
| 35 | Et | Et | (R)-3-Hydroxypyrrolidino | 551, 553, 555 |
| 36 | Et | Et | Thiomorpholino | 567, 569, 571 |
| 37 | Et | nPr | Pyrrolidino | 549, 551, 553 |
| 38 | Me | Et | Pyrrolidino | 521, 523, 525 |
| 39 | Et | Et | 4-(Aminocarbonyl)piperidino | 592, 594, 596 |
| 40 | Et | Et | Me2NCH2CH2NMe | 566, 568, 570 |
| 41 | Et | Et | EtMeN | 523, 525, 527 |
| 42 | Et | Et | Homopiperazino | 564, 566, 568 |
| 43 | Et | MeOCH2CH2 | Pyrrolidino | 565, 567, 569 |
| 44 | Et | Et | (R)-3-Dimethylaminopyrrolidino | 578, 580, 582 |
| 45 | Et | Et | 4-Formylpiperazino | 578, 580, 582 |
| 46 | Et | Et | (2S,4R)-4-Hydroxy-2-methoxy-carbonylpyrrolidino | 609, 611, 613 |
| 47 | Et | Et | (R,S)-3-Aminopyrrolidino | 550, 552, 554 |
| 48 | Et | Et | (R,S)-3-Hydroxypiperidino | 565, 567, 569 |
| 49 | Et | Et | (R,S)-4-Hydroxypiperidino | 565, 567, 569 |

TABLE 1-continued

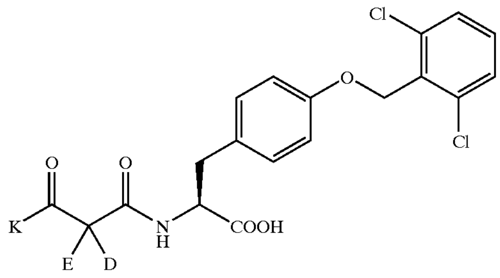

| Example | D | E | K | MS Found (MH+) |
|---|---|---|---|---|
| 50 | Et | Et | (S)-2-(Methoxymethyl)pyrrolidino | 579, 581, 583 |
| 51 | Et | Et | (R,S)-2-(Aminocarbonyl)piperidino | 591, 593, 595 |
| 52 | Et | Et | partial structure 1 | 562, 564, 56 |
| 53 | Et | Et | (S)-2-(Pyrrolidinomethyl)-pyrrolidino | 618, 620, 622 |
| 54 | Et | Et | (R)-3-(Acetylamino)pyrrolidino | 592, 594, 596 |
| 55 | Et | Et | (S)-3-(Acetylamino)pyrrolidino | 592, 594, 596 |
| 56 | Et | Et | (R)-2-(Methoxycarbonyl)pyrrolidino | 593, 595, 597 |
| 57 | Et | Et | [3(R,S),5(R,S)]-3,5-Dimethylmorpholino | 579, 581, 583 |
| 58 | —(CH2)2—O—(CH2)2— | | Pyrrolidino | 549, 551, 553 |
| 59 | —(CH2)2— | | 3-Oxopyrrolidino | 519, 521, 523 |
| 60 | Et | Et | (R,S)-3-(Hydroxymethyl)piperidino | 79, 581, 583 |
| 61 | Et | Et | 4-Formylhomopiperazino | 592, 594, 596 |
| 62 | Et | Et | partial structure 2 | 533, 536, 537 |
| 63 | Et | Et | (R)-3-(Trifluoromethylcarbonyl-amino)pyrrolidino | 646, 648, 650 |
| 64 | Et | Et | (R)-3-(Methylamino)pyrrolidino | 564, 566, 568 |
| 65 | Et | Et | (S)-3-Hydroxypyrrolidino | 551, 553, 555 |
| 66 | Et | Et | (S)-3-Aminopyrrolidino | 550, 552, 554 |
| 67 | Et | Et | (S)-2-(Aminocarbonyl)pyrrolidino | 578, 580, 582 |
| 68 | Et | Et | (2R,4R)-4-Hydroxy-2-methoxy-carbonylpyrrolidino | 609, 611, 613 |
| 69 | Et | Et | 3-Oxopyrrolidino | 549, 551, 553 |
| 70 | Et | Et | (R)-2-(Aminocarbonyl)pyrrolidino | 578, 580, 582 |
| 71 | Et | Et | (2R,4R)-2-Aminocarbonyl-4-hydroxypyrrolidino | 594, 596, 598 |
| 72 | Et | Et | (S)-2-(Methylaminocarbonyl)-pyrrolidino | 592, 594, 596 |
| 73 | Et | Et | (2S,4R)-2-Aminocarbonyl-4-hydroxypyrrolidino | 594, 596, 598 |
| 74 | Et | Et | partial structure 3 | 563, 565, 567 |
| 75 | Et | Et | partial structure 4 | 579, 581, 583 |
| 76 | Et | Et | (R)-3-Aminopyrrolidino | 550, 552, 554 |
| 77 | Et | Et | (R)-3-Hydroxypiperidino | 565, 567, 569 |
| 78 | Et | Et | Azetidino | 521, 523, 525 |
| 79 | Et | Et | trans-3,4-Dibromopyrrolidino | 691, 693, 695 |
| 80 | Et | Et | (S)-3-Fluoropyrrolidino | 553, 555, 557 |
| 81 | Et | Et | cis-3,4-Dihydroxypyrrolidino | 567 |
| 82 | Et | Et | trans-3-Chloro-4-hydroxypyrrolidino | 585 |
| 83 | Et | Et | trans-3,4-Dihydroxypyrrolidino | 567 |
| 84 | Et | Et | (R)-3-Fluoropyrrolidino | 553, 555, 557 |
| 450 | Et | 3-Methylbutyl | Pyrrolidino | 577, 579, 581 |
| 451 | Allyl | Allyl | Pyrrolidino | 559, 561, 563 |
| 452 | Et | Benzyl | Pyrrolidino | 597, 599, 601 |
| 453 | Et | Cyclopentyl | Pyrrolidino | 575, 577, 579 |
| 454 | Et | Butyl | Pyrrolidin | 563, 565, 567 |
| 455 | nPr | MeOCH2CH | Pyrrolidino | 579, 581, 583 |
| 456 | Me | MeOCH2CH2 | Pyrrolidino | 551, 553, 555 |
| 457 | Butyl | MeOCH2CH2 | Pyrrolidino | 593, 595, 597 |
| 459 | Et | Et | (R)-2-(Benzyloxycarbonyl)pyrrolidino | 669 |
| 460 | Et | Et | (S)-2-(Dimethylaminocarbonyl)pyrrolidino | 606 |
| 461 | —$(CH_2)_3$— | | partial structure 4-1 | 565 |
| 462 | —$(CH_2)_3$— | | partial structure 4-2 | 641 |
| 463 | —$(CH_2)_3$— | | 4-Formylpiperazino | 562 |
| 464 | Et | Et | 4-Acetylpiperazino | 592 |
| 465 | Et | Et | 4-Formylhomopiperazino | 606 |
| 466 | Et | Et | partial structure 4-3 | 604 |
| 467 | —$(CH_2)_2$—O—$(CH_2)_2$— | | (R)-3-Hydroxypyrrolidino | 565 |
| 468 | —$(CH_2)_2$—O—$(CH_2)_2$— | | Me2N | 523 |
| 469 | —$(CH_2)_2$—O—$(CH_2)_2$— | | partial structure 4-4 | 611 |
| 470 | —$(CH_2)_2$—O—$(CH_2)_2$— | | partial structure 4-5 | 631 |
| 471 | —$(CH_2)_2$—O—$(CH_2)_2$— | | partial structure 4-6 | 631 |
| 472 | —$(CH_2)_2$—O—$(CH_2)_2$— | | partial structure 4-7 | 631 |
| 473 | —$(CH_2)_2$—O—$(CH_2)_2$— | | partial structure 4-8 | 643 |

TABLE 1-continued
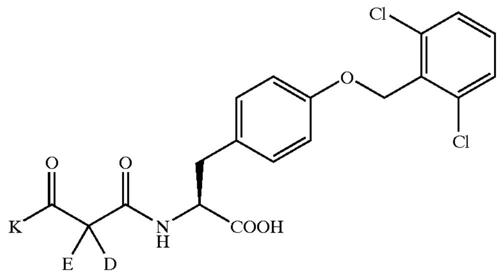
| Example | D | E | K | MS Found (MH+) |
|---|---|---|---|---|
| 474 | $—(CH_2)_2—O—(CH_2)_2—$ | | partial structure 4-9 | 629 |
| 475 | $—(CH_2)_2—O—(CH_2)_2—$ | | partial structure 4-10 | 669 |
In the table, 4-HOPh represents 4-hydroxyphenyl (the same shall apply hereinafter).
Partial Structures
TABLE 2
1
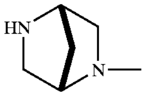
2
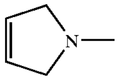
3
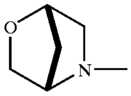
4
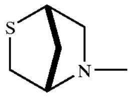
4-1
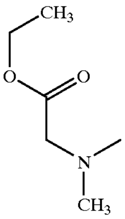
4-2
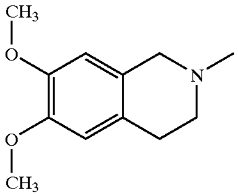
4-3
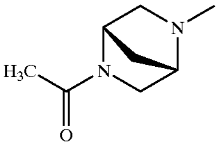
TABLE 2-continued
4-4
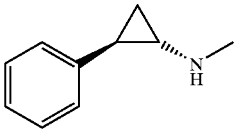
4-5
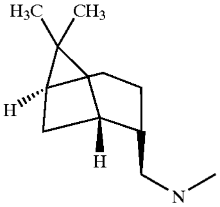
4-6
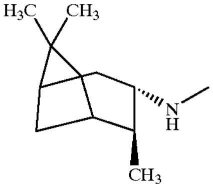
4-7
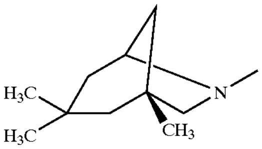
4-8
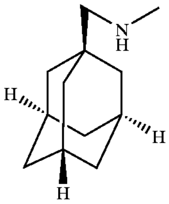
4-9
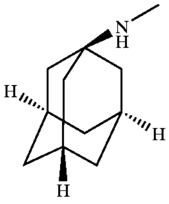

TABLE 2-continued

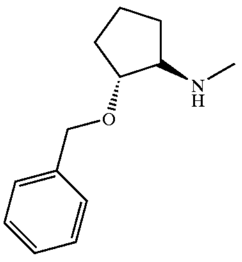

4-10

| Example | D | B | K | MS Found (MH+) |
|---|---|---|---|---|
| 10 | Me | Me | nBuNH | 509, 511, 513 |
| 11 | Me | Me | iBuNH | 509, 511, 513 |
| 12 | Me | Me | BnNH | 543, 545, 547 |
| 13 | Me | Me | PhNH | 529, 531, 533 |
| 14 | Me | Me | (4-HOPh) NH | 545, 547, 549 |
| 15 | Et | Et | cHexNH | 563, 565, 567 |
| 16 | Et | Et | BnNH | 571, 573, 575 |
| 17 | Et | Et | 1-Piperidino | 549, 551, 553 |
| 18 | —(CH2)2— | | iBuNH | 507, 509, 511 |
| 19 | —(CH2)2— | | tBuNH | 507, 509, 511 |
| 20 | —(CH2)2— | | BnNH | 541, 543, 545 |
| 21 | —(CH2)2— | | Me2N | 479, 481, 483 |
| 22 | —(CH2)2— | | PhNH | 527, 529, 531 |
| 23 | —(CH2)2— | | PhMeN | 541, 543, 545 |
| 24 | —(CH2)2— | | (4-HOPh) NH | 543, 545, 547 |
| 25 | —(CH2)2— | | PhNHNH | 542, 544, 546 |
| 26 | —(CH2)3— | | iBuNH | 521, 523, 525 |
| 27 | —(CH2)3— | | tBuNH | 521, 523, 525 |
| 28 | —(CH2)3— | | BnNH | 555, 557, 559 |
| 29 | —(CH2)3— | | Me2N | 493, 495, 497 |
| 30 | —(CH2)3— | | PhNH | 541, 543, 545 |
| 31 | —(CH2)3— | | (4-HOPh) NH | 557, 559, 561 |

EXAMPLE 85

Synthesis of N-[1-N,N-dimethylaminocarbonyl-cyclopropane-1-ylcarbonyl]-4-({[5-chloro-2-(methylthio)pyrimidine-4-yl]carbonyl}-amino)-L-phenylalanine Step 1 Introduction of Amino Acid into Resin 2.0 g of Wang resin (0.76 mmol/g) was alternately washed with NMP and DCM twice and then with NMP 3 times. A solution (11 ml) of 2.0 g of Fmoc-Phe(4-nitro)-OH in NMP, a solution (5 ml) of 0.87 ml of pyridine in NMP and a solution (4 ml) of 0.66 ml of 2,6-dichlorobenzoyl chloride in NMP were successively added to the resin, and the obtained mixture was shaken at room temperature for 16 hours. The reaction solution was removed, and the resin was washed with DMF 3 times, with ethanol 3 times, with DCM 3 times and with NMP 3 times. 7 ml of NMP, 7 ml of a solution of 1.49 ml of pyridine in NMP and 7 ml of a solution of 1.46 ml of acetic anhydride in NMP were added to the obtained resin. After shaking at room temperature for 2 hours, the reaction solution was removed, and the residue was washed with DMF 3 times, with ethanol 3 times and with DCM 3 times. The obtained resin was dried under reduced pressure.

Step 2 Fmoc-Removing Reaction 42 ml of 20% solution of piperidine in DMF was added to the resin obtained as described above, and they were shaken for 5 minutes. The reaction solution was removed, 42 ml of 20% solution of piperidine in DMF was added again to the residue, and they were shaken for 15 minutes. The reaction solution was removed, and the resin was washed with DMF 3 times, with ethanol 3 times, with DCM 3 times, and again with DMF 3 times.

Step 3 Acylation/Amidation Reaction

A solution (12 ml) of 1.96 g of cyclopropanedicarboxylic acid in DMF, a solution (17 ml) of 2.05 g of HOAt in DMF and 2.29 ml of DIC were successively added to the resin obtained in step 2. After shaking at room temperature for 3.5 hours, the reaction solution was removed, and the resin was washed with DMF 3 times, DCM 3 times and again with DMF 3 times. A solution obtained by diluting 2M-THF solution (7.57 ml) of dimethylamine with 12 ml of DMF was added to the resin. A solution (17 ml) of 2.05 g of HOAt and 2.29 ml of DIC was added to the obtained mixture, and they were shaken at room temperature for 15 hours. The reaction solution was removed, and the residue was washed with DMF 3 times, with ethanol 3 times and with DCM 3 times. The obtained resin was dried under reduced pressure.

Step 4 Reduction of Nitro Group

The resin obtained in step 3 was added to 50 ml of 2 M solution of stannic chloride dihydrate in DMF to conduct the reaction at room temperature for 3 hours. The reaction solution was removed, and the residue was washed with DMF, ethanol and DCM 3 times each. The obtained resin was dried under reduced pressure.

Step 5 Acylation Reaction

A solution (200 μl) of 13.5 mg of 5-chloro-2-(methylthio)-pyrimidine-4-carboxylic acid in DMF, a solution (157 μl) of 34.3 mg of PyBOP in DMF, a solution (157 μl) of 14.9 mg of HOBt in DMF and a solution (157 μl) of 23.0 μl of DIEA in DMF were successively added to 40.0 mg of the resin obtained in step 4, and they were shaken at room temperature for 23 hours. The reaction solution was removed, and the residue was washed with DMF, ethanol and DCM 3 times each.

Step 6 Removal of Resin

95% aqueous trifluoroacetic acid solution (1 ml) was added to the resin obtained in step 5, and they were shaken for 1 hour and then filtered. 95% aqueous trifluoroacetic acid solution (1 ml) was added to the resin, and they were shaken for 1 hour and then filtered. The filtrates were combined together and then concentrated. After the purification by the reversed-phase HPLC [Symmetry C18 column (5 μm; 19 mmϕ×50 mm) of Waters Co., developer: water/acetonitrile (TFA 0.05%)], 4.8 mg of the intended compound was obtained.

MS (ESI positive): 506

$C_{22}H_{24}ClN_5O_5S$: 505

EXAMPLES 86 TO 89 AND 106 TO 107

Compounds in the respective Examples were synthesized in the same manner as that of Example 85 except that a corresponding carboxylic acid was used in place of 5-chloro-2-(methylthio)pyrimidine-4-carboxylic acid used in step 5 in Example 85. D, E, K and L in Table 2-1 were substituents in general formula (1-2) given below. See Table 2-1.

EXAMPLE 90

Synthesis of N-[1-(N,N-dimethylaminocarbonyl)-cyclopropane-1-ylcarbonyl]-4-{[2,6-dichlorophenyl-carbonyl]amino}-L-phenylalanine Step 1 Acylation Reaction A solution (250 μl) of 12.2 μl of pyridine in DCM and a solution (200 μl) of 13.5 μl of 2,6-dichlorobenzoyl chloride in DCM were added to 51.2 mg of the resin obtained in step 4 in Example 85. After shaking at room temperature for 15 hours, the reaction solution was removed and the residue was washed with DMF, ethanol and DCM 3 times each.

Step 2 Removal of Resin

95% aqueous trifluoroacetic acid solution (800 μl) was added to the resin obtained in step 1, and they were stirred for 1 hour and then filtered. 95% aqueous trifluoroacetic acid solution (600 μl) was further added to the resin and they were stirred for 1 hour and then filtered. The filtrates were combined together and then concentrated. After the purification by the reversed-phase HPLC [Symmetry C18 column (5 μm; 19 mmφ×50 mm) of Waters Co., developer: water/acetonitrile (TFA 0.05%)], 5.4 mg of the intended compound was obtained.

MS (ESI positive): 494, 494, 496

$C_{23}H_{23}Cl_{12}N_3O_5$: 491, 493, 495

EXAMPLE 91

Synthesis of N-[2-(pyrrolidine-1-ylcarbonyl)-2-ethylbutanoyl]-4-{[(2,6-dichlorophenyl)carbonyl]amino}-L-phenylalanine Step 1 Acylation/Amidation Reaction A solution (250 μl) of 11.7 μl of pyridine in DCM and a solution (200 μl) of 12.9 μl of 2,6-dichlorobenzoyl chloride in DCM were added to the resin (dry weight: 49.8 mg) obtained in the same manner as that in step 2 in Example 94. After shaking at room temperature for 15 hours, the reaction solution was removed and the residue was washed with DMF, ethanol and DCM 3 times each.

Step 2 Removal of Resin

95% aqueous trifluoroacetic acid solution (800 μl) was added to the resin obtained in step 1, and they were shaken for 1 hour and then filtered. 95% aqueous trifluoroacetic acid solution (600 μl) was further added to the resin and they were stirred for 1 hour and then filtered. The filtrates were combined together and then concentrated. After the purification by the reversed-phase HPLC [Symmetry C18 column (5 μm; 19 mmφ×50 mm) of Waters Co., developer: water/acetonitrile (TFA 0.05%)],2.5 mg of the intended compound was obtained.

MS (ESI positive): 548, 550, 552

$C_{27}H_{31}Cl_2N_3O_5$: 547, 549, 551

EXAMPLE 92

Synthesis of N-(2-pyrrolidine-1-ylcarbonyl-2-ethylbutanoyl)-4-({[2-fluoro-6-(trifluoromethyl)phenyl]carbonyl}amino)-L-phenylalanine The same procedure as that of Example 91 was repeated except that 2,6-dichlorobenzoyl chloride was replaced with 2-fluoro-6-(trifluoromethyl)benzoyl chloride in step 1. D, E, K and L in Table 2-1 were substituents in general formula (1-2) given below. See Table 2-1.

MS (ESI positive): 566

$C_{28}H_{31}F_4N_3O_5$: 565

EXAMPLES 93, 95–99, 110–111 AND 477

Compounds in the respective Examples were synthesized in the same manner as that of Example 94 except that 5-chloro-2-(methylthio)pyrimidine-4-carboxylic acid used in step 3 in Example 94 was replaced with a corresponding carboxylic acid. D, E, K and L in Table 2-1 were substituents in general formula (1-2) given below. See Table 2-1.

EXAMPLE 94

Synthesis of N-[2-(pyrrolidine-1-ylcarbonyl)-2-ethylbutanoyl]-4-({[5-chloro-2-(methylthio)pyrimidine-4-yl]carbonyl}amino)-L-phenylalanine Step 1 Acylation/Amidation Reaction 15 ml of 20% solution of piperidine in DMF was added to the resin (dry weight: 1.52 g) obtained in the same manner as that of step 1 in Example 85, and they were shaken for 5 minutes. The reaction solution was removed. 15 ml of 20% solution of piperidine in DMF was added again to the residue, and they were stirred for 15 minutes. The reaction solution was removed, and the resin was washed with DMF, ethanol, DCM and NMP 3 times each. Separately, a solution (6 ml) of 680 mg of diethylmalonic acid and 1.74 g of HOAt in NMP was cooled with ice, and a solution (1 ml) of 1.98 ml of DIC in NMP was added thereto under cooling with ice. After stirring under cooling with ice for 30 minutes and then at room temperature for 30 minutes, the insoluble matter was removed by the filtration. The filtrate was added to the resin obtained as described above, and they were stirred at room temperature for 16 hours. The reaction solution was removed, and the resin was washed with DMF, DCM and NMP 3 times each. A solution (3 ml) of 493 μl of pyrrolidine in NMP, and then a solution (3 ml) of 810 mg of HOAt and 910 μl of DIC in NMP were added to the resin, and the reaction was conducted at room temperature for 16 hours. The reaction solution was removed, and the resin was washed with DMF, ethanol and DCM 3 times each.

Step 2 Reduction of Nitro Group

The resin obtained in step 1 was added to 21 ml of 1.73 M solution of stannic chloride dihydrate in NMP/EtOH (20:1) to conduct the reaction at room temperature for 3 hours. The reaction solution was removed, and the residue was washed with DMF, ethanol and DCM 3 times each. The obtained resin was dried under reduced pressure.

Step 3 Acylation Reaction

A solution (180 μl) of 18.1 mg of 5-chloro-2-(methylthio)-pyrimidine-4-carboxylic acid in DMF, a solution (141 μl) of 46.0 mg of PyBOP in DMF, a solution (141 μl) of 19.9 mg of HOBt in DMF and a solution (141 μl) of 30.8 μl of DIEA in DMF were successively added to 50.8 mg of the resin obtained in step 2, and they were shaken at room temperature for 15 hours. The reaction solution was removed, and the residue was washed with DMF, ethanol and DCM 3 times each.

Step 4 Removal of Resin

95% aqueous trifluoroacetic acid solution (800 μl) was added to the resin obtained in step 3, and they were shaken for 1 hour and then filtered. 95% aqueous trifluoroacetic acid solution (600 μl) was added to the resin, and they were shaken for 1 hour and then filtered. The filtrates were combined together and then concentrated. After the purification by the reversed-phase HPLC [Symmetry C18 column (5 μm; 19 mmφ×50 mm) of Waters Co., developer: water/acetonitrile (TFA 0.05%)], 6.6 mg of the intended compound was obtained.

MS (ESI positive): 562

$C_{26}H_{32}ClN_5O_5S$: 561

EXAMPLES 108–109

Compounds in the respective Examples were synthesized in the same manner as that of Example 90 except that a corresponding carboxylic acid chloride was used in place of 2,6-dichlorobenzoyl chloride used in step 1 in Example 90. D, E, K and L in Table 2-1 were substituents in general formula (1-2) given below. See Table 2-1.

EXAMPLE 478

Synthesis of N-[2-(pyrrolidine-1-ylcarbonyl)-2-ethylbutanoyl]-4-({[5-chloro-2-(methylsulfinyl)pyrimidine-4-yl]carbonyl}amino)-L-phenyl-alanine Step 1

A solution of 1.2 equivalents of 3-chloroperbenzoic acid in DCM was added to the resin obtained in step 3 in Example 94 and then they were shaken at room temperature for 1.5 hours. Then the reaction solution was removed and the residue was washed with DMF, ethanol and DCM 3 times each.

Step 2

95% aqueous trifluoroacetic acid solution (1 ml) was added to the resin obtained in step 1, and they were stirred for 1 hour and then filtered. 95% aqueous trifluoroacetic acid solution (1 ml) was further added to the resin and they were stirred for 1 hour and then filtered. The filtrates were combined together and then concentrated. After the purification by the reversed-phase HPLC [Symmetry C18 column (5 μm; 19 mmφ×50 mm) of Waters Co., developer: water/acetonitrile (TFA 0.05%)], the intended compound was obtained.

MS (ESI positive): 578 $[MH]^+$ (ESI negative): 576 $[M-H]^-$, 690 $[M+TFA-H]^-$ $C_{26}H_{32}ClN_5O_6S$: 577

EXAMPLE 479

Synthesis of N-[2-(pyrrolidine-1-ylcarbonyl)-2-ethylbutanoyl)-4-({[5-chloro-2-(methylsulfonyl)pyrimidine-4-yl]carbonyl}-amino)-L-phenyl-alanine Step 1

The resin obtained in step 3 in Example 94 was reacted with a solution of 5 equivalents of 3-chloroperbenzoic acid in DCM. Then the reaction solution was removed and the residue was washed with DMF, ethanol and DCM 3 times each.

Step 2

95% aqueous trifluoroacetic acid solution (1 ml) was added to the resin obtained in step 1, and they were stirred for 1 hour and then filtered. 95% aqueous trifluoroacetic acid solution (1 ml) was further added to the resin and they were stirred for 1 hour and then filtered. The filtrates were combined together and then concentrated. After the purification by the reversed-phase HPLC [Symmetry C18 column (5 μm; 19 mmφ×50 mm) of Waters Co., developer: water/acetonitrile (TFA 0.05%)], the intended compound was obtained.

MS (ESI positive): 594 $[MH]^+$ (ESI negative): 592 $[M-H]^-$, 706 $[M+TFA-H]^-$ $C_{26}H_{32}ClN_5O_7S$: 593

EXAMPLE 480

Synthesis of N-[2-(pyrrolidine-1-ylcarbonyl)-2-ethylbutanoyl]-4-[({5-chloro-2-[(4-methoxybenzyl)amino]pyrimidine-4-yl}carbonyl)amino]-L-phenylalanine Step 1

A solution of p-methoxybenzylamine (3 equivalents) in DMSO was added to the resin obtained in step 1 in Example 479. After shaking them at room temperature for 20 hours, the reaction solution was removed and the residue was washed with DMF, ethanol and DCM 3 times each.

Step 2

95% aqueous trifluoroacetic acid solution (1 ml) was added to the resin obtained in step 1, and they were shaken for 1 hour and then filtered. 95% aqueous trifluoroacetic acid solution (1 ml) was further added to the resin and they were stirred for 1 hour and then filtered. The filtrates were combined together and then concentrated. After the purification by the reversed-phase HPLC [Symmetry C18 column (5 μm; 19 mmφ×50 mm) of Waters Co., developer: water/acetonitrile (TFA 0.05%)], the intended compound was obtained.

MS (ESI positive): 651 $[MH]^+$ (ESI negative): 649 $[M-H]^-$, 763 $[M+TFA-H]^-$ $C_{33}H_{39}ClN_6O_6$: 650

EXAMPLES 481–484

Compounds in the respective Examples were synthesized in the same manner as that of Example 480 except that p-methoxybenzylamine used in step 1 in Example 480 was replaced with a corresponding amine. D, E, K and L in Table 2-1 were substituents in general formula (1-2) given below. See Table 2-1.

TABLE 2-1

(1-2)

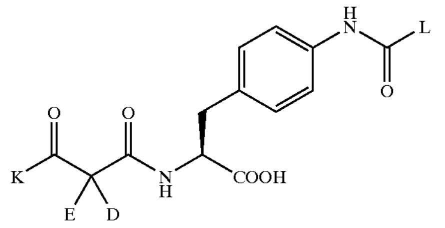

| Example | D | E | K | L | MS Found (MH+) |
|---|---|---|---|---|---|
| 85 | —(CH2)2— | | Me2N | partial structure 5 | 506 |
| 86 | —(CH2)2— | | Me2N | 2-Chloro-4,5-difluorophenyl | 494 |
| 87 | —(CH2)2— | | Me2N | 5-Bromo-2-Chlorophenyl | 536 |
| 88 | —(CH2)2— | | Me2N | 2,5-Dibromophenyl | 581 |
| 89 | —(CH2)2— | | Me2N | 2-Bromo-5-methoxyphenyl | 532 |
| 90 | —(CH2)2— | | Me2N | 2,6-Dichlorophenyl | 492, 494, 496 |
| 91 | Et | Et | Pyrrolidino | 2,6-Dichlorophenyl | 548, 550, 552 |
| 92 | Et | Et | Pyrrolidino | 2-Trifluoromethyl-5-fluorophenyl | 565 |
| 93 | Et | Et | Pyrrolidino | partial structure 6 | 564 |
| 94 | Et | Et | Pyrrolidino | partial structure 5 | 562 |
| 95 | Et | Et | Pyrrolidino | 2-Chloro-4,5-difluorophenyl | 550 |
| 96 | Et | Et | Pyrrolidino | 5-Bromo-2-Chlorophenyl | 593 |
| 97 | Et | Et | Pyrrolidino | 2-Nitrophenyl | 525 |
| 98 | Et | Et | Pyrrolidino | 2,5-Dibromophenyl | 638 |
| 99 | Et | Et | Pyrrolidino | 2-Bromo-5-methoxyphenyl | 588 |
| 106 | $—(CH_2)_2—$ | | $Me_2N$ | partial structure 6 | 508 |
| 107 | $—(CH_2)_2—$ | | $Me_2N$ | 2-Nitrophenyl | 469 |
| 108 | $—(CH_2)_2—$ | | $Me_2N$ | 2-Fluoro-6-(trifluoromethyl)phenyl | 510 |

TABLE 2-1-continued (1-2)

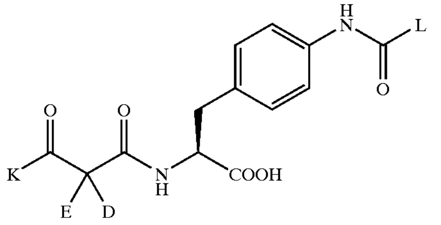

| Example | D | E | K | L | MS Found (MH+) |
|---|---|---|---|---|---|
| 109 | —$(CH_2)_2$— | | $Me_2N$ | 2,6-Difluorophenyl | 460 |
| 110 | Et | Et | Pyrrolidino | partial structure 7 | 539 |
| 111 | Et | Et | Pyrrolidino | partial structure 8 | 581 |
| 477 | Et | Et | Pyrrolidino | partial structure 8-1 | 606, 608 |
| 478 | Et | Et | Pyrrolidino | partial structure 8-2 | 578 |
| 479 | Et | Et | Pyrrolidino | partial structure 8-3 | 594 |
| 480 | Et | Et | Pyrrolidino | partial structure 8-4 | 651 |
| 481 | Et | Et | Pyrrolidino | partial structure 8-5 | 585 |
| 482 | Et | Et | Pyrrolidino | partial structure 8-6 | 599 |
| 483 | Et | Et | Pyrrolidino | partial structure 8-7 | 573 |
| 484 | Et | Et | Pyrrolidino | partial structure8-8 | 545 |

Partial Structures

5

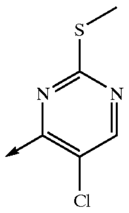

6

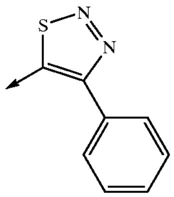

7

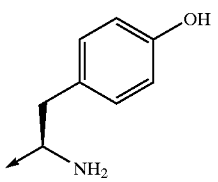

8

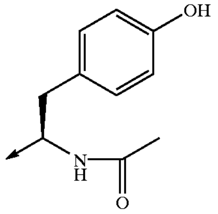

-continued 8-1

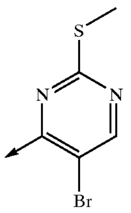

8-2

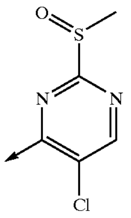

8-3

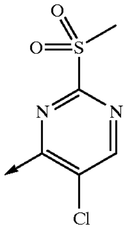

8-4

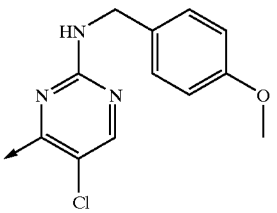

-continued 8-5

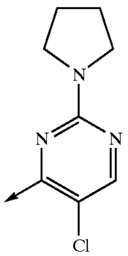

8-6

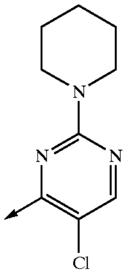

8-7

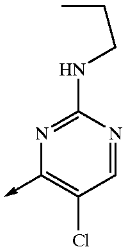

8-8

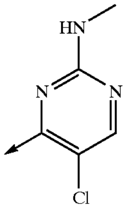

EXAMPLES 112–260

Compounds in the respective Examples were synthesized in the same manner as that of Example 85 except that 5-chloro-2-(methylthio)pyrimidine-4-carboxylic acid was replaced with a corresponding carboxylic acid in step 5 and the purification by HPLC was omitted. However, for a compound of the above formula wherein L has the unsubstituted amino group, the reaction is conducted by using a corresponding aminocarboxylic acid having an amino acid protected with Boc group. L in Table 2-1-1 is a substituent in the following general formula 1-2-1:

TABLE 2-1-1

(1-2-1)

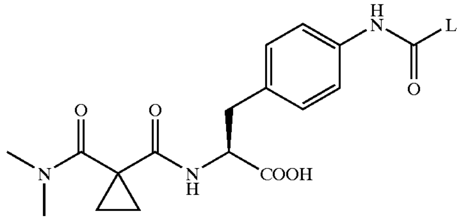

| Example | L—C(═O) | MS Found (MH+) |
|---|---|---|
| 112 | 2-Methyl-2-butenoyl | 402 |
| 113 | 1-Cyclohexene carbonyl | 428 |
| 114 | α-Ethyl-m-nitrocinnamoyl | 523 |
| 115 | 1-Phenyl-1-cyclopropanecarbonyl | 464 |
| 116 | 1-Methylcyclopropane-1-carbonyl | 402 |
| 117 | 2,2-Dichloro-1-methylcyclopropanecarbonyl | 470 |
| 118 | 2,2-Dimethyl-3-(2,2-dimethylvinyl)cyclo-propanecarbonyl | 470 |
| 119 | 9-Fluorenone-1-carbonyl | 526 |
| 120 | 5-Methyl-2-(trifluoromethyl)-3-furoyl | 496 |
| 121 | 1-Phenyl-5-(tritluoramethyl)pyrazole-4-carbonyl | 558 |
| 122 | 1-Methyl-5-nitropirazole-4-carbonyl | 473 |
| 123 | 4-Bromo-1-ethyl-3-methylpyrazole-5-carbonyl | 536 |
| 124 | 3-(2-Chlorophenyl)-5-methylisoxazole-4-carbonyl | 539 |
| 125 | 2,4-Dimethylthiazole-5-carbonyl | 459 |
| 126 | 2-(1,4-Benzodioxan-2-yl)thiazole-4-carbonyl | 565 |
| 127 | 4,5-Dichloro-isothiazole-3-carbonyl | 499 |
| 128 | 5-Bromo-2-furoyl | 492 |
| 129 | 2-Furoyl | 414 |
| 130 | 5-Nitro-2-furoyl | 459 |
| 131 | 3-Methyl-2-thenoyl | 444 |
| 132 | 3-Chloro-4-isoproylsulphonyl-5-methylthio-2-thenoyl | 616 |
| 133 | 4-Methoxy-3-thenoyl | 460 |
| 134 | 5-Methoxyindole-2-carbonyl | 493 |
| 135 | Benzothiazole-6-carbonyl | 481 |
| 136 | 8-Quinolinecarbonyl | 475 |
| 137 | 5,6-Dichloronicotinoyl | 493 |
| 138 | 5-Bromonicotinoyl | 503 |
| 139 | 6-Chloropyridine-2-carbonyl | 459 |
| 140 | 2H-Pyran-2-one-5-carbonyl | 442 |
| 141 | 2-(Methylthio)benzoyl | 470 |
| 142 | 2-Phenylbenzoyl | 500 |
| 143 | 2-Ethoxybenzoyl | 468 |
| 144 | 3-(Chloromethyl)benzoyl | 472 |
| 145 | 4-Diethylaminobenzoyl | 495 |
| 146 | 4-Bromo-2-methylbenzoyl | 516 |
| 147 | 4-Cyclohexylbenzoyl | 506 |
| 148 | 4-Phenoxybenzoyl | 516 |
| 149 | 2,3,6-Trimethoxybenzoyl | 514 |
| 150 | 2,6-Dimethoxy-3-nitrobenzoyl | 529 |
| 151 | 2,5-Difluorobenzoyl | 460 |
| 152 | 3-Aminosulfonyl-4-chlorobenzoyl | 537 |
| 153 | 3,4-Dichlorobenzoyl | 492 |
| 154 | 4-Methyl-3-nitrobenzoyl | 483 |
| 155 | 4-Dimethylamino-3,5-dinitrobenzoyl | 557 |
| 156 | DL-2-[4-(Trifluoromethoxy)phenoxy]propanoyl | 552 |
| 157 | Crotonoyl | 388 |
| 158 | trans-2-Ethoxycarbonyl-acryloyl | 446 |
| 159 | 2-Thiopheneacryloyl | 456 |
| 160 | 3,4-Dichiorocinnamoyl | 518 |
| 161 | 4-Methylcinnamoyl | 464 |
| 162 | o-Chlorocinnamoyl | 484 |
| 163 | 3-Fluorocinnamoyl | 468 |
| 164 | 1-(4-Chlorobenzyl)pyrrolidin-2-one-4-carbonyl | 555 |
| 165 | L-Pyroglutamyl | 431 |
| 166 | Thioprolyl | 435 |
| 167 | Tryptophyl | 506 |
| 168 | Phenylglycyl | 453 |
| 169 | Lys-(Cl-Z)- | 616 |
| 170 | Arg(Tos)- | 630 |
| 171 | Tyr(2-Br-Z)- | 695 |
| 172 | Asp(OcHex)- | 517 |

TABLE 2-1-1-continued (1-2-1)

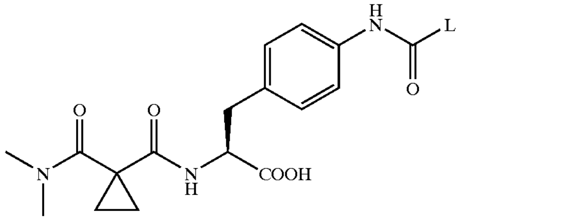

| Example | L—C(═O) | MS Found (MH+) |
|---|---|---|
| 173 | His(DNP)- | 623 |
| 174 | (2-Naphthoxy)acetyl | 504 |
| 175 | p-(Trifluoromethyl)phenylacetyl | 506 |
| 176 | 2-Iodophenylacetyl | 564 |
| 177 | 3,4-Dichlorophenylacetyl | 506 |
| 178 | (4-Fluorophenylthio)acetyl | 488 |
| 179 | (3-Acetyl-2-methyl-5-oxo-2-pyrrolin-4-yl)acetyl | 499 |
| 180 | Vinylacetyl | 388 |
| 181 | 3-[1,2-Dihydro-2-oxo-3-(trifluoromethyl)-pyrid-1-yl]propionyl | 537 |
| 182 | 3-(2-Benzoxazolin-2-on-3-yl)propionyl | 509 |
| 183 | (5-Methyl-2-phenyloxazol-4-yl)acetyl | 519 |
| 184 | 3-(2-Metbyl-4-nitroimidazol-1-yl)propionyl | 501 |
| 185 | 3-(Methoxycarbonyl)propionyl | 434 |
| 186 | (3,4-Methylenedioxy)phenylacetyl | 482 |
| 187 | R-(+)-α-Methoxy-α-(trifluoromethyl)phenylacetyl | 536 |
| 188 | 5-Chlorobicyclo[2.2.1]hept-2-en-5-endo-carbonyl | 474 |
| 189 | 5-Hydroxy-2-indolecarbonyl | 479 |
| 190 | Indole-2-carbonyl | 463 |
| 191 | 5-Methoxyindole-2-carbonyl | 493 |
| 192 | 2-Thenoyl | 430 |
| 193 | 3-Bromo-2-thenoyl | 508 |
| 194 | 5-Carboxy-2-thenoyl | 474 |
| 195 | 5-Methyl-2-thenoyl | 444 |
| 196 | 4-Methoxy-3-thenoyl | 460 |
| 197 | Picolinoyl | 425 |
| 198 | 5-Carboxypicolinoyl | 469 |
| 199 | 6-Carboxypicolinoyl | 469 |
| 200 | Nicotinoyl | 425 |
| 201 | 2-Chloronicotinoyl | 459 |
| 202 | 2,6-Dimethoxynicotinayl | 485 |
| 203 | 6-Chloronicotinoyl | 459 |
| 204 | 6-Methylnicotinoyl | 439 |
| 205 | 2-Chloroisonicotinoyl | 459 |
| 206 | 3-Carboxypyrazine-2-carbonyl | 470 |
| 207 | Benzoyl | 424 |
| 208 | N-Phenylanthraniloyl | 515 |
| 209 | 2-Bromobenzoyl | 502 |
| 210 | 2-Fluorobenzoyl | 442 |
| 211 | 2-Hydroxybenzoyl | 440 |
| 212 | 2-Iodobenzoyl | 550 |
| 213 | o-Anisoyl | 454 |
| 214 | o-Toluoyl | 438 |
| 215 | 2-Phenoxybenzoyl | 516 |
| 216 | 2-Benzoylbenzoyl | 528 |
| 217 | 3-Nitrobenzoyl | 469 |
| 218 | m-Bromobenzoyl | 502 |
| 219 | 3-Fluorobenzoyl | 442 |
| 220 | m-Hydroxybenzoyl | 440 |
| 221 | m-Iedobenzoyl | 550 |
| 222 | 3-Nitrobenzoyl | 469 |
| 223 | m-Anisoyl | 454 |
| 224 | 3-Formylbenzoyl | 452 |
| 225 | 3-Cyanobenzoyl | 449 |
| 226 | 3-Carboxybenzoyl | 468 |
| 227 | m-Toluoyl | 438 |
| 228 | 3-Dimethylaminobeuzoyl | 467 |
| 229 | 3-Methoxycarbonylbenzoyl | 482 |
| 230 | 3-Phenoxybenzoyl | 516 |
| 231 | 4-Dimethylaminobenzoyl | 467 |
| 232 | 4-Isopropylbenzoyl | 466 |
| 233 | 4-Phenylbenzoyl | 500 |
| 234 | 4-(Chloromethyl)benzoyl | 472 |

TABLE 2-1-1-continued (1-2-1)

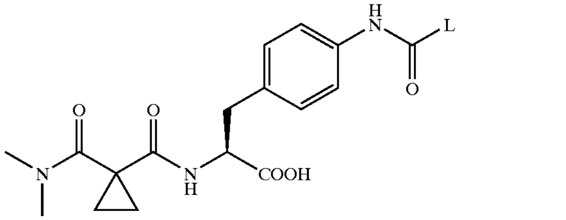

| Example | L—C(═O) | MS Found (MH+) |
|---|---|---|
| 235 | 4-(Dihydroxyboryl)benzoyl | 468 |
| 236 | 4-Iodobenzoyl | 550 |
| 237 | p-Anisoyl | 454 |
| 238 | 4-Formylbenzoyl | 452 |
| 239 | (p-Trifluoromethoxy)benzoyl | 508 |
| 240 | (p-Trifluoromethyl)benzoyl | 492 |
| 241 | 4-Acetamidobenzoyl | 481 |
| 242 | 4-Acetylbenzoyl | 466 |
| 243 | p-Ethylbenzoyl | 452 |
| 244 | 4-(Methoxyearbonyl)benzoyl | 482 |
| 245 | 4-Vinylbenzoyl | 450 |
| 246 | 4-Isopropylbenzoyl | 466 |
| 247 | 2-Methyl-3-nitrobenzoyl | 483 |
| 248 | 2,6-Dimethoxy-3-nitrobenzoyl | 529 |
| 249 | 2,4-Dimethylbenzoyl | 452 |
| 250 | 2-Methoxy-4-xnethylthiobenzoyl | 500 |
| 251 | 5-Bromosalicyloyl | 518 |
| 252 | 5-Chlorosalicyloyl | 474 |
| 253 | 5-Formylsalicyloyl | 468 |
| 254 | 5-Methoxy-2-nitrobenzoyl | 499 |
| 255 | 3-Bromo-4-methylbenzoyl | 516 |
| 256 | 3-Iodo-4-methylbenzoyl | 564 |
| 257 | 4-Methoxy-3-nitrobenzoyl | 499 |
| 258 | 3-Methoxy-4-nitrobenzoyl | 499 |
| 259 | 4-Methyl-3-nitrobenzoyl | 483 |
| 260 | 3,4-Dimethoxybenzoyl | 484 |

EXAMPLES 100 TO 103, 261, 263–273 AND 476

The compounds shown below were synthesized by using a corresponding dicarboxylic acid, amine and alkyl bromide in the same manner as that of steps 1 to 2 in Example 94 and Example 262. D, E and L in Table 2-2 are substituents in general formula (1-3) shown below. In Examples 261 and 273, the alkylation in step 2 in Example 262 was omitted and the resin was removed in step 3.

EXAMPLE 262

Synthesis of N-[1-(N,N-dimethylaminocarbonyl)cyclopropane-1-ylcarbonyl]-4-[1-allyl-2,4-dioxo-1,4-dihydroquinazoline-3(2H)-yl]-L-phenylalanine Step 1 Construction of quinazolidine-1,4-dione Ring by Urea Synthesis and Ring Closure 2 g of a resin obtained from 1,1-cyclopropanedicarboxylic acid and pyrrolidine in the same manner as that of steps 1 and 2 in Example 94 was added to a solution of methyl-2-isocyanate benzoate (1.92 g) in NMP (32 ml) to conduct the reaction for 16 hours. The reaction solution was removed, and the resin was washed with DMF and DCM 3 times each. Then 20% solution of piperidine in DMF was added to the resin to conduct the reaction for 1 hour. The reaction solution was removed, and the resin was washed with DMF and DCM 3 times each and then dried under reduced pressure.

Step 2 Alkylation

Allyl bromide (0.75 mmol), 18-crown-6 (30 mg), NMP (1 ml) and $K_2CO_3$ (35 mg) were added to 20 mg of the resin obtained in step 1 to conduct the reaction for 3 days. The reaction solution was removed, and the resin was washed with DMF, water, DMF and dichloromethane 3 times each and then dried under reduced pressure.

Step 3 Removal of Resin

The resin obtained in step 3 was treated with 95% aqueous trifluoroacetic acid solution for 1 hour. The resin was filtered out. The residue was concentrated under reduced pressure. Then 0.2 ml of water and 0.2 ml of acetonitrile were added to the concentrate and the obtained mixture was freeze-dried.

MS (ESI positive): 531

$C_{29}H_{30}N_4O_6$: 530

TABLE 2-2

(1-3)

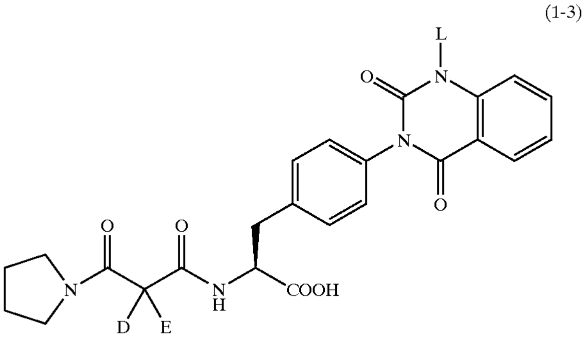

| Example | D | E | L | MS Found (MH+) |
|---|---|---|---|---|
| 261 | Et | Et | hydrogen | 521 |
| 262 | $—(CH_2)_2—$ | | Allyl | 530 |
| 263 | $—(CH_2)_2—$ | | 2,6-difluorobenzyl | 617 |
| 264 | $—(CH_2)_2—$ | | 4-pirrolidinephenacyl | 678 |
| 265 | $—(CH_2)_2—$ | | 2,6-dichlorobenzyl | 649 |
| 266 | $—(CH_2)_2—$ | | 4-nitrobenzyl | 625 |
| 267 | $—(CH_2)_2—$ | | phenylthioethyl | 627 |
| 268 | $—(CH_2)_2—$ | | 2,4-bis(trifluoromethyl)benzyl | 717 |
| 269 | $—(CH_2)_2—$ | | cyanomethyl | 530 |
| 270 | $—(CH_2)_2—$ | | cinnamyl | 607 |
| 271 | $—(CH_2)_2—$ | | 2-naphtylmethyl | 631 |
| 272 | $—(CH_2)_2—$ | | methoxycarbonylmethyl | 563 |
| 273 | $—(CH_2)_2—$ | | hydrogen | 491 |
| 100 | Et | Et | 2-naplitylmethyl | 661 |
| 101 | Et | Et | cinnamyl | 637 |
| 102 | Et | Et | 2-propynyl | 559 |
| 103 | Et | Et | methoxycarbonylmethyl | 593 |
| 476 | Et | Et | Methyl | 535 |

EXAMPLE 274

Synthesis of N-(2-pyrrolidine-1-ylcarbonyl-2-ethyl-butanoyl)-4-[4-oxoquinazoline-3(4H)-yl]-L-phenylalanine Step 1: Preparation of Resin 1 g of the resin obtained in steps 1 and 2 in Example 94 was added to a mixture of 2-nitrobenzoyl chloride (3.15 ml), 2,6-lutidine (2.8 ml) and NMP (24 ml) for 16 hours. The reaction solution was removed and the resin was washed with DCM and DMF 3 times each. The resin was added to a mixture of $SnCl_2 \cdot H_2O$ (10 g), NMP (21 ml) and ethanol (1.1 ml) to conduct the reaction for 16 hours. The reaction solution was removed, and the resin was washed with DMF and DCM 3 times each.

Step 2 Removal of Resin 20 mg of the resin obtained in step 1 was treated with a mixture of trimethyl o-formate (0.6 ml), acetic acid (50 $\mu$l) and NMP (0.6 ml) at 50° C. for 16 hours. The resin was filtered out, and the residue was concentrated under reduced pressure. Then 0.2 ml of water and 0.2 ml of acetonitrile were added to the concentrate and the obtained mixture was freeze-dried.

MS (ESI positive): 505

[$C_{28}H_{32}N_4O_5$: 504]

EXAMPLES 275–278

Compounds listed below were synthesized in the same manner as that of Example 274 except that a corresponding orthoformate was used. L in Table 2-2-1 was a substituent in general formula (1-3-1) given below.

TABLE 2-2-1

(1-3-1)

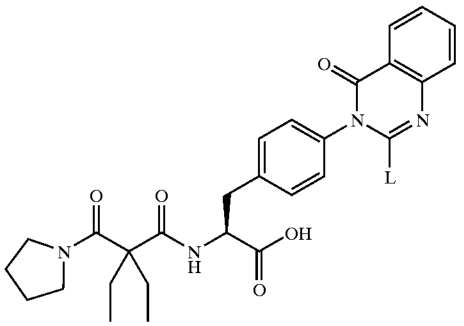

| Example | L | MS Found (MH+) |
|---|---|---|
| 274 | H | 505 |
| 275 | Me | 519 |
| 276 | MeO | 535 |
| 277 | propyl | 547 |
| 278 | Phe | 581 |

EXAMPLE 279

Synthesis of N-[1-(N,N-dimethylaminocarbonyl)-cyclopropane-1-ylcarbonyl]-4-{(7aS)-1,3-dioxo-tetrahydro-1H-pyrolo[1,2-C]imidazole-2(3H)-yl}-L-phenylalanine Step 1 Preparation of Resin 20 mg of the resin obtained in steps 1 to 4 in Example 85 was added to a mixture of 0.3 mmol of Fmoc-Pro-OH, 156 mg of PyBOP, 68 mg of HOBt and 105 $\mu$l of DIEA to conduct the reaction for 16 hours. The resin was washed with DMF and DCM 3 times each. After the reaction with 20% solution of piperidine in DMF for 1 hour, the reaction solution was removed and the resin was washed with DMF and DCM 3 times each. After reacting the resin with 49 mg of carbonyldiimidazole in the form of a solution (3 ml) in DCM for 30 minutes, the reaction solution was removed and the residue was washed with anhydrous DCM 5 times and then the reaction was carried out in DCM (2 ml) for 3 hours. The reaction solution was removed and the resin was washed with DCM 3 times and then dried under reduced pressure.

Step 2 Removal of the Resin 20 mg of the resin obtained in step 1 was treated with 95% aqueous trifluoroacetic acid solution for 1 hour. The resin was taken by the filtration. After the concentration under reduced pressure, water (0.2 ml) and acetonitrile (0.2 ml) were added to the residue and the product was freeze-dried.

MS (ESI positive): 443

[$C_{22}H_{26}N_4O_6$: 442]

EXAMPLES 280 TO 282 AND 458

The compounds listed below were synthesized in the same manner as that of Example 279 except that a corresponding amino acid was used. L and M in Table 2-2-2 each was a substituent in general formula (1-3-2) given below.

TABLE 2-2-2

(1-3-2)

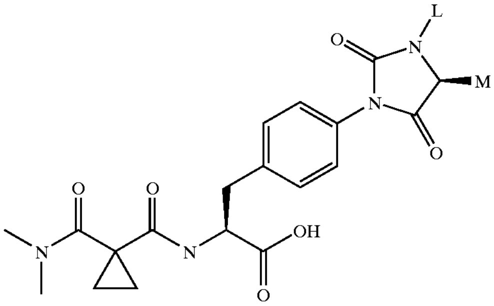

| Example | L | M | MS Found (MH+) |
|---|---|---|---|
| 279 | —CH2—CH2—CH2— | | 443 |
| 280 | H | Cyclohexylmethyl | 499 |
| 281 | H | Benzyl | 493 |
| 282 | H | Methyl | 417 |
| 458 | H | Isopropyl | 445 |

EXAMPLE 283

Synthesis of N-[1-(N,N-dimethylaminocarbonyl) cyclopropane-1-ylcarbonyl]-O-(2-cyclopentyl-ethyl)-L-tyrosine Step 1 Preparation of Resin 2.0 g of Wang resin (0.89 mmol/g) was washed with NMP once. Then a solution (20 ml) of 2.5 g of Fmoc-Tyr(2-chlorotrityl)-OH, 0.5 ml of 2,6-dichlorobenzoyl chloride and 0.5 ml of pyridine in DMF was added to the resin, and the mixture were shaken at room temperature for 16 hours. The superfluous solvent was removed, and the resin was washed with DMF 3 times, with DCM 3 times and with DMF twice. The obtained resin was treated with 20% solution of piperidine in DMF at room temperature for 1 hour. The solvent was removed and the resin was treated with DMF and DCM 3 times each and then dried under reduced pressure.

Step 2 Acylation Reaction 100 mg of the resin obtained in step 1 was added to a solution of 200 mg of 1,1-cyclopropanedicarboxylic acid, 210 mg of HOAt, 240 μl of DIC and 2.0 ml of DMF to conduct the reaction at room temperature for 16 hours. The reaction solution was removed and the residue was washed with anhydrous DCM 5 times. The reaction was carried out in 3.0 ml of 2 M solution of dimethylamine in THF and a solution of 480 mg of HOAt and 520 μl of DIC in 4 ml of DMF for 16 hours. The reaction solution was removed and the resin was washed with DMF and DCM 3 times each and then dried under reduced pressure.

Step 3 Removal of 2-chlorotrityl Group

The whole amount of the resin obtained in step 2 was washed with DCM 3 times and then treated with a mixed solution of 5.7 ml of DCM, 60 μl of TFA and 900 μl of TIPS for 2 minutes repeatedly 3 times. Then the resin was washed with DCM 5 times and dried under reduced pressure.

Step 4 Mitsunobu Reaction 20 mg of the resin obtained in step 3 was added to a mixture of 103 mg of TMAD, 3157 mg of PPh, 1.6 ml of DCM and 69 μl of cyclopentane ethanol to conduct the reaction for 16 hours. The reaction solution was removed, and the resin was washed with DCM, DMF and DCM twice each and then dried under reduced pressure.

Step 5 Removal of Resin

The resin obtained in step 4 was treated with 95% aqueous trifluoroacetic acid solution for 1 hour, then filtered and concentrated under reduced pressure. 0.2 ml of water and 0.2 ml of acetonitrile were added thereto and the product was freeze-dried.

MS (ESI positive): 417

[$C_{23}H_{32}N_2O_5$: 416]

EXAMPLES 284–298

The compounds listed below were synthesized in the same manner as that of Example 284 except that a corresponding alcohol was used. D in Table 2-2-3 was a substituent in general formula (1-3-3) given below.

TABLE 2-2-3

(1-3-3)

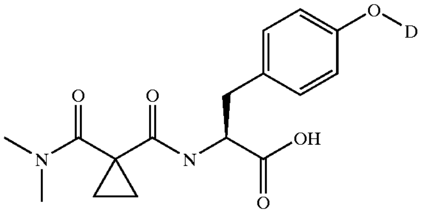

| Example | D | MS Found (MH+) |
|---|---|---|
| 283 | 2-cyclopentylethyl | 417 |
| 284 | ethyl | 349 |
| 285 | cyclopentyl | 389 |
| 286 | cyclohexylmethyl | 417 |
| 287 | cycloheptyl | 417 |
| 288 | propinyl | 359 |
| 289 | 3-phenoxybenzyl | 503 |
| 290 | pyridin-3-ylmethyl | 412 |
| 291 | pyridin-2-ylmethyl | 412 |
| 292 | 2-phenethyl | 425 |
| 293 | 3-pyridin-3-ylpropyl | 440 |
| 294 | 2-thiophen-2-ylethyl | 431 |
| 295 | 2-(benzyloxy)ethyl | 456 |
| 296 | 2-(2-naphtyl)ethyl | 475 |
| 297 | 2-indanyl | 437 |
| 298 | cyclobutylmethyl | 389 |

EXAMPLE 299

Synthesis of N-[1-(N,N-dimethylaminocarbonyl) cyclopropane-1-ylcarbonyl]-4-phenyl-L-phenyl-alanine Step 1 Preparation of Resin 1.4 g of Wang resin (0.89 mmol/g) was washed with NMF once. Then a solution (25 ml) of 2.5 g of Fmoc-Phe(4-I)—OH, 0.66 ml of 2,6-dichlorobenzoyl chloride and 1.3 ml of pyridine in DMF was added to the resin, and the mixture was shaken at room temperature for 16 hours. The superfluous solvent was removed, and the resin was washed with DMF 3 times, with DCM 3 times and DMF twice. The obtained resin was treated with 20% solution of piperidine in DMF at room temperature for 1 hour. The solvent was removed and the resin was washed with DMF and DCM 3 times each and then dried under reduced pressure. The acylation reaction was conducted in the same manner as that of step 2 in Example 283.

Step 2 Suzuki Reaction 20 mg of the resin obtained in step 1 was added to a solution of phenylboric acid (0.015 mmol), $PdCl_2$ (dppf), $CH_2Cl_2$ (0.015 mmol), TEA (0.75 ml) and DMF (1.05 ml) to conduct the reaction at 80° C. for 24 hours. The reaction solution was removed and the resin was washed with anhydrous DMF 8 times and with DCM 3 times, and then dried under reduced pressure.

Step 3 Removal of Resin

The resin obtained in step 2 was treated with 95% aqueous trifluoroacetic acid solution (1.5 ml) for 1 hour, then filtered and the filtrate was concentrated under reduced pressure. After the purification by the reversed-phase HPLC [Inertsil ODS, developer: water, acetonitrile (TFA 0.05%)], 0.7 mg of the intended compound was obtained.

MS (ESI positive): 381

$C_{22}H_{24}N_2O_4$: 380

EXAMPLES 300–306

The compounds listed below were synthesized in the same manner as that of Example 299 except that a corresponding boric acid was used.

D in Table 2-2-4 was a substituent in general formula (1-3-4) given below.

TABLE 2-2-4

(1-3-4)

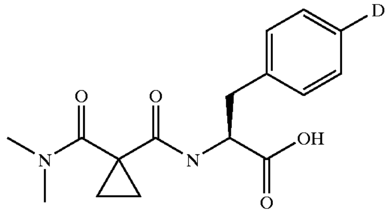

| Example | D | MS Found (MH+) |
|---|---|---|
| 299 | phenyl | 381 |
| 300 | 2-benzofuranyl | 421 |
| 301 | 2-thiophenyl | 387 |
| 302 | 3-pyridyl | 382 |
| 303 | 2-benzothiophenyl | 437 |
| 304 | 2-methoxyphenyl | 411 |
| 305 | 2-methylphenyl | 395 |
| 306 | 2-chlorophenyl | 415 |

EXAMPLE 105

Synthesis of N-[3-(dimethylamino)-2,2-dimethyl-3-oxopropanoyl]-4-(2,6-dimethoxyphenyl)-L-phenylalanine Step 1 Synthesis of Hydrochloride of Methyl Ester of 4-(2,6-dimethoxyphenyl)-L-phenylalanine hydrochloride 15.1 g of Boc-Tyr-OMe was dissolved in 70 ml of methylene chloride. 20.6 ml of pyridine was added to the obtained solution. 9.41 ml of anhydrous trifluoromethanesulfonic acid was added dropwise to the obtained mixture at 0° C. After stirring at 0° C. for 1 hour, the reaction mixture was diluted with 100 ml of methylene chloride and then washed with a saturated aqueous ammonium chloride solution (100 ml) and then with water (100 ml×2). The organic layer was dried over anhydrous sodium sulfate and then concentrated under reduced pressure to obtain 21.9 g (100%) of the intended compound.

1H-NMR (CDCl3) δ=1.43 (9H, s), 3.05 (1H, dd, J=6.6, 14.0 Hz), 3.19 (1H, dd, J=5.7, 14.0 Hz), 3.73 (3H, s), 4.59–4.65 (1H, m), 5.03 (1H, d, J=6.9 Hz), 7.20–7.27 (4H, m).

9.80 g of the compound obtained as described above was dissolved in 170 ml of DME under argon atmosphere. 12.6 g of potassium carbonate, 5.01 g of 2,6-dimethoxyphenylboronic acid and 2.65 g of tetrakis (triphenylphosphine) palladium (0) were added to the obtained solution. The reaction mixture was stirred at 70° C. for 6 hours and then dissolved in 150 ml of water. After the extraction with ethyl acetate (150 ml×3), the organic layers were combined together and then dried over anhydrous sodium sulfate and concentrated under reduced pressure. The residue was purified by the silica gel column chromatography to obtain 8.64 g (91%) of the intended compound.

1H-NMR (CDCl3) δ=1.55 (9H, s), 3.09–3.16 (2H, m), 3.72 (6H, s), 3.74 (3H, s), 4.59–4.66 (1H, m), 5.01–5.06 (1H, m), 6.65 (2H, d, J=8.7 Hz), 7.15–7.30 (5H, m).

8.64 g of the compound thus obtained was dissolved in 4 N hydrochloric acid/ethyl acetate solution (100 ml), and the obtained solution was stirred for 4 hours. The crystals thus precipitated were taken by the filtration and then washed with ethyl acetate. The crystals were dried to obtain 7.01 g (96%) of intended hydrochloride of methyl ester of 4-(2,6-dimethoxyphenyl)-L-phenylalanine hydrochloride in the form of white crystals.

1H-NMR (CDCl3) δ=3.47 (2H, t, J=5.4 Hz), 3.71 (6H, s), 3.81 (3H, s), 4.43 (1H, t, J=5.4 Hz), 6.63 (2H, d, J=8.4 Hz), 7.24–7.35 (5H, m), 8.73 (2H, br s).

MS (ESI positive): 316

[$C_{18}H_{21}NO_4$·HCl: 315 36.5]

Step 2 Acylation Reaction 35.2 mg of hydrochloride of methyl ester of 4-(2,6-dimethoxyphenyl)-L-phenylalanine hydrochloride obtained in step 1 was dissolved in DCM (1 ml) containing one drop of DIEA. The obtained solution was added dropwise to a suspension (1 ml) of 23.7 mg of 3-(dimethylamino)-2,2-dimethyl-3-oxopropanoic acid and PS-carbodiimide (1.15 mol/g, 174 mg) in DCM. After stirring at room temperature overnight, the reaction mixture was filtered The filter was thoroughly washed with methylene chloride. The filtrate and the wash solution were combined together and concentrated under reduced pressure. After the purification by a silica gel column chromatography, 23.1 mg of the intended compound was obtained.

1H-NMR (CDCl3) δ=1.23 (3H, s), 1.41 (3H, s), 2.51 (3H, s), 2.81 (3H, s), 2.85 (1H, dd, J=10.1, 14.3 Hz), 3.30 (1H, dd, J=4.4, 14.3 Hz), 3.71 (6H, s), 3.76 (3H, s), 4.86–4.94 (1H, m), 5.77 (1H, d, J=8.4 Hz), 6.64 (2H, d, J=8.0 Hz), 7.16 (2H, d, J=8.0 Hz), 7.22–7.30 (3H, m).

Step 3 Demethylation Reaction 23.1 mg of the compound obtained in step 2 was dissolved in 1 ml of a solvent mixture of methanol/THF. A solution of 25.6 mg of lithium hydroxide in 0.5 ml of water was added to the obtained solution. They were stirred at room temperature for 3 hours and then diluted with 1 N aqueous sodium hydroxide solution (10 ml). The reaction mixture was washed with 10 ml of DCM twice, and the aqueous layer was adjusted to pH 2 with 1 N hydrochloric acid. After the extraction with 10 ml of DCM 3 times, the organic layers were combined together, dried over anhydrous sodium sulfate and concentrated under reduced pressure. 18.6 mg (83%) of the intended compound was obtained in the form of a white powder.

1H-NMR (CDCl3) δ=1.31 (3H, s), 1.41 (3H, s), 2.44 (3H, s), 2.81 (3H, s), 2.99 (1H, dd, J=110.5, 14.3 Hz), 3.40 (1H, dd, J=4.5, 14.3 Hz), 3.70 (6H, s), 4.89–4.97 (1H, m), 6.41 (1H, br s), 6.64 (2H, d, J=8.4 Hz), 7.22–7.30 (5H, m).

MS (ESI positive): 443

[$C_{24}H_{30}N_2O_6$·HCl: 442]

EXAMPLE 307

Synthesis of N-[2-ethyl-2-(pyrrolidine-1-ylcarbonyl) butanoyl]-4-(2,6-dimethoxyphenyl)-L-phenylalanine Step 1 Synthesis of HOAt Ester 640 mg of diethylmalonic acid and 1.63 g of HOAt were dissolved in 10 ml of NMP. 1.86 ml of DICD was added to the obtained solution. After stirring at room temperature for 1.5 hours, 5 ml of a solution of 704 mg of hydrochloride of methyl ester of 4-(2,6-dimethoxyphenyl)-L-phenylalanine and 0.35 ml of DIEA in NMP was added dropwise to the reaction mixture. They were stirred for additional 2 hours, and the reaction solution was diluted with 100 ml of ethyl acetate. The reaction mixture was washed with saturated aqueous sodium chloride solution (100 ml×2) and then with 100 ml of water. The organic layer was dried over anhydrous sodium sulfate and then concentrated under reduced pressure. The residue was purified by the silica gel column chromatography to obtain 1.15 g (100%) of the intended compound.

1H-NMR (CDCl3) δ=0.91 (3H, t, J=7.5 Hz), 1.15 (3H, t, J=7.5 Hz), 2.18–2.32 (4H, m), 3.07 (1H, dd, J=7.2, 13.1 Hz), 3.29 (1H, dd, J=5.4, 13.1 Hz), 3.69 (6H, s), 3.75 (3H, s), 4.95–5.02 (1H, m), 6.64 (2H, d, J=8.4 Hz), 7.16–7.30 (5H, m), 7.46 (1H, dd, J=4.5, 8.4 Hz), 7.72 (1H, d, J=8.1 Hz), 8.44 (1H, dd, J=1.5, 8.4 Hz), 8.71 (1H, dd, J=1.5, 4.5 Hz).

Step 2 Synthesis of Methyl Ester of N-[2-ethyl-2-(pyrrolidine-1-ylcarbonyl)butanoyl]-4-(2,6-dimethoxyphenyl)-L-phenylalanine 57.5 mg of the compound obtained in step 1 was dissolved in 3 ml of NMP. 9.88 μl of pyrrolidine was added to the obtained solution. The mixture was stirred for 30 minutes and then diluted with 10 ml of 1 N aqueous hydrochloric acid solution. After the extraction with ethyl acetate (10 ml×3), the organic layers were combined together and washed with water (10 ml×3). The organic layer was dried over anhydrous sodium sulfate and then concentrated under reduced pressure. The residue was purified by the silica gel column chromatography to obtain 38.2 mg (75%) of methyl ester of N-[2-ethyl-2-(pyrrolidine-1-ylcarbonyl)butanoyl]-4-(2,6-dimethoxyphenyl)-L-phenylalanine.

1H-NMR (CDCl3) δ=0.61 (3H, t, J=7.5 Hz), 0.75 (3H, t, J=7.5 Hz), 1.64–2.00 (8H, m), 2.91 (1H, dd, J=9.5, 14.0 Hz), 3.09–3.14 (1H, m), 3.21 (1H, dd, J=4.8, 14.0 Hz), 3.29–3.35 (1H, m), 3.41-3.49 (2H, m), 3.71 (6H, s), 3.74 (3H, s), 4.82–4.89 (1H, m), 6.05 (1H, d, J=7.5 Hz), 6.64 (1H, d, J=8.7 Hz), 7.16 (2H, d, J=8.1 Hz), 7.24–7.29 (3H, m).

MS (ESI positive): 511

[$C_{29}H_{38}N_2O_6$: 510]

Step 3 Demethylation Reaction

The same procedure as that of step 3 in Example 105 was repeated to obtain the intended compound.

1H-NMR (CDCl3) δ=0.59 (3H, t, J=7.5 Hz), 0.74 (3H, t, J=7.5 Hz), 1.74–2.00 (8H, m), 2.99 (1H, dd, J=9.5, 14.2 Hz), 3.09–3.17 (1H, m), 3.31 (1H, dd, J=4.8, 14.2 Hz), 3.28–3.48 (1H, m), 3.40–3.48 (2H, m), 3.70 (6H, s), 4.82–4.89 (1H, m), 6.55 (1H, d, J=6.9 Hz), 6.63 (1H, d, J=8.7 Hz), 7.21–7.29 (5H, m).

MS (ESI positive): 497

[$C_{28}H_{36}N_2O_6$: 496]

EXAMPLES 104 AND 308 TO 342

The compounds listed below were synthesized in the same manner as that of Example 307 except that a suitable reagent was used. D, E and K in Table 2-3 were substituents in general formula (1-4) given below.

TABLE 2-3

(1-4)

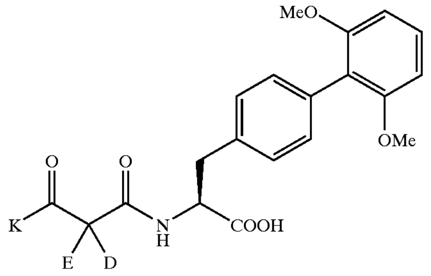

| Example | D | E | K | MS Found(MH+) |
|---|---|---|---|---|
| 104 | Et | Et | dimethylamino | 471 |
| 105 | Me | Me | dimethylamino | 443 |
| 307 | Et | Et | pyrrolidin-1-yl | 497 |
| 308 | Et | Et | 3R-3-hydroxypyrrolidin-1-yl | 513 |
| 309 | Et | Et | 3R-3-(dimethylamino)pyrrolidin-1-yl | 540 |
| 310 | Et | Et | 3S-3-(acetylamino)pyrrolidin-1-yl | 554 |
| 311 | Et | Et | 3R-3-(acetylamino)pyrrolidin-1-yl | 554 |
| 312 | Et | Et | (1S,4S)-2,5-diazabicyclo[2.2.1]hept-2-yl | 524 |
| 313 | Et | methoxyethyl | R-3-hydroxypyrrolidin-1-yl | 543 |
| 314 | Et | Et | ethyl(methyl)amino | 485 |
| 315 | Et | Et | diethylamino | 499 |
| 316 | Et | Et | tert-butylamino | 499 |
| 317 | Et | Et | piperidin-1-yl | 511 |
| 318 | Et | Et | morpholin-4-yl | 513 |
| 319 | Et | Et | azepan-1-yl | 525 |
| 320 | Et | Et | benzyl(methyl)amino | 547 |
| 321 | Et | Et | (2-methoxyethyl)amino | 501 |
| 322 | Et | Et | (2-hydroxyethyl)methylamino | 501 |
| 323 | Et | Et | (3-hydroxypropyl)amino | 501 |
| 324 | Et | Et | (4-hydroxybutyl)amino | 515 |
| 325 | Et | Et | (2-hydroxy-1,1-dimethylethyl)amino | 515 |
| 326 | Et | Et | 3-hydroxypiperidin-1-yl | 527 |
| 327 | Et | Et | 4-hydroxypiperidin-1-yl | 527 |
| 328 | Et | Et | (4-hydroxycyclohexyl)amino | 541 |
| 329 | Et | Et | 3-(hydroxymethyl)piperidin-1-yl | 541 |

TABLE 2-3-continued (1-4)

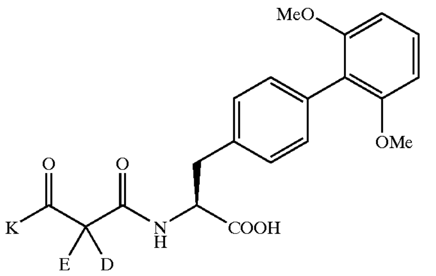

| Example | D | E | K | MS Found(MH+) |
|---|---|---|---|---|
| 330 | Et | Et | (2-methoxybenzyl)amino | 563 |
| 331 | Et | Et | (3-methoxybenzyl)amino | 563 |
| 332 | Et | Et | (4-methoxybenzyl)amino | 563 |
| 333 | Et | Et | (2-phenoxyethyl)amino | 563 |
| 334 | Et | Et | (2-furylmethyl)amino | 523 |
| 335 | Et | Et | (pyridin-2-ylmethyl)amino | 534 |
| 336 | Et | Et | (pyridin-3-ylmethyl)amino | 534 |
| 337 | Et | Et | (pyridin-4-ylmethyl)amino | 534 |
| 338 | Et | Et | (pyrazin-2-ylmethyl)amino | 535 |
| 339 | Et | Et | [3-(1H-imidazol-1-yl)propyl]amino | 551 |
| 340 | Et | Et | [3-2-oxopyrrolidin-1-yl)propyl]amino | 568 |
| 341 | Et | Et | (2-hydroxycyclohexyl)amino | 541 |
| 342 | Et | Et | dimethylamino | 471 |

EXAMPLE 343

Synthesis of N-[1-(N,N-dimethylaminocarbonyl) cyclopropane-1-ylcarbonyl]-4-[(2-methylphenyl-sulfonyl) amino]-L-phenylalanine 120 mg of the resin obtained in the same manner as in steps 1 to 4 in Example 85 was added to a solution of 200 mg of 2-methylbenzenesulfonyl chloride, 400 μl of 2,6-lutidine and 2 ml of dichloromethane to conduct the reaction at 0° C. for 24 hours. The reaction solution was removed, and the resin was washed with dichloromethane, NMP and dichloromethane 3 times each. The obtained resin was treated with 100% trifluoroacetic acid for 1 hour and then filtered. The obtained solution was concentrated and then purified by the reversed phase HPLC (SYMMETRY 19*50 mm mobile phase, water/acetonitrile each containing 0.1% of TFA) to obtain 2.0 mg of the intended compound.

MS (ESI positive): 474

[$C_{23}H_{27}N_3O_6S$: 473]

EXAMPLES 344 TO 362

The sulfonamides (general formulae 1-5 and 1-6) listed below were synthesized in the same manner as that of Example 343 except that a corresponding sulfonyl chloride was used. $L_1$ in Table 2-4 and $L_2$, $L_3$, $L_4$, $L_5$ and $L_6$ in Table 2-5 are each a substituent in general formulae (1-5 and 1-6) given below.

TABLE 2-4

(1-5)

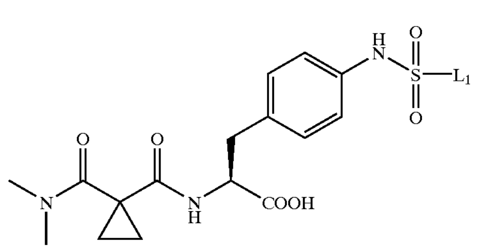

| Example | L1-SO2— | MS Found (MH+) |
|---|---|---|
| 344 | 2-Bromobenzenesulfonyl | 539 |
| 345 | 2-(Methoxycarbonyl)benzenesulfonyl | 518 |
| 346 | 5-Bromo-2-methoxybenzenesulfonyl | 569 |
| 347 | 2,4,6-Triisopropylbenzenesulfonyl | 586 |
| 348 | Quinoline-8-sulfonyl | 511 |
| 349 | Dansyl | 553 |
| 350 | 2-Acetamido-4-methyl-5-thiazolesulfonyl | 538 |
| 351 | 5-Bromothiophene-2-sulfonyl | 545 |
| 352 | partial structure 9 | 534, 536 |
| 353 | partial structure 10 | 534 |
| 354 | partial structure 11 | 466 |

partial structure 9

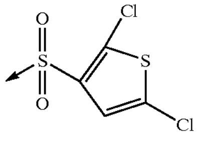

-continued partial Structure 10

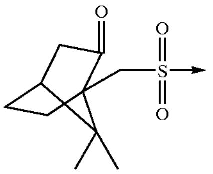

partial structure 11

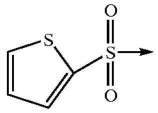

TABLE 2-5

(1-6)

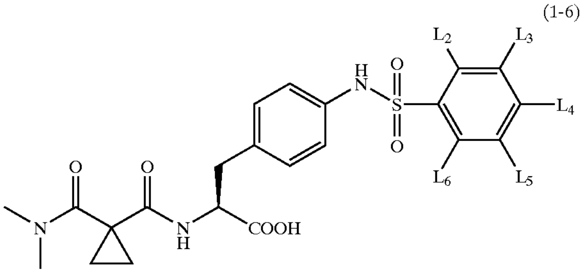

| Example | L2 | L3 | L4 | L5 | L6 | MS Found (MS+) |
|---|---|---|---|---|---|---|
| 355 | Me | H | Me | H | Me | 502 |
| 356 | CF3 | H | H | H | H | 528 |
| 357 | Cl | H | H | H | Cl | 528, 530, 532 |
| 358 | OMe | H | Me | H | H | 504 |
| 359 | OMe | H | OMe | H | H | 520 |
| 360 | H | CF3 | H | H | H | 528 |
| 361 | CN | H | H | H | H | 485 |
| 362 | Me | H | H | NO2 | H | 519 |

EXAMPLES 363 TO 379

The carboxylic acids (general formula 1-7) listed below were synthesized in the same manner as that of step 3 in Example 85 except that an amine and pyrrolidine were used and in the same manner as that of Example 343 except that a corresponding sulfonyl chloride was used. L7, L8, L9, L10 and L11 in Table 2-6 are each a substituent in general formula (1-7) given below.

TABLE 2-6

(1-7)

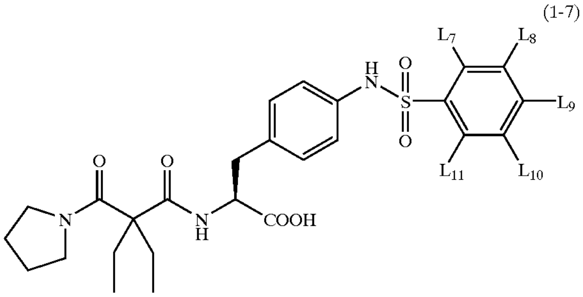

TABLE 2-6-continued (1-7)

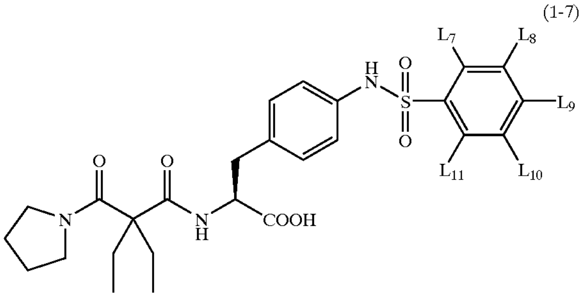

| Example | L7 | L8 | L9 | L10 | L11 | MS Found (MH+) |
|---|---|---|---|---|---|---|
| 363 | OMe | H | H | Br | H | 625 |
| 364 | Br | H | H | H | H | 595 |
| 365 | Cl | Cl | Cl | H | H | 618 |
| 366 | Me | Me | OMe | H | Me | 588 |
| 367 | Me | H | Cl | Me | H | 578 |
| 368 | Me | Me | H | Me | Me | 572 |
| 369 | Me | Me | Me | Me | Me | 586 |
| 370 | Cl | H | Cl | Cl | H | 618 |
| 371 | Cl | H | Cl | H | Cl | 618 |
| 372 | Me | Cl | H | H | H | 564 |
| 373 | Cl | H | H | Cl | H | 584 |
| 374 | Cl | H | H | H | H | 550 |
| 375 | Cl | Cl | H | H | H | 584 |
| 376 | Cl | H | Cl | H | H | 584 |
| 377 | Me | H | H | F | H | 548 |
| 378 | F | H | H | H | H | 534 |
| 379 | Me | H | H | NO2 | H | 575 |

EXAMPLE 380

Synthesis of N-[1-(N,N-dimethylaminocarbonyl)cyclopropane-1-ylcarbonyl]-4-(ethyl{[4-(trifluoro-methyl)phenyl]sulfonyl}amino)-L-phenylalanine A corresponding sulfonamide resin was obtained in the same manner as that of Example 343 except that 4-trifluoromethylbenzenesulfonyl chloride was used. 200 μl of ethyl bromide, 600 mg of potassium carbonate and 1 ml of NMP were added to 30 mg of the resin. The obtained solution was shaken at 35° C. for 24 hours. The reaction solution was removed, and the resin was washed with DCM, NMP and DCM 3 times each. The obtained resin was treated with trifluoroacetic acid for 1 hour and then filtered out. The obtained solution was concentrated to obtain the intended compound without the purification.

MS (ESI positive): 556

[$C_{25}H_{28}F_3N_3O_6S$: 555]

EXAMPLES 381 TO 390

Carboxylic acids (general formula 1-8) were obtained by using corresponding sulfonyl chlorides in the same manner as that of Example 343. 200 μl of a corresponding bromide, 600 mg of potassium carbonate and 1 ml of NMP were added to 30 mg of the sulfonamide resin thus obtained, and the obtained solution was shaken at 35° C. for 24 hours. The reaction solution was removed, and the resin was washed with DCM, NMP and DCM 3 times each. The obtained resin was treated with trifluoroacetic acid for 1 hour and then filtered out. The obtained solution was concentrated to obtain the intended compound without the purification.

$L_{12}$, $L_{13}$, $L_{14}$, $L_{15}$ and $L_{16}$ in Table 2-7 are each a substituent in general formula (1-8) given below.

TABLE 2-7

(1-8)

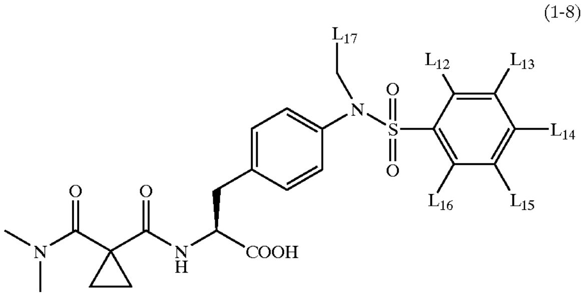

| Example | L12 | L13 | L14 | L15 | L16 | L17 | MS Found (MH+) |
|---|---|---|---|---|---|---|---|
| 381 | H | H | CF3 | H | H | CN | 567 |
| 382 | H | H | tBu | H | H | CN | 555 |
| 383 | H | H | Cl | H | H | CN | 534 |
| 384 | H | H | Me | H | H | CN | 513 |
| 385 | H | H | Ph | H | H | CN | 575 |
| 386 | H | H | CF3 | H | H | 2-CN—Ph | 643 |
| 387 | H | H | CF3 | H | H | CH2CH | 568 |
| 388 | H | H | CF3 | H | H | 2-Cl—Ph | 653 |
| 389 | H | H | CF3 | H | H | 2-NO2—Ph | 663 |
| 390 | H | H | CF3 | H | H | 2,6-DiCl—Ph | 687 |

EXAMPLES 391 TO 397

Carboxylic acids (general formula 1-9) were obtained by using corresponding sulfonyl chlorides in the same manner as that of Example 343. 200 μl of a corresponding bromide, 600 mg of potassium carbonate and 1 ml of NMP were added to 30 mg of the sulfonamide resin thus obtained, and the obtained solution was shaken at 35° C. for 24 hours. The reaction solution was removed, and the resin was washed with dichloromethane, NMP and dichloromethane 3 times each. The obtained resin was treated with trifluoroacetic acid for 1 hour and then filtered out. The obtained solution was concentrated to obtain the intended compound without the purification.

$L_{18}$ and $L_{19}$ in Table 2-8 are each a substituent in general formula (1-9) given below.

TABLE 2-8

(1-9)

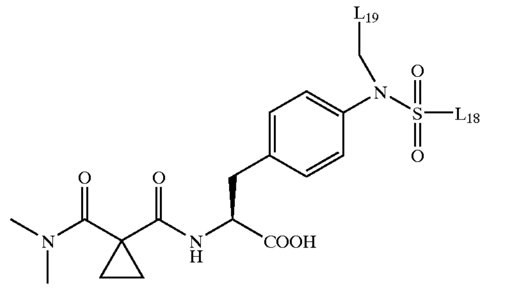

| Example | L18 | L19 | MS Found (MH+) |
|---|---|---|---|
| 391 | Et | CN | 451 |
| 392 | 2-Naphthyl | CN | 549 |
| 393 | 1-Naphthyl | CN | 549 |
| 394 | Benzyl | 2-CN—Ph | 589 |
| 395 | partial structure 12 | CN | 466 |

TABLE 2-8-continued (1-9)

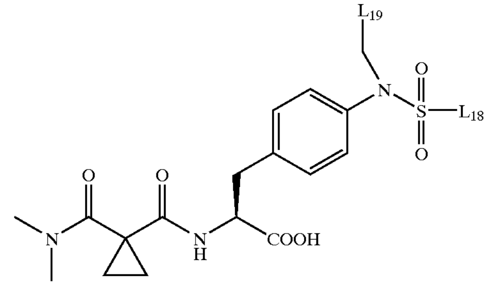

| Example | L18 | L19 | MS Found (MH+) |
|---|---|---|---|
| 396 | partial structure 13 | 2-CN—Ph | 645 |
| 397 | partial structure 14 | Et | 721 |

partial structure 12

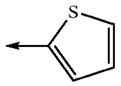

partial structure 13

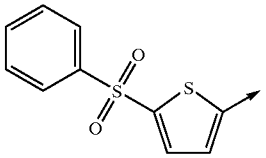

partial structure 14

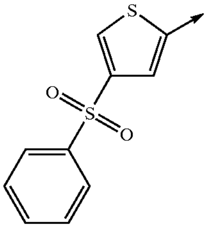

EXAMPLE 398

Synthesis of N-[1-(N,N-dimethylaminocarbonyl)cyclopropane-1-ylcarbonyl]-4-({4-[(4-diethyl-amino)carbonyl]-2-nitrophenyl}amino)-L-phenylalanine The carboxylic acid was synthesized as follows: 200 mg of 4-fluoro-5-nitrobenzoic acid was added to 30 mg of a resin having an aniline structure obtained by reducing nitro group in the same manner as that of step 4 in Example 85. 500 μl of DMSO was added thereto and the reaction was conducted at 45° C. for 48 hours. The reaction solution was removed and the resin was washed with DCM, NMP and DCM 3 times each. The obtained resin was reacted with diethylamine in the same manner as in the synthesis of the amido bond in step 5 in Example 85. The obtained resin was treated with trifluoroacetic acid for 1 hour and then filtered out. The filtrate was concentrated to obtain the intended compound without the purification.

MS (ESI positive): 540

[$C_{27}H_{33}F_3N_5O_7$: 539]

EXAMPLES 399 TO 410

In those Examples, carboxylic acids (general formula 1-10) were synthesized by using a corresponding benzoic acid and a corresponding amine or only a benzene derivative without the amine in the same manner as that of Example 398.

$L_{20}$, $L_{21}$, $L_{22}$, $L_{23}$ and $L_{24}$ in Table 2-9 are each a substituent in general formula (1-10) given below.

TABLE 2-9

(1-10)

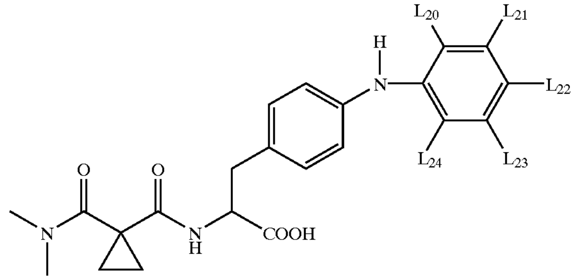

| Example | L20 | L21 | L22 | L23 | L24 | MS Found (MH+) |
|---|---|---|---|---|---|---|
| 398 | NO2 | H | Et2NCO | H | H | 540 |
| 399 | NO2 | H | H | H | Et2NCO | 540 |
| 400 | NO2 | H | 2-Et2NCO-Benzoyl | H | H | 589 |
| 401 | Et2NCO | H | NO2 | H | H | 540 |
| 402 | Et2NCO | H | H | H | NO2 | 540 |
| 403 | NO2 | H | 1-Pyrrolidinyl-CO | H | H | 538 |
| 404 | NO2 | H | N-Benzyl-N-MethylaminoCO— | H | H | 588 |
| 405 | H | CF3 | NO2 | H | H | 509 |
| 406 | H | Me | NO2 | H | H | 455 |
| 407 | H | NO2 | NO2 | H | H | 486 |
| 408 | Cl | H | NO2 | H | H | 476 |
| 409 | CF3 | H | NO2 | H | H | 509 |
| 410 | Me | H | NO2 | H | H | 455 |

EXAMPLE 411

Synthesis of N-[1-(N,N-dimethylaminocarbonyl)cyclopropane-1-ylcarbonyl]-4-{[(1,1'-biphenyl-2-ylamino)carbonothioyl]amino}-L-phenylalanine The carboxylic acid was synthesized as follows: 200 μl of 2-phenyl-phenylisothiocyanate was added to 30 mg of a resin having an aniline structure obtained by reducing nitro group in the same manner as that of step 4 in Example 85. 500 μl of DCM was added thereto and the reaction was conducted at 25° C. for 24 hours. The reaction solution was removed and the resin was washed with DCM, NMP and DCM 3 times each. The reaction solution was removed and the obtained resin was treated with trifluoroacetic acid for 1 hour an then filtered out. The filtrate was concentrated to obtain the intended compound without the purification.

MS (ESI positive): 531

[$C_{29}H_{30}N_4O_4S$: 530]

EXAMPLES 412 TO 428

The carboxylic acids (general formula 1-11) were synthesized by using a corresponding isocyanate or isothiocyanate in the same manner as that of Example 411. In particular, compounds in Examples 423 to 425 in Table 2-10 were obtained by using 4-fluoro-3-nitrobenzene isocyanate and compounds in Examples 426 to 428 were obtained by using 2-fluoro-5-nitrobenzene isocyanate. In these Examples, after forming a urea, 500 μl of DMSO and 100 μl of a corresponding amine were added thereto, and the reaction was conducted at 45° C. for 48 hours. After the treatment with trifluoroacetic acid in the same manner as that of Example 411 for 1 hour, the resin was filtered out. The filtrate was concentrated to obtain the intended compound without the purification.

$L_{25}$, $L_{26}$, $L_{27}$, $L_{28}$, $L_{29}$ and $L_{30}$ in Table 2-10 are each a substituent in general formula (1-11) given below.

TABLE 2-10

(1-11)

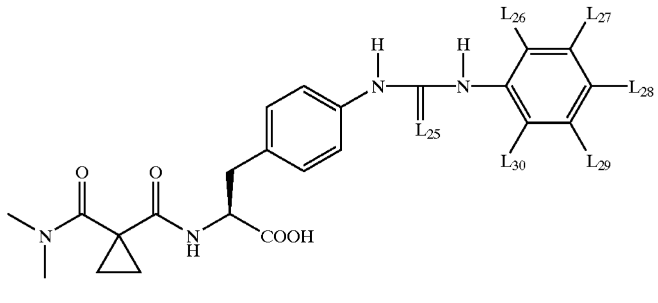

| Example | L25 | L26 | L27 | L28 | L29 | L30 | MS Found (MH+) |
|---|---|---|---|---|---|---|---|
| 411 | S | H | H | H | H | ph | 531 |
| 412 | S | Cl | H | H | H | H | 489 |
| 413 | S | Cl | H | H | CF3 | H | 557 |

TABLE 2-10-continued (1-11)

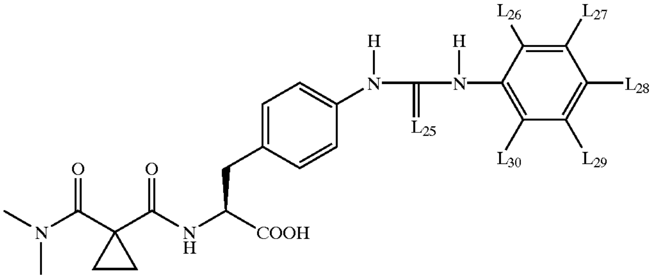

| Example | L25 | L26 | L27 | L28 | L29 | L30 | MS Found (MH+) |
|---|---|---|---|---|---|---|---|
| 414 | S | CN | H | H | H | H | 480 |
| 415 | S | Br | H | H | Br | H | 613 |
| 416 | S | Cl | H | Cl | H | H | 524, 526 |
| 417 | S | Et | H | H | H | Et | 511 |
| 418 | S | MeO | H | MeO | H | H | 515 |
| 419 | S | NO2 | H | H | H | H | 500 |
| 420 | O | H | CN | H | H | H | 464 |
| 421 | O | Cl | H | H | H | Cl | 508 |
| 422 | O | H | H | I | H | H | 565 |
| 423 | O | H | NO2 | Et2N | H | H | 555 |
| 424 | O | H | NO2 | 1-Pyrrolidinyl | H | H | 553 |
| 425 | O | H | NO2 | N-Benzyl-N-methylamino | H | H | 603 |
| 426 | O | Et2N | H | H | NO2 | H | 555 |
| 427 | O | 1-Pyrrolidinyl | H | H | NO2 | H | 553 |
| 428 | O | N-Benzyl-N-methylamino | H | H | NO2 | H | 603 |

EXAMPLE 429

Synthesis of N-[1-(N,N-dimethylaminocarbonyl)cyclopropane-1-ylcarbonyl]-4-[ethyl(2-nitrobenzyl)amino]-L-phenylalanine The carboxylic acid was synthesized as follows: 2.24 g of 2-nitrobenzenesulfonyl chloride was added to 1.3 g of a resin having an aniline structure obtained by reducing nitro group in the same manner as that of step 4 in Example 85. Then the reaction was conducted in 2.3 ml of 2,6-lutidine and 30 ml of DCM at 25° C. for 48 hours. The reaction solution was removed and the resin was washed with DCM, NMP and DCM 3 times each. 200 μl of ethyl iodide, 600 mg of potassium carbonate and 1 ml of NMP were added to 30 mg of the resin in the same manner as that of Example 380. The obtained solution was shaken at 35° C. for 24 hours. The reaction solution was removed, and the resin was washed with DCM, NMP and DCM 3 times each. 200 μl of DBU, 400 μl of 2-mercaptoethanol and 500 μl of NMP were added to 30 mg of the obtained resin, and the mixture was shaken at room temperature for 24 hours. The reaction solution was removed, and the resin was washed with DCM, NMP and DCM 3 times each. 200 μl of 2-nitrobenzyl bromide, 500 μl of diisopropylethylamine and 500 μl of NMP were added to the resin and the reaction was conducted at 80° C. for 24 hours. The reaction solution was removed and the obtained resin was washed with DCM, NMP and DCM 3 times each. The obtained resin was treated with 100% trifluoroacetic acid for 1 hour an then filtered out. The filtrate was concentrated to obtain the intended compound without the purification.

MS (ESI positive): 483

[$C_{25}H_{30}N_4O_6$: 482]

EXAMPLES 430 TO 444

The carboxylic acids (general formula 1-12) were synthesized by using a corresponding bromide, chloride or iodide in the same manner as that of Example 429. In Examples 430, 431, 432 and 441, the second alkylation treatment in Example 429 was omitted.

$L_{31}$ and $L_{32}$ in Table 2-11 are each a substituent in general formula (1-12) given below.

TABLE 2-11

(1-12)

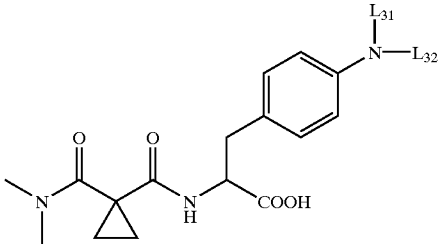

| Example | L31 | L32 | MS Found (MH+) |
|---|---|---|---|
| 430 | 2-MePh | H | 536 |
| 431 | 3-NO2Ph | H | 476 |
| 432 | 2,4-DiCF3Ph | H | 494 |
| 433 | 2-MePh | Et | 564 |
| 434 | 3-NO2Ph | Et | 504 |
| 435 | 2,4-DiCF3Ph | Et | 522 |
| 436 | 2-MePh | Allyl | 576 |
| 437 | 3-NO2Ph | Allyl | 516 |
| 438 | 2,4-DiCF3Ph | Allyl | 534 |
| 439 | 3-NO2Ph | Tetrahydrofurfuryl | 560 |
| 440 | 2,4-DiCF3Ph | Tetrahydrofurfuryl | 578 |
| 441 | PhSCH2 | H | 456 |
| 442 | PhSCH2 | Et | 484 |
| 443 | PhSCH2 | Allyl | 496 |
| 444 | PhSCH2 | Tetrahydrofurfuryl | 540 |

EXAMPLE 445

Synthesis of N-{2-[4-(4-hydroxyphenyl)piperazine-1-ylcarbonyl]-2-ethylbutanoyl}-4-benzoyl-L-phenylalanine 30 mg of the intermediate resin obtained in Example 449 was shaken in DMF for 30 minutes and then taken out by the filtration. The resin was treated in 300 μl of 20% solution of piperidine in DMF for 3 minutes and then for 10 minutes. The resin was washed with DMF and DCM and then shaken in a solution of 36.5 mg of diethylmalonic acid, 106 μl of DIC and 93 mg of HOAt in 600 μl of NMP overnight. After washing with DMF and DCM, the resin was shaken in a solution (600 μl) of 41 mg of 4-(4-hydroxyphenyl) piperazine, 31 mg of HOAt and 35 μl of DIC in NMP overnight. After washing with DMF, DCM, methanol and diethyl ether, the resin was shaken in 300 μl of 95% aqueous TFA solution for 1 hour. After the filtration, the filtrate was dried under reduced pressure, and the product was taken by HPLC and freeze-dried to obtain 1.7 mg of the intended compound in the form of a white solid.

MS (ESI positive): 572

[$C_{33}H_{37}N_3O_6$: 571]

EXAMPLE 446

Synthesis of N-[1-(N,N-dimethylaminocarbonyl) cyclopropane-1-ylcarbonyl]-4-(4-phenyl-1,3-thiazole-2-yl)-L-phenylalanine A resin having nitryl group was synthesized in the same manner as that of Example 85 except that Fmoc-Phe(4-CN)—OH was used in step 1 and 1,1-cyclopropanedicarboxylic acid and dimethylamine were used in step 3. 1 mg of O,O-diethyl dithiophosphate and then 5 ml of THF/water (4/1) were added to 200 mg of the obtained resin and the reaction was conducted at 77° C. for 24 hours. The reaction solution was removed, and the resin was washed with DCM, NMP and DCM 3 times each. 500 μl of α-bromoacetophenone and 1 ml of NMP were added to 30 mg of the obtained resin, and the resultant mixture was shaken at 77° C. for 24 hours. The reaction solution was removed, and the resin was washed with dichloromethane, NMP and dichloromethane 3 times each. The obtained solution was concentrated and purified by the reversed-phase HPLC (SYMMETRY 19*50 mm, mobile phase: water/acetonitrile each containing 0.1% of TFA) to obtain 2.0 mg of the intended compound.

MS (ESI positive): 464

[$C_{25}H_{25}N_3O_4S$: 463]

EXAMPLE 447

Synthesis of N-[1-(N,N-dimethylaminocarbonyl) cyclopropane-1-ylcarbonyl]-4-(8H-indeno [1,2-d][1,3] thiazole-2-yl)-L-phenylalanine A resin having nitryl group was synthesized in the same manner as that of Example 85 except that Fmoc-Phe(4-CN)—OH was used in step 1 and 1,1-cyclopropanedicarboxylic acid and dimethylamine were used in step 3. 1 mg of O,O-diethyl dithiophosphate and then 5 ml of THF/water (4/1) were added to 200 mg of the obtained resin and the reaction was conducted at 77° C. for 24 hours. The reaction solution was removed, and the resin was washed with dichloromethane, NMP and dichloromethane 3 times each. 500 μl of 2-bromo-1-indanone and 1 ml of NMP were added to 30 mg of the obtained resin, and the resultant solution was shaken at 77° C. for 24 hours. The reaction solution was removed, and the resin was washed with dichloromethane, NMP and dichloromethane 3 times each. The obtained solution was concentrated and purified by the reversed-phase HPLC (SYMMETRY 19*50 mm, mobile phase: water/acetonitrile each containing 0.1% of TFA) to obtain 2.1 mg of the intended compound.

MS (ESI positive): 476

[$C_{26}H_{25}N_3O_4S$: 475]

EXAMPLE 448

Synthesis of N-(2-dimethylaminocarbonyl-2-methylpropanoyl)-O-phenyl-L-tyrosine 4.19 g of N-Boc Tyrosine Methyl ester, 2.58 g of copper (I) acetate, 3.46 g of phenylboric acid, 135 ml of DCM, 3 g of molecular sieve 4A and 5.73 ml of pyridine were fed into a 200 ml flask. After stirring at room temperature for 4 days, 1 g of molecular sieve 4A, 1.73 g of phenylboric acid, 1.29 g of copper (I) acetate and 2.86 ml of pyridine were added to the mixture, and the mixture were stirred at room temperature overnight. The reaction mixture was filtered through Celite, concentrated and purified with a medium pressure column to obtain 2.77 g of methyl ester of N-Boc-O-phenyltyrosine in the form of a colorless, viscous liquid.

The compound obtained as described above was added to 39 ml of 4 M solution of hydrogen chloride in ethyl acetate. They were stirred at room temperature for 4 hours and then concentrated to obtain 2.16 g of hydrochloride of methyl ester of N-Boc-O-phenyltyrosine in the form of a white solid.

29 mg of this compound, 36 mg of WSC HCl, 16 ml of HOBt·$H_2O$, 15 mg of dimethylmalonic acid monodimethylamide, 1 ml of DCM and 13 μl of triethylamine were mixed together, and the mixture was stirred at room temperature overnight. The reaction solution was washed with 1 M aqueous hydrochloric acid solution, saturated aqueous sodium hydrogencarbonate solution and water. The product was dried over magnesium sulfate, concentrated and purified by TLC to obtain 19 mg of a white solid.

1 ml of THF, 1 ml of methanol, 2.3 mg of lithium hydroxide monohydrate and 0.5 ml of water were added to the obtained compound, and the mixture stirred at room temperature for 3 hours and then concentrated under reduced pressure. The product was dissolved in water and washed with DCM. Ethyl acetate was added to the aqueous layer. After adding 55 μl of 1 M aqueous hydrochloric acid solution, the obtained mixture was stirred and then separated into layers. The organic layer was dried over brine and then over magnesium sulfate, and concentrated under reduced pressure to obtain 3.5 mg of the intended compound in the form of an almond-colored solid.

MS (ESI positive): 399

[$C_{27}H_{33}N_5O_7$: 398]

EXAMPLE 449

Synthesis of N-[4-(4-hydroxyphenyl)piperazino-carbonylcyclopropane-1-ylcarbonyl]-4-benzoyl-L-phenylalanine 430 mg of Wang resin was immersed in DMF for 1.5 hours. DMF was removed by the filtration, and the resin was shaken in a solution of 128 μl of DIC, 416 mg of N-Fmoc-4-benzoylphenylalanine $H_2O$ and 4 mg of DMAP in 3.6 ml of DMF at room temperature for 4 hours. The resin was washed with DMF and DCM, and then shaken in a solution of 309 μl of acetic anhydride and 264 μl of pyridine in 3.3 ml of DMF for 2 hours. After washing with DMF, DCM, methanol and diethyl ether and drying under reduced pressure, 530 mg of an intermediate resin was obtained.

30 mg of the intermediate resin was shaken in DMF for 30 minutes and then filtered. The resin was treated with 300 μM 1 of 20% solution of piperidine in DMF for 3 minutes and then for 10 minutes. After washing with DMF and DCM, a solution of 29 mg of 1,1-cyclopropanedicarboxylic acid, 106 μl of DEC and 93 mg of HOAt in 600 μl of NMP was added to the product and they were shaken overnight. After washing with DMF and DCM, 41 mg of 4-(4-hydroxyphenyl)piperazine, 31 mg of HOAt, 35μl of DIC and 600 μl of NMP were added to the resin and they were shaken overnight. After washing with DMF, DCM, methanol and diethyl ether followed by the shaking in 300 μl of 95% aqueous TFA solution for 1 hour, the reaction mixture was filtered. The filtrate was dried under reduced pressure and the product was purified by HPLC and then freeze-dried to obtain 0.04 mg of the intended compound in the form of a white solid.

MS (ESI positive): 542

[$C_{31}H_{31}N_3O_6$: 541]

EXAMPLE 485

Synthesis of N-[2-ethyl-2-(pyrrolidine-1-ylcarbonyl)-butanoyl]-4-benzoyl-L-phenylalanine The intermediate resin obtained in Example 449 was shaken in DMF for 30 minutes and then filtered. The resin was treated with 20% solution of piperidine in DMF for 3 minutes and then for 10 minutes. After washing with DMF and DCM, the resin was shaken in a solution of diethylmalonic acid, DIC and HOAt in NMP overnight. The resin was washed with DMF and DCM and then shaken in a solution of pyrrolidine, HOAt and DIC in NMP overnight. After washing with DMF, DCM, methanol and diethyl ether followed by the shaking in 95% aqueous TFA solution for 1 hour, the reaction mixture was filtered. The filtrate was dried under reduced pressure and the product was purified by HPLC and then freeze-dried to obtain the intended compound in the form of a white solid.

MS (ESI positive): 465

[$C_{27}H_{32}N_2O_5$: 464]

EXAMPLE 486

Synthesis of N-[2-ethyl-2-(phenylsulfonyl)butanoyl]-O-(2,6-dichlorobenzyl)-L-tyrosine Step 1 Synthesis of 2-ethyl-2-(phenylsulfonyl)Butanoic Acid Methyl phenylsulfonylacetate (0.64 ml, 4.0 mmol) was diluted with DMF (5 ml). Sodium hydride (384 mg, 16 mmol) and ethyl bromide (1.19 ml, 16 mmol) were added thereto under argon atmosphere. The mixture was stirred at room temperature overnight. Water was added to the reaction mixture under cooling with ice to terminate the reaction. After the extraction with ethyl acetate (10 ml×3), the organic layers were combined together, dried and concentrated under reduced pressure. The residue was purified by the silica gel column chromatography (hexane, hexane/ethyl acetate, 100/1) to obtain an intermediate product. The intermediate product (532 mg, 1.97 mmol) was dissolved in THF (4 ml). Water (70.9 μl, 3.84 mmol) and tBuOK (1.77 g, 15.8 mmol) were added to the obtained solution. The reaction mixture was stirred at room temperature for 4 days. Additional water (35.5 μl, 1.97 mmol) and tBuOK (1.55 g, 13.8 mmol) were added to the obtained solution. After stirring at room temperature for 9 days, the reaction mixture was diluted with DCM (10 ml). The resultant mixture was extracted with water (10 ml). pH of the aqueous layer was adjusted to 2. After the extraction with DCM (10 ml×3), the organic layers were combined together, dried and concentrated under reduced pressure to quantitatively obtain 481 mg of the intended compound.

$^1$H-NMR ($CDCl_3$) δ=1.10(6H, t, J=7.4 Hz), 1.99–2.28 (4H, m), 7.52–7.74(3H, m), 7.85–7.93(2H, m).

Step 2

30 mg of the resin obtained in Example 1 was added to a solution of 2-ethyl-2-(phenylsulfonyl)butanoic acid, HOAt and DIC in DMF to conduct the reaction at room temperature for 20 hours. The reaction solution was removed, and the resin was washed with DMF, methanol and dichloromethane 6 times each. The resin was then treated with 95% aqueous trifluoroacetic acid solution for 1 hour. The resin was taken by the filtration and then washed with acetonitrile. The filtrates were combined together and concentrated. After the purification by the reversed-phase HPLC [Inertsil ODS column, developer: water/acetonitrile (TFA 0.05%)], the intended compound was obtained.

MS (ESI positive): 578

[$C_{28}H_{29}NO_6Cl_2S$: 577]

EXAMPLE 487

Synthesis of N-[2-ethyl-2-(pyrrolidine-1-ylcarbonyl)butanoyl]-O-(2,6-dichlorobenzyl)-3,5-diiodo-L-tyrosine Methyl ester of N-Boc-3,5-diiodo-L-tyrosine (50 mg) was dissolved in 4 N solution (1 ml) of hydrochloric acid in dioxane, and the reaction was conducted for 1 hour. The reaction solution was concentrated under reduced pressure, and the residue was dissolved in NMP (0.5 ml)/DIEA (0.012 ml). Separately, a solution (0.5 ml) of diethylmalonic acid (23 mg), DIC (0.066 ml) and HOAt (58 mg) in NMP was prepared, and NMP-DIEA prepared as described above was added dropwise to the NMP solution. The reaction was conducted for 2 hours, and then ethyl acetate was added to the reaction solution. After washing with water and saturated aqueous sodium chloride solution, the product was dried and concentrated under reduced pressure. The white solid thus obtained was dissolved in NMP (1 ml). Pyrrolidine (0.0054 ml) was added to the obtained solution, and they were stirred for 16 hours. A small amount of water was added to the reaction mixture. After the extraction with dichloromethane/isopropanol (2/1, 30 ml, 3 times), the extract was dried and then concentrated under reduced pressure. The obtained yellow oil was dissolved in methanol (0.25 ml). 0.1 N aqueous LiOH solution was added to the obtained solution, and they were stirred for 5 hours. A small amount of water was added to the reaction mixture. After the extraction with dichloromethane/isopropanol (2/1, 30 ml, 3 times), the extract was dried and then concentrated under reduced pressure. The residue was purified by the reversed-phase HPLC [Waters Co., Symmetry C18 column (5 μM; 19 mm diameter×50 mm), developer: water/acetonitrile (TFA 0.05%)] to obtain the intended compound (0.4 mg).

MS (ESI positive): 787

[$C_{27}H_{32}N_2O_5$: 786]

TEST EXAMPLE

CAM Antagonist Activity (VCAM-1/α 4 β 1 Binding Assay)

The capacity of a test substance antagonistic to the binding of cell strain Jurkat (ATCC TIB-152) of human T cells, known to express integrin α 4 β 1, to VCAM-1 was determined.

100 μl/well of a solution (500 ng/ml) of recombinant human VCAM-1 (R & D systems) solution diluted with buffer A (0.1 M $NaHCO_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace® (Dainippon Pharmaceutical Co., Ltd.) with PBS to ¼ concentration was added in an amount of 150 μl/well. After the incubation at room temperature for 1 hour, buffer B was removed and the plate was washed with PBS once.

Jurkat cells were washed with Dulbecco modified Eagle medium (SIGMA, hereinafter referred to as "DMEM") twice and then incubated in DMEM containing 10 μg/ml of Calcein-AM (Wako Pure Chemical Industries, Ltd.) at 37° C. in dark place for 30 minutes to label with fluorescence. The cells were again suspended in a binding buffer (20 mM HEPES, DMEM containing 0.1% BSA).

50 $\mu$l of a test substance of various concentrations obtained by the dilution with the binding buffer was added to the plate. Immediately thereafter, 50 $\mu$l (final volume: 100 $\mu$l/well) of the fluorescent Jurkat cells ($4\times10^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of Jurkat cells bound to VCAM-1 and remaining on the plate. The binding rate of each test material in various concentrations was determined while the fluorescent strength of the test material-free well was determined to be 100%. The concentration $IC_{50}$ for the 50% binding inhibition was calculated.

The obtained test results are shown in Table 3. The activities were classified into group A wherein $IC_{50}$ was 0.02 $\mu$mol/l or below, group B wherein $IC_{50}$ was higher than 0.02 $\mu$mol/l and not above 0.1 $\mu$mol/l, group C wherein $IC_{50}$ was higher than 0.1 $\mu$mol/l and not above 2 $\mu$mol/l, and group D wherein $IC_{50}$ was higher than 2 $\mu$mol/l and not above 10 $\mu$mol/l.

TEST EXAMPLE

VCAM Antagonistic Activity (VCAM-1/α 4 β 7 Binding Assay)

The capacity of a test substance antagonistic to the binding of lymphoma cell strain RPMI-8866 of human B cells, known to express integrin α 4 β 7, to VCAM-1 was determined.

100 $\mu$l/well of a solution (500 ng/ml) of recombinant human VCAM-1 (R & D systems) solution diluted with buffer A (0.1 M $NaHCO_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace® (Dainippon Pharmaceutical Co., Ltd.) with PBS to ¼ concentration was added in an amount of 150 $\mu$l/well. After the incubation at room temperature for 1 hour, buffer B was removed and the plate was washed with PBS once.

RPMI-8866 cells were incubated in Dulbecco modified Eagle medium containing 10 $\mu$g/ml of Calcein-AM (Wako Pure Chemical Industries, Ltd.) (SIGMA, hereinafter referred to as "DMEM") at 37° C. for 30 minutes to label with fluorescence. The cells were again suspended in a binding buffer (20 mM HEPES, DMEM containing 0.1% BSA) containing 4 mM of $MnCl_2$.

50 $\mu$l of a test substance of various concentrations obtained by the dilution with the binding buffer was added to the plate. Immediately thereafter, 50 $\mu$l (final volume: 100 $\mu$l/well) of the fluorescent RPMI-8866 cells ($4\times10^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of RPMI-8866 cells bound to VCAM-1 and remaining on the plate. The binding rate of each test material in various concentrations was determined while the fluorescent strength of the test material-free well was determined to be 100%. The concentration $IC_{50}$ for the 50% binding inhibition was calculated.

The obtained test results are shown in Table 3. The activities were classified into group A wherein $IC_{50}$ was 0.02 $\mu$mol/l or below, group B wherein $IC_{50}$ was higher than 0.02 $\mu$mol/l and not above 0.1 $\mu$mol/l, group C wherein $IC_{50}$ was higher than 0.1 $\mu$mol/l and not above 2 $\mu$mol/l, and group D wherein $IC_{50}$ was higher than 2 $\mu$mol/l and not above 10 $\mu$mol/l.

TABLE 3

Results of the determination of VCAM antagonistic activity (IC50, umol/L): 10 ≧ D > 2.0 ≧ C > 0.1 ≧ B > 0.02 ≧ A

| Example | α 4 β 7 | α 4 β 1 |
|---|---|---|
| 2 | B | C |
| 3 | A | C |
| 5 | C | C |
| 6 | C | D |
| 7 | C | C |
| 8 | C | C |
| 9 | C | C |
| 17 | C | C |
| 21 | C | D |
| 23 | C | D |
| 29 | C | C |
| 32 | B | C |
| 33 | B | C |
| 34 | B | C |
| 35 | A | B |
| 36 | B | C |
| 37 | B | D |
| 38 | C | C |
| 39 | B | C |
| 40 | B | C |
| 41 | B | C |
| 42 | B | C |
| 43 | A | C |
| 44 | A | C |
| 45 | B | C |
| 46 | A | C |
| 47 | A | C |
| 48 | B | C |
| 49 | B | C |
| 50 | B | C |
| 51 | B | C |
| 52 | A | B |
| 53 | A | C |
| 54 | A | B |
| 55 | A | B |
| 56 | A | C |
| 57 | B | C |
| 58 | C | C |
| 59 | B | C |
| 60 | C | C |
| 61 | B | C |
| 62 | B | C |
| 63 | B | C |
| 64 | B | C |
| 65 | A | C |
| 66 | B | C |
| 67 | B | C |
| 68 | A | B |
| 69 | A | C |
| 70 | A | B |
| 71 | A | B |
| 72 | A | B |
| 73 | A | B |
| 74 | A | C |
| 75 | A | C |
| 76 | A | C |

TABLE 3-continued

| Results of the determination of VCAM antagonistic activity (IC50, umol/L): 10 ≧ D > 2.0 ≧ C > 0.1 ≧ B > 0.02 ≧ A | | |
|---|---|---|
| Example | α 4 β 7 | α 4 β 1 |
| 77 | A | C |
| 78 | A | C |
| 79 | A | C |
| 80 | A | C |
| 81 | A | C |
| 82 | A | B |
| 83 | A | B |
| 84 | A | C |
| 85 | A | C |
| 86 | B | C |
| 87 | B | C |
| 88 | C | C |
| 89 | C | C |
| 90 | B | C |
| 91 | A | A |
| 92 | A | B |
| 93 | A | C |
| 94 | A | B |
| 95 | A | B |
| 96 | A | B |
| 97 | A | B |
| 98 | A | B |
| 99 | B | B |
| 100 | B | C |
| 101 | B | C |
| 102 | A | C |
| 103 | B | C |
| 104 | B | C |
| 105 | B | C |
| 463 | C | C |
| 464 | B | C |
| 465 | A | C |
| 466 | A | B |
| 467 | A | C |
| 468 | A | C |
| 472 | C | D |
| 477 | A | B |
| 478 | A | B |
| 479 | A | B |
| 480 | A | B |
| 481 | A | B |
| 482 | A | C |
| 483 | A | B |
| 484 | A | B |

It is thus apparent that the new phenylalanine derivatives exhibited an excellent α-integrin inhibiting activity.

Since the new phenylalanine derivatives of the present invention have excellent α-integrin inhibiting activity, the present invention provides a therapeutic agent or preventive agent for diseases in which α 4 integrin-depending adhesion process participates in the pathology, such as inflammatory diseases, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection.

What is claimed is:

1. A phenylalanine compound of the following general formula (1) or a pharmaceutically acceptable salt thereof:

(1)

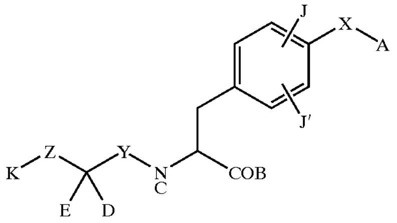

wherein X is —O—,

Y is —C(=O)—,

Z is —C(=O)—,

A represents a group of general formula (2), a group of any of general formulae (2-1) to (2-5), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with a group of general formula (2), a lower alkyl group substituted with an aryl group(s) or a lower alkyl group substituted with a heteroaryl group(s):

(2)

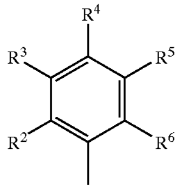

wherein $R^2$, $R^3$, $R^4$, $R^5$ and $R^6$ may be the same or different from one another, and each represents a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom (s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group:

(2-1)

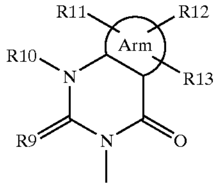

(2-2)

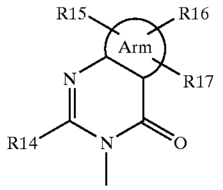

(2-3)

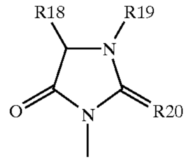

(2-4)

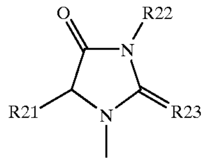

(2-5)

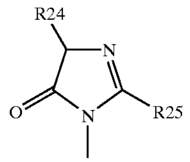

wherein Arm represents benzene ring or an aromatic ring containing 1, 2, 3 or 4 hetero atoms selected from among oxygen, sulfur and nitrogen atoms, $R^9$ represents an oxygen atom, a substituted or unsubstituted imino group or sulfur atom, $R^{10}$, $R^{11}$, $R^{12}$ and $R^{13}$ may be the same or different from one another and each represents a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom (s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, $R^{14}$, $R^{15}$, $R^{16}$ and $R^{17}$ may be the same or different from one another and each represents a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), an alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, $R^{20}$ represents an oxygen atom, a substituted or unsubstituted imino group or sulfur atom, $R^{18}$ and $R^{19}$ may be the same or different from each other and each represents a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group, a halogeno-lower alkenyl group, a hydroxy-lower alkyl group, a hydroxy-lower alkenyl group or a substituted or unsubstituted amino-lower alkyl group, or $R^{18}$ and $R^{19}$ may be bonded together to form a ring which may contain one or two oxygen, nitrogen or sulfur atoms, and the substituents of the ring include hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, $R^{23}$ represents an oxygen atom, a substituted or unsubstituted imino group or sulfur atom, $R^{21}$ and $R^{22}$ may be the same or different from each other and each represent a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom (s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, $R^{24}$ and $R^{25}$ may be the same or different from each other and each represents a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom (s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, B represents a hydroxyl group or a lower alkoxyl group, C represents a hydrogen atom or a lower alkyl group, D and E may be the same or different and each represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with an aryl group(s), a lower alkenyl group substituted with a heteroaryl group(s), a halogeno-lower alkyl group, a lower alkoxy-lower alkyl group, a hydroxy-lower alkyl group, a lower alkylthio-lower alkyl group, a mercapto-lower alkyl group or a substituted or unsubstituted amino-lower alkyl group, or D and E may be bonded together to form a ring which may contain one or two oxygen, nitrogen or sulfur atoms, K represents $OR^7$, $NR^7R^8$, $NHNR^7R^8$, $NR^7NHR^8$, $SR^7$ or $R^7$ wherein $R^7$ and $R^8$ may be the same or different from each other and each represents a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group, a halogeno-lower alkenyl group, a hydroxy-lower alkyl group, a hydroxy-lower alkenyl group or a substituted or unsubstituted amino-lower alkyl group, or $R^7$ and $R^8$ may be bonded together to form a ring which may contain one or two oxygen, nitrogen or sulfur atoms; and the substituents of the ring include hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and J and J' may be the same or different from each other and each represents a hydrogen atom, a halogen atom, a lower alkyl group, a lower alkyloxy group or nitro group.

2. The phenylalanine compound or pharmaceutically acceptable salt thereof according to claim 1, wherein B represents a hydroxyl group, C represents a hydrogen atom, D and E may be the same or different and each represents a lower alkyl group, or D and E may be bonded together to form a ring which may contain one or two oxygen, nitrogen or sulfur atoms, J and J' each represent hydrogen atom.

3. The phenylalanine compound or pharmaceutically acceptable salt thereof according to claim 2, wherein A represents a group of general formula (2), a group of any of general formulae (2-1) to (2-5), a lower alkyl group substituted with a group of general formula (2), a cycloalkyl group which may contain a hetero atom(s) in the ring thereof, or a heteroaryl group.

4. The phenylalanine compound or pharmaceutically acceptable salt thereof according to claim 2, wherein K represents $NR^7R^8$ or $NHNR^7R^8$, $R^7$ and $R^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), or $R^7$ and $R^8$ may be bonded together to form a ring which may contain one or two oxygen, nitrogen or sulfur atoms; and the substituents of the ring include a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkoxycarbonyl group, a substituted or unsubstituted carbamoyl group, a lower alkylthio group, a lower alkylsulfonyl group and a substituted or unsubstituted sulfamoyl group.

5. The phenylalanine compound or pharmaceutically acceptable salt thereof according to claim 1, wherein A represents a lower alkyl group substituted with a group of general formula (2), $R^2$, $R^3$, $R^4$, $R^5$ and $R^6$ may be the same or different from one another, and each represents a hydrogen atom or a halogen atom, B represents a hydroxyl group, C represents a hydrogen atom, D and E may be the same or different and each represents a lower alkyl group, or D and E may be bonded together to form a ring which may contain one or two oxygen, nitrogen or sulfur atoms, K represents $NR^7R^8$ or $NHNR^7R^8$, $R^7$ and $R^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), or $R^7$ and $R^8$ may be bonded together to form a ring which may contain one or two oxygen, nitrogen or sulfur atoms; and the substituents of the ring include a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and J and J' each represents a hydrogen atom.

6. The phenylalanine compound or pharmaceutically acceptable salt thereof according to claim 5, wherein K represents a group of the formula: $NR^7R^8$.

7. The phenylalanine compound or pharmaceutically acceptable salt thereof according to claim 6, wherein $R^7$ and $R^8$ are bonded together to form a ring.

8. The phenylalanine compound or pharmaceutically acceptable salt thereof according to claim 1, wherein A is represented by any of formulae (2-1) to (2-5).

9. The phenylalanine compound or pharmaceutically acceptable salt thereof according to claim 8, wherein A is represented by formula (2-1).

10. A phenylalanine compound or pharmaceutically acceptable salt thereof according to claim 1, which is selected from the group consisting of:

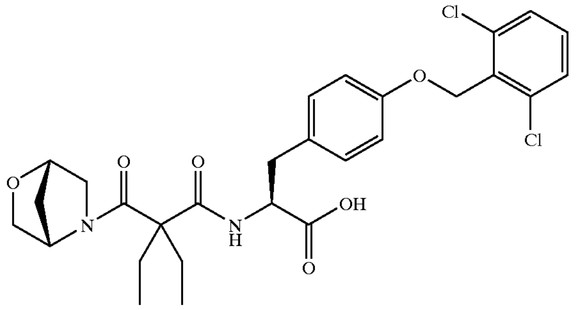

-continued
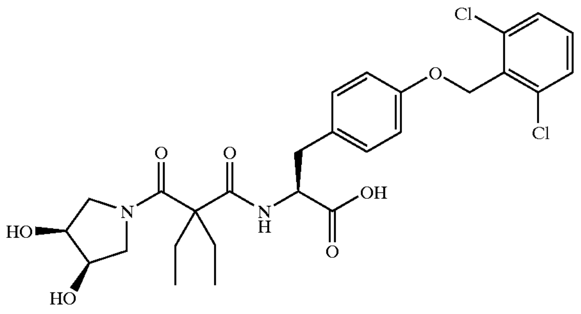
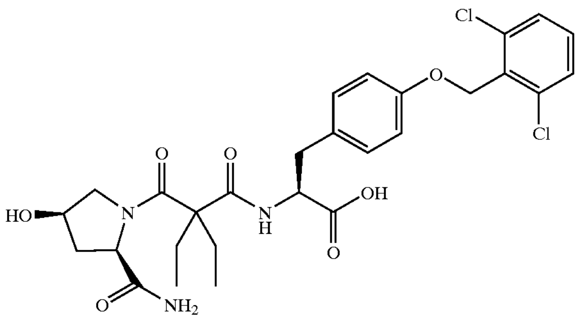
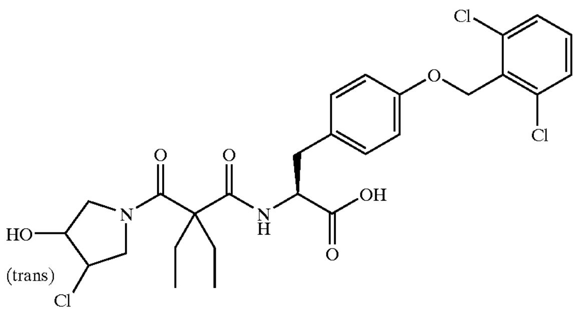
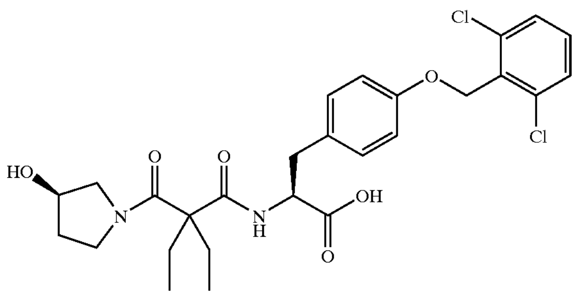
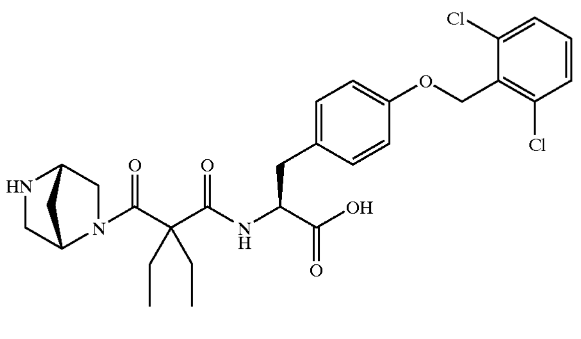
-continued
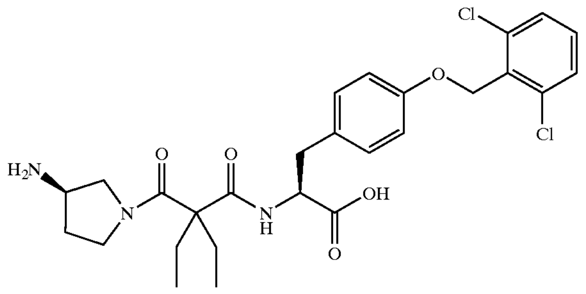
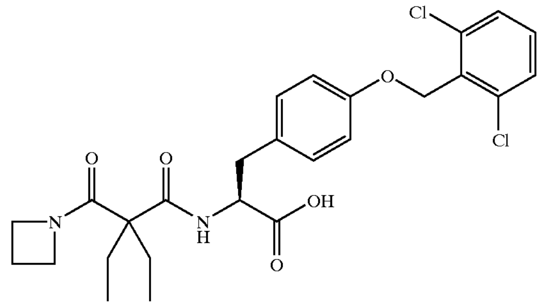
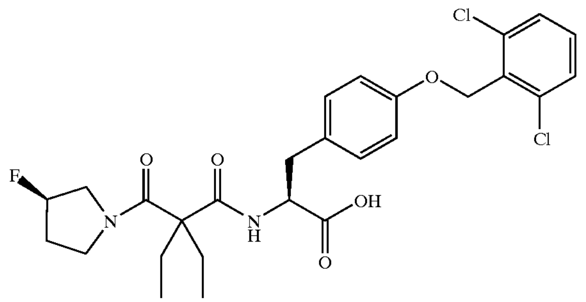
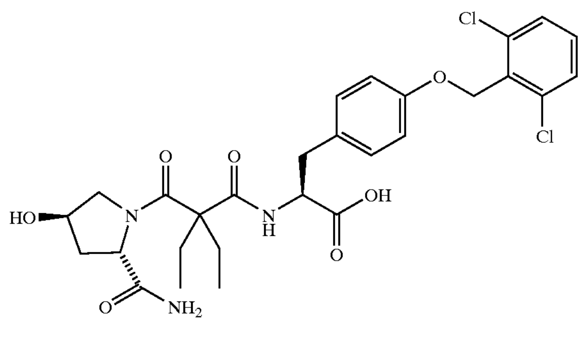
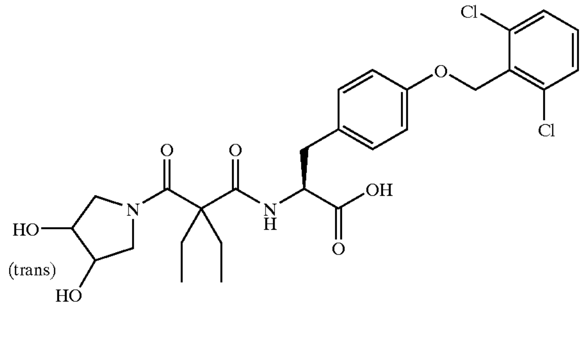

-continued

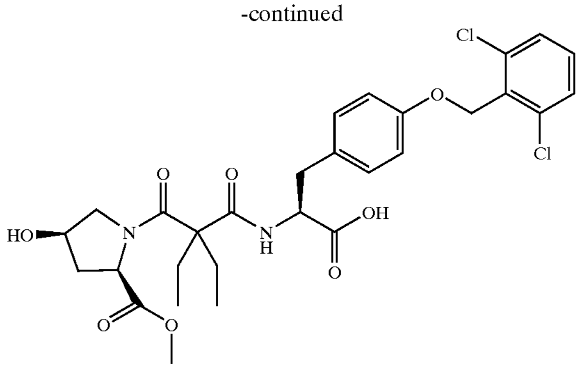

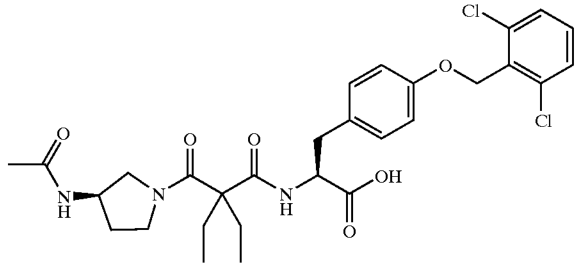

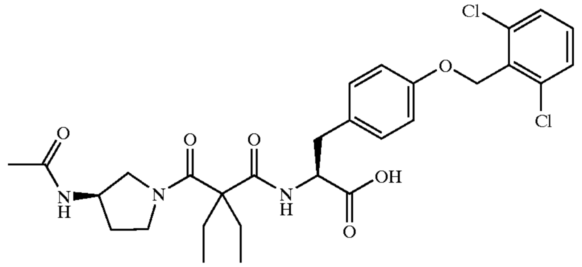

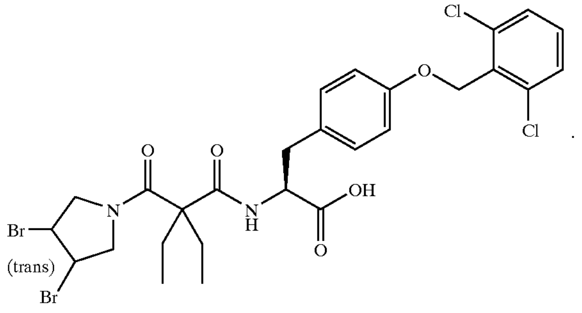

11. The phenylalanine compound or pharmaceutically acceptable salt thereof according to claim 1, wherein A represents a lower alkyl group substituted with a group of general formula (2).

12. A phenylalanine compound of the following general formula (1) or a pharmaceutically acceptable salt thereof:

(1)

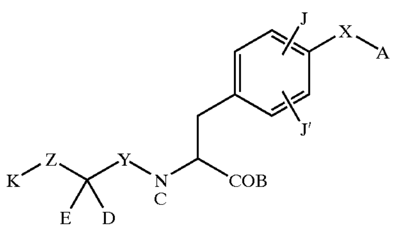

wherein X represents —O—,

Y represents —C(═O),

Z represents —C(═O),

A represents a group of general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with a group of general formula (2), a lower alkyl group substituted with an aryl group(s) or a lower alkyl group substituted with a heteroaryl group(s):

(2)

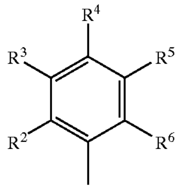

wherein $R^2$, $R^3$, $R^4$, $R^5$ and $R^6$ may be the same or different from one another, and each represents a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom (s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, a carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, B represents a hydroxyl group or a lower alkoxyl group, C represents a hydrogen atom or a lower alkyl group, D and E may be the same or different and each represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with an aryl group(s), a lower alkenyl group substituted with a heteroaryl group(s), a halogeno-lower alkyl group or a hydroxy-lower alkyl group, or D and E may be bonded together to form a ring which may contain one or two oxygen, nitrogen or sulfur atoms, K represents $OR^7$, $NR^7R^8$, $NHNR^7R^8$, $NR^7NHR^8$, $SR^7$ or $R^7$ wherein $R^7$ and $R^8$ may be the same or different from each other and each represents a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a halogeno-lower alkyl group, a halogeno-lower alkenyl group, a hydroxy-lower alkyl group, a hydroxy-lower alkenyl group or a substituted or unsubstituted amino-lower alkyl group, or $R^7$ and $R^8$ may be bonded together to form a ring which may contain one or two oxygen, nitrogen or sulfur atoms; and the substituents of the ring include a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group (s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and J and J' may be the same or different from each other and each represents a hydrogen atom, a halogen atom, a lower alkyl group, a lower alkyloxy group or nitro group.

13. The phenylalanine compound or pharmaceutically acceptable salt thereof according to claim 12, wherein A represents a lower alkyl group substituted with a group of general formula (2), $R^2$, $R^3$, $R^4$, $R^5$ and $R^6$ may be the same or different from one another, and each represents a hydrogen atom or a halogen atom, B represents a hydroxyl group, C represents a hydrogen atom, D and E may be the same or different and each represents a lower alkyl group, or D and E may be bonded together to form a ring which may contain one or two oxygen, nitrogen or sulfur atoms, K represents $NR^7R^8$ or $NHNR^7R^8$, $R^7$ and $R^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), or $R^7$ and $R^8$ may be bonded together to form a ring which may contain one or two oxygen, nitrogen or sulfur atoms; and the substituents of the ring include a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and J and J' each represent a hydrogen atom.

14. A phenylalanine compound or pharmaceutically acceptable salt thereof according to claim 12, which is selected from the group consisting of:

N-[2-(N,N-dimethylaminocarbonyl)-2-methyl-propanoyl]-O-(2,6-dichloro-benzyl)-L-tyrosine;

N-[2-(N,N-diethylaminocarbonyl)-2-methyl-propanoyl]-O-(2,6-dichloro-benzyl)-L-tyrosine;

N-[2-(N,N-dimethylaminocarbonyl)-2-ethyl-butanoyl]-O-(2,6-dichloro-benzyl)-L-tyrosine;

N-[2-(N,N-diethylaminocarbonyl)-2-methyl-butanoyl]-O-(2,6-dichloro-benzyl)-L-tyrosine;

N-[1-(N,N-dimethylaminocarbonyl)cyclopropane-1-ylcarbonyl]-O-(2,6-di-chlorobenzyl)-L-tyrosine;

N-[1-(N,N-diethylaminocarbonyl)cyclopropane-1-ylcarbonyl]-O-(2,6-di-chlorobenzyl)-L-tyrosine;

N-[2-(piperidine-1-ylcarbonyl)-2-methyl-propanoyl]-O-(2,6-dichloro-benzyl)-L-tyrosine;

N-[2-(piperidine-1-ylcarbonyl)-2-ethyl-butanoyl]-O-(2,6-dichlorobenzyl)-L-tyrosine;

N-[1-(piperidine-1-ylcarbonyl)cyclopropane-1-ylcarbonyl]-O-(2,6-dichloro-benzyl)-L-tyrosine;

N-[2-(N-methyl-N-phenylaminocarbonyl)-2-methyl-propanoyl]-O-(2,6-di-chlorobenzyl)-L-tyrosine;

N-[2-(N-methyl-N-phenylaminocarbonyl)-2-ethyl-butanoyl]-O-(2,6-di-chlorobenzyl)-L-tyrosine;

N-[1-(N-methyl-N-phenylaminocarbonyl)cyclopropane-1-ylcarbonyl]-O-(2,6-dichlorobenzyl)-L-tyrosine;

N-[2-(4-hydroxyphenylaminocarbonyl)-2-methyl-propanoyl]-O-(2,6-di-chlorobenzyl)-L-tyrosine;

N-[2-(4-hydroxyphenylaminocarbonyl)-2-ethyl-butanoyl]-O-(2,6-dichloro-benzyl)-L-tyrosine;

N-[1-(4-hydroxyphenylaminocarbonyl)cyclopropane-1-ylcarbonyl]-O-(2,6-dichlorobenzyl)-L-tyrosine;

N-{2-[4-(4-hydroxyphenyl)piperazine-1-ylcarbonyl]-2-methyl-propanoyl}-O-(2,6-di-chlorobenzyl)-L-tyrosine;

N-{2-[4-(4-hydroxyphenyl)piperazine-1-ylcarbonyl]-2-ethyl-butanoyl}-O-(2,6-dichlorobenzyl)-L-tyrosine; and N-{1-[4-(4-hydroxyphenyl)piperazine-1-ylcarbonyl]-2-ethyl-butanoyl}-O-(2,6-dichlorobenzyl)-L-tyrosine.

15. A pharmaceutical composition comprising a phenylalanine compound or a pharmaceutically acceptable salt thereof according to claim 1 and a pharmaceutically acceptable carrier or excipient.

16. A pharmaceutical composition comprising a phenylalanine compound or a pharmaceutically acceptable salt thereof according to claim 12 and a pharmaceutically acceptable carrier or excipient.

17. A method for treating an inflammatory disease in which α4 integrin-depending adhesion process participates in the pathology, comprising administering an effective amount of a phenylalanine compound or a pharmaceutically acceptable salt thereof according to claim 1 to a subject in need thereof.

18. A method for treating an inflammatory disease in which α4 integrin-depending adhesion process participates in the pathology, comprising administering an effective amount of a phenylalanine compound or a pharmaceutically acceptable salt thereof according to claim 12 to a subject in need thereof.

19. A method for treating rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection, comprising administering an effective amount of a phenylalanine compound or a pharmaceutically acceptable salt thereof according to claim 1 to a subject in need thereof.

20. A method for treating rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection, comprising administering an effective amount of a phenylalanine compound or a pharmaceutically acceptable salt thereof according to claim 12 to a subject in need thereof.

* * * * *